US011021514B2

(12) United States Patent
Kawas et al.

(10) Patent No.: US 11,021,514 B2
(45) Date of Patent: Jun. 1, 2021

(54) COMPOUNDS

(71) Applicant: ATHIRA PHARMA, INC., Seattle, WA (US)

(72) Inventors: Leen H. Kawas, Seattle, WA (US); Jasbir Singh, Seattle, WA (US); Lansing Joseph Stewart, Seattle, WA (US); William R. Baker, Seattle, WA (US)

(73) Assignee: Athira Pharma, Inc., Seattle, WA (US)

( * ) Notice: Subject to any disclaimer, the term of this patent is extended or adjusted under 35 U.S.C. 154(b) by 9 days.

(21) Appl. No.: 16/306,277

(22) PCT Filed: Jun. 1, 2017

(86) PCT No.: PCT/US2017/035547
§ 371 (c)(1),
(2) Date: Nov. 30, 2018

(87) PCT Pub. No.: WO2017/210489
PCT Pub. Date: Dec. 7, 2017

(65) Prior Publication Data
US 2020/0010504 A1    Jan. 9, 2020

Related U.S. Application Data

(60) Provisional application No. 62/344,305, filed on Jun. 1, 2016.

(51) Int. Cl.
C07K 5/065    (2006.01)
A61K 9/00     (2006.01)
C07K 5/02     (2006.01)

(52) U.S. Cl.
CPC ........ C07K 5/06078 (2013.01); *A61K 9/0019* (2013.01); *C07K 5/021* (2013.01)

(58) Field of Classification Search
None
See application file for complete search history.

(56) References Cited

U.S. PATENT DOCUMENTS 4,477,440 A   10/1984  Boger et al.
4,639,456 A    1/1987  Trouet et al.
              (Continued)

FOREIGN PATENT DOCUMENTS

CA    2016355 A1    11/1990
CA    2075662 A1     2/1993
              (Continued)

OTHER PUBLICATIONS

Pacofsky et al, "Potent Dipeptide Inhibitors of the pp60 c=src domain," J. Med. Chem 1998, 41, pp. 1894-1908.
(Continued)

Primary Examiner — Adam Weidner
(74) Attorney, Agent, or Firm — McNeill Baur PLLC

(57) ABSTRACT

The present technology relates to compounds, kits, compositions, and methods useful for the treatment of numerous pathologies including dementia, Alzheimer's disease, Parkinson's disease, amyotrophic lateral sclerosis, and other neurodegenerative diseases, spinal cord injury, traumatic brain injury, diabetes and metabolic syndrome, defective wound healing, and/or sensorineural hearing and vision loss.

38 Claims, 2 Drawing Sheets

Stability of pro-drugs in Simulated Intestinal or Gastric Fluids

(56) References Cited

U.S. PATENT DOCUMENTS

| | | |
|---|---|---|
| 5,180,816 A | 1/1993 | Dean |
| 5,378,691 A | 1/1995 | Raddatz et al. |
| 5,382,569 A | 1/1995 | Cody et al. |
| 5,430,062 A | 7/1995 | Cushman et al. |
| 5,484,811 A | 1/1996 | Hanson et al. |
| 5,484,812 A | 1/1996 | Hanson et al. |
| 5,618,652 A | 4/1997 | Ueda et al. |
| 5,661,129 A | 8/1997 | Feelisch et al. |
| 5,686,419 A | 11/1997 | Powers et al. |
| 5,763,576 A | 6/1998 | Powers |
| 5,789,383 A | 8/1998 | Wirth et al. |
| 5,817,757 A | 10/1998 | Adams et al. |
| 5,831,004 A | 11/1998 | Campbell et al. |
| 5,840,698 A | 11/1998 | Campbell et al. |
| 5,854,388 A | 12/1998 | Harding et al. |
| 6,022,696 A | 2/2000 | Harding et al. |
| 6,121,489 A | 9/2000 | Dorner et al. |
| 6,242,563 B1 | 6/2001 | Dong et al. |
| 6,348,570 B1 | 2/2002 | Chapman et al. |
| 6,468,977 B1 | 10/2002 | Karimian et al. |
| 6,867,192 B1* | 3/2005 | Armour ............... C07C 271/40 514/19.1 |
| 7,118,747 B2 | 10/2006 | Harding et al. |
| 7,795,378 B2 | 9/2010 | Sharma et al. |
| 7,910,555 B2 | 3/2011 | Harding et al. |
| 7,981,862 B2 | 7/2011 | Zamora et al. |
| 8,236,761 B2 | 8/2012 | Harding et al. |
| 8,598,118 B2 | 12/2013 | Harding et al. |
| 9,051,351 B2 | 6/2015 | Harding et al. |
| 9,066,901 B2 | 6/2015 | Harding et al. |
| 9,150,613 B2 | 10/2015 | Harding et al. |
| 9,475,854 B2 | 10/2016 | Coffin et al. |
| 9,611,297 B1 | 4/2017 | Leger et al. |
| 9,765,099 B2 | 9/2017 | McMurray et al. |
| 9,877,898 B2 | 1/2018 | Moszner et al. |
| 9,962,388 B2 | 5/2018 | Ding et al. |
| 9,969,719 B2 | 5/2018 | Ding et al. |
| 10,385,080 B2 | 8/2019 | McMurray et al. |
| 10,526,320 B2 | 1/2020 | Yuan et al. |
| 2001/0046668 A1 | 11/2001 | Levine et al. |
| 2004/0001801 A1 | 1/2004 | Madison et al. |
| 2005/0118643 A1 | 6/2005 | Burgess et al. |
| 2005/0214859 A1 | 9/2005 | Dransfield et al. |
| 2005/0238993 A1 | 10/2005 | Watanabe et al. |
| 2006/0063803 A1 | 3/2006 | Ruggeri et al. |
| 2006/0172952 A1 | 8/2006 | Powers et al. |
| 2006/0233748 A1 | 10/2006 | Merzouk et al. |
| 2006/0241057 A1 | 10/2006 | Powers et al. |
| 2007/0116669 A1 | 5/2007 | Merzouk et al. |
| 2007/0117821 A1 | 5/2007 | Ding et al. |
| 2007/0160574 A1 | 7/2007 | Merzouk et al. |
| 2008/0293634 A1 | 11/2008 | Harding et al. |
| 2009/0270423 A1 | 1/2009 | Blackwell et al. |
| 2009/0048238 A1 | 2/2009 | Aebi et al. |
| 2009/0111152 A1 | 4/2009 | Sherman et al. |
| 2009/0186902 A1 | 7/2009 | Merla et al. |
| 2010/0228004 A1 | 9/2010 | Prabhakaran |
| 2013/0023475 A1 | 1/2013 | Harding et al. |
| 2013/0165392 A1 | 6/2013 | Harding et al. |
| 2014/0051633 A1 | 2/2014 | Harding et al. |
| 2014/0094413 A1* | 4/2014 | Harding ............ A61K 38/1833 514/17.7 |
| 2014/0162937 A1 | 6/2014 | Vaara et al. |
| 2015/0337024 A1* | 11/2015 | Coffin ................ C07K 5/0606 514/9.5 |
| 2015/0357204 A1 | 12/2015 | Ogihara et al. |
| 2016/0009763 A1 | 1/2016 | Lin et al. |
| 2016/0122386 A1 | 5/2016 | Wisniewski et al. |
| 2017/0022149 A1 | 1/2017 | Nguyen |
| 2017/0196830 A1 | 7/2017 | Shanahan et al. |
| 2018/0000897 A1 | 1/2018 | Rusanescu |
| 2018/0072717 A1 | 3/2018 | Liu et al. |
| 2018/0291063 A1 | 10/2018 | Cai et al. |
| 2018/0340008 A1 | 11/2018 | Bassiri et al. |

FOREIGN PATENT DOCUMENTS

| | | |
|---|---|---|
| CN | 102838523 A | 12/2012 |
| CN | 104788537 A | 7/2015 |
| CN | 108117582 A | 6/2018 |
| DE | 3320175 A1 | 12/1984 |
| DE | 3915361 A1 | 11/1990 |
| DE | 4122885 A1 | 1/1993 |
| DE | 4321306 A1 | 1/1995 |
| DE | 19914474 A1 | 10/1999 |
| EP | 0126974 A1 | 12/1984 |
| EP | 0163237 A2 | 12/1985 |
| EP | 0355065 A1 | 2/1990 |
| EP | 0393445 A2 | 10/1990 |
| EP | 0412350 A2 | 2/1991 |
| EP | 0443429 A1 | 8/1991 |
| EP | 0457195 A2 | 11/1991 |
| EP | 0497366 A2 | 8/1992 |
| EP | 0498940 A2 | 8/1992 |
| EP | 0519748 A2 | 12/1992 |
| EP | 0528487 A2 | 2/1993 |
| EP | 0547699 A1 | 6/1993 |
| EP | 0600832 A1 | 6/1994 |
| EP | 0661058 A1 | 7/1995 |
| EP | 0731107 A1 | 9/1996 |
| EP | 0987251 A1 | 3/2000 |
| EP | 1059302 A1 | 12/2000 |
| EP | 1867667 A1 | 12/2007 |
| EP | 1932852 A1 | 6/2008 |
| EP | 2746262 A1 | 6/2014 |
| EP | 3345917 A1 | 7/2018 |
| FR | 2778406 A1 | 11/1999 |
| GB | 2292149 A | 2/1996 |
| GB | 2324529 A | 10/1998 |
| JP | 05117169 A | 5/1993 |
| JP | 05178890 A | 7/1993 |
| JP | 06192199 A | 7/1994 |
| JP | 08262673 A | 10/1996 |
| JP | 2000250182 A | 9/2000 |
| JP | 2002145898 A | 5/2002 |
| JP | 2015151458 A | 8/2015 |
| WO | WO 87/04349 A1 | 7/1987 |
| WO | WO 90/05531 A1 | 5/1990 |
| WO | WO 92/13952 A1 | 8/1992 |
| WO | WO 92/20706 A1 | 11/1992 |
| WO | WO 92/21361 A1 | 12/1992 |
| WO | WO 93/12076 A1 | 6/1993 |
| WO | WO 93/14777 A1 | 8/1993 |
| WO | WO 93/16710 A1 | 9/1993 |
| WO | WO 93/23357 A1 | 11/1993 |
| WO | WO 94/000492 | 1/1994 |
| WO | WO 94/06451 A1 | 3/1994 |
| WO | WO 94/14817 A1 | 7/1994 |
| WO | WO 94/22491 A1 | 10/1994 |
| WO | WO 94/22906 A1 | 10/1994 |
| WO | WO 94/28012 A1 | 12/1994 |
| WO | WO 95/13289 A1 | 5/1995 |
| WO | WO 96/16079 A2 | 5/1996 |
| WO | WO 96/33209 A1 | 10/1996 |
| WO | WO 96/33268 A1 | 10/1996 |
| WO | WO 96/40204 A1 | 12/1996 |
| WO | WO 96/40738 A1 | 12/1996 |
| WO | WO 97/03093 A1 | 1/1997 |
| WO | WO 97/08193 A1 | 3/1997 |
| WO | WO 97/16410 A1 | 5/1997 |
| WO | WO 97/40071 A1 | 10/1997 |
| WO | WO 98/12214 A1 | 3/1998 |
| WO | WO 98/12219 A1 | 3/1998 |
| WO | WO 98/22496 A2 | 5/1998 |
| WO | WO 98/27094 A1 | 6/1998 |
| WO | WO 98/29435 A1 | 7/1998 |
| WO | WO 99/31052 A1 | 6/1999 |
| WO | WO 99/32509 A2 | 7/1999 |
| WO | WO 00/05260 A1 | 2/2000 |
| WO | WO 2001/025210 A2 | 4/2001 |
| WO | WO 2001/079263 A1 | 10/2001 |
| WO | WO 02/040016 A2 | 5/2002 |
| WO | WO 02/055543 A2 | 7/2002 |
| WO | WO 02/060432 A1 | 8/2002 |

(56) References Cited

FOREIGN PATENT DOCUMENTS

| | | |
|---|---|---|
| WO | WO 02/095007 A2 | 11/2002 |
| WO | WO 2003/053988 A2 | 7/2003 |
| WO | WO 2004/005270 A1 | 1/2004 |
| WO | WO 2004/005324 A2 | 1/2004 |
| WO | WO 2004/018644 A2 | 3/2004 |
| WO | WO 2004/099124 A2 | 11/2004 |
| WO | WO 2005/014623 A2 | 2/2005 |
| WO | WO 2005/039617 A1 | 5/2005 |
| WO | WO 2005/080353 A1 | 9/2005 |
| WO | WO 2005/105829 A2 | 11/2005 |
| WO | WO 2005/113580 A1 | 12/2005 |
| WO | WO 2006/061714 A2 | 6/2006 |
| WO | WO 2007/031343 A1 | 3/2007 |
| WO | WO 2007/047991 A1 | 4/2007 |
| WO | WO 2007/048642 A1 | 5/2007 |
| WO | WO 2007/070372 A2 | 6/2007 |
| WO | WO 2007/144195 A2 | 12/2007 |
| WO | WO 2007/144196 A2 | 12/2007 |
| WO | WO 2008/000512 A2 | 1/2008 |
| WO | WO 2008/000513 A2 | 1/2008 |
| WO | WO 2008/005531 A2 | 1/2008 |
| WO | WO 2008/68487 A1 | 6/2008 |
| WO | WO 2008/120098 A2 | 10/2008 |
| WO | WO 2009/003003 A2 | 12/2008 |
| WO | WO 2009/003861 A1 | 1/2009 |
| WO | WO 2009/099677 A2 | 8/2009 |
| WO | WO 2009/103652 A1 | 8/2009 |
| WO | WO 2009/105782 A1 | 8/2009 |
| WO | WO 2009/114950 A1 | 9/2009 |
| WO | WO 2010/014179 A1 | 2/2010 |
| WO | WO 2010/022171 A1 | 2/2010 |
| WO | WO 2010/039461 A2 | 4/2010 |
| WO | WO 2010/042212 A2 | 4/2010 |
| WO | WO 2010/080605 A1 | 7/2010 |
| WO | WO 2010/080609 A1 | 7/2010 |
| WO | WO 2010/138652 A1 | 12/2010 |
| WO | WO 2010/138659 A1 | 12/2010 |
| WO | WO 2010/138685 A1 | 12/2010 |
| WO | WO 2010/138695 A1 | 12/2010 |
| WO | WO 2010/138706 A1 | 12/2010 |
| WO | WO 2010/138758 A1 | 12/2010 |
| WO | WO 2010/151644 A2 | 12/2010 |
| WO | WO 2011/011303 A1 | 1/2011 |
| WO | WO 2011/038061 A2 | 3/2011 |
| WO | WO 2011/038066 A2 | 3/2011 |
| WO | WO 2011/075471 A2 | 6/2011 |
| WO | WO 2011/088345 A1 | 7/2011 |
| WO | WO 2012/020219 A2 | 2/2012 |
| WO | WO 2012/026988 A2 | 3/2012 |
| WO | WO 2012/032085 A1 | 3/2012 |
| WO | WO 2012/122420 A2 | 9/2012 |
| WO | WO 2012/122422 A2 | 9/2012 |
| WO | WO 2012/138599 A2 | 10/2012 |
| WO | WO 2013/001297 A1 | 1/2013 |
| WO | WO 2013/030569 A2 | 3/2013 |
| WO | WO 2013/063468 A1 | 5/2013 |
| WO | WO 2013/123456 A1 | 8/2013 |
| WO | WO 2013/128003 A1 | 9/2013 |
| WO | WO 2013/152298 A1 | 10/2013 |
| WO | WO 2013/170077 A2 | 11/2013 |
| WO | WO 2013/170113 A1 | 11/2013 |
| WO | WO 2013/170115 A1 | 11/2013 |
| WO | WO 2013/190520 A2 | 12/2013 |
| WO | WO 2014/049610 A1 | 4/2014 |
| WO | WO 2014/052766 A1 | 4/2014 |
| WO | WO 2014/067746 A1 | 5/2014 |
| WO | WO 2014/074789 A1 | 5/2014 |
| WO | WO 2014/091268 A1 | 6/2014 |
| WO | WO 2014/139008 A1 | 9/2014 |
| WO | WO 2014/143241 A1 | 9/2014 |
| WO | WO 2014/145090 A1 | 9/2014 |
| WO | WO 2014/182928 A2 | 11/2014 |
| WO | WO 2014/207556 A1 | 12/2014 |
| WO | WO 2015/023898 A1 | 2/2015 |
| WO | WO 2015/073769 A1 | 5/2015 |
| WO | WO 2015/091795 A1 | 6/2015 |
| WO | WO 2018/122419 A1 | 7/2015 |
| WO | WO 2015/124797 A1 | 8/2015 |
| WO | WO 2015/166348 A1 | 11/2015 |
| WO | WO 2016/001319 A1 | 1/2016 |
| WO | WO 2016/008946 A1 | 1/2016 |
| WO | WO 2016/023511 A1 | 2/2016 |
| WO | WO 2016/049174 A1 | 3/2016 |
| WO | WO 2016/097405 A1 | 6/2016 |
| WO | WO 2016/123576 A1 | 8/2016 |
| WO | WO 2016/141881 A1 | 9/2016 |
| WO | WO 2016/150576 A1 | 9/2016 |
| WO | WO 2016/178979 A1 | 11/2016 |
| WO | WO 2016/182898 A1 | 11/2016 |
| WO | WO 2017/005902 A1 | 1/2017 |
| WO | WO 2017/106643 A1 | 6/2017 |
| WO | WO 2017/129331 A1 | 8/2017 |
| WO | WO 2017/151587 A1 | 9/2017 |
| WO | WO 2017/151886 A1 | 9/2017 |
| WO | WO 2017/172881 A1 | 10/2017 |
| WO | WO 2017/181004 A1 | 10/2017 |
| WO | WO 2017/201433 A1 | 11/2017 |
| WO | WO 2017/210188 A1 | 12/2017 |
| WO | WO 2017/210489 A1 | 12/2017 |
| WO | WO 2017/217855 A1 | 12/2017 |
| WO | WO 2018/010656 A1 | 1/2018 |
| WO | WO 2018/014862 A1 | 1/2018 |
| WO | WO 2018/035615 A1 | 3/2018 |
| WO | WO 2018/035617 A1 | 3/2018 |
| WO | WO 2018/060216 A1 | 4/2018 |
| WO | WO 2018/136646 A1 | 7/2018 |
| WO | WO 2018/152633 A1 | 8/2018 |
| WO | WO 2018/174831 A1 | 9/2018 |

OTHER PUBLICATIONS

International Search Report and Written Opinion for International Application No. PCT/US2017/035547 dated Oct. 18, 2017, 11 pages.

Zhang et al, "Structural analysis of angiotensin IV receptor (AT4) from selected bovine tissues," Journal of Pharmacology and Experimental Therapeutics (1999), 289(2), pp. 1075-1083.

McCoy et al., "Evaluation of Metabolically Stabilized Angiotensin IV Analogs as Procognitive/Antidementia Agents," Journal of Pharmacology and Experimental Therapeutics (Jan. 31, 2013), 344(1), pp. 141-154.

"Pubchem CID 18232021" Create Date: Dec. 4, 2007 (Dec. 4, 2007), Date Accessed: Sep. 19, 2017 (Sep. 19, 2017), Available at https://pubchem.ncbi.nlm.nih.gov/compound/18232021 (10 pages).

Ghosh et al., "Organic Carbamates in Drug Design and Medicinal Chemistry," *Journal of Medicinal Chemistry* 58: 2895-2940, 2015.

Deborah Heyl, et al., "Peptide Inhibitors of a-Amylase Based on Tendamistat: Development of Analogues with [pi]-Amino Acids Linking Critical Binding Segments", Protein and Peptide Letters: International Journal for Rapid Publication of Short Papers in Protein and Peptide Science, vol. 12, No. 3, Apr. 1, 2005 (Apr. 1, 2005), pp. 275-280, XP55649610, NL, ISSN: 0929-8665, DOI: 10.2174/0929866053587110.

European Search Report corresponding to European Patent Application No. 17807519.8, dated Jan. 10, 2020, 7 pages.

Jin-Mi Noh, et al., "Kojic acid-tripeptide amide as a new tyrosinase inhibitor", Biopolymers, vol. 88, No. 2, Jan. 1, 2007 (Jan. 1, 2007), pp. 300-307, XP55649603, US ISSN: 0006-3525, DOI: 10.1002/bip.20670.

\* cited by examiner

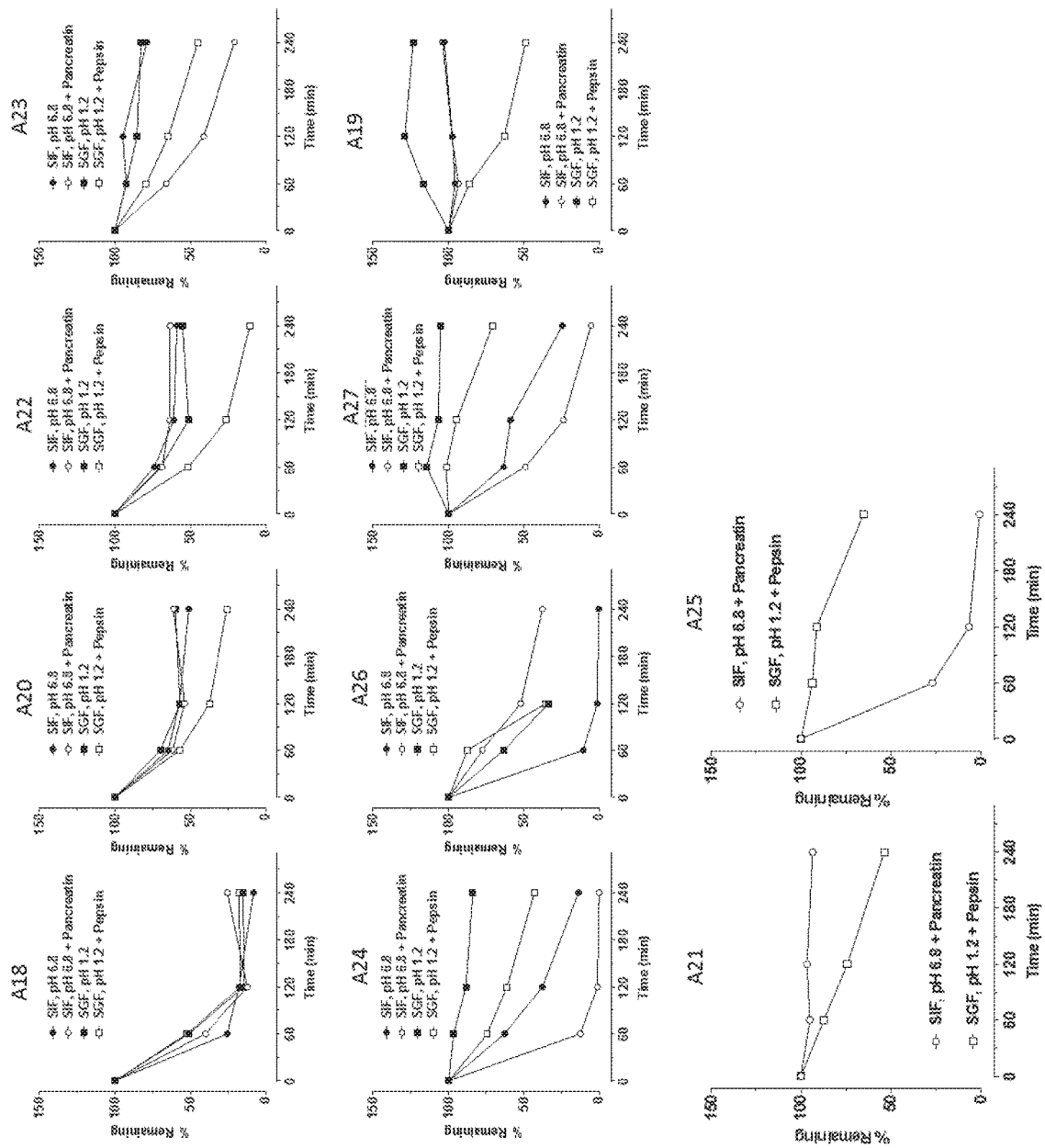
FIG 1. Stability of pro-drugs in Simulated Intestinal or Gastric Fluids

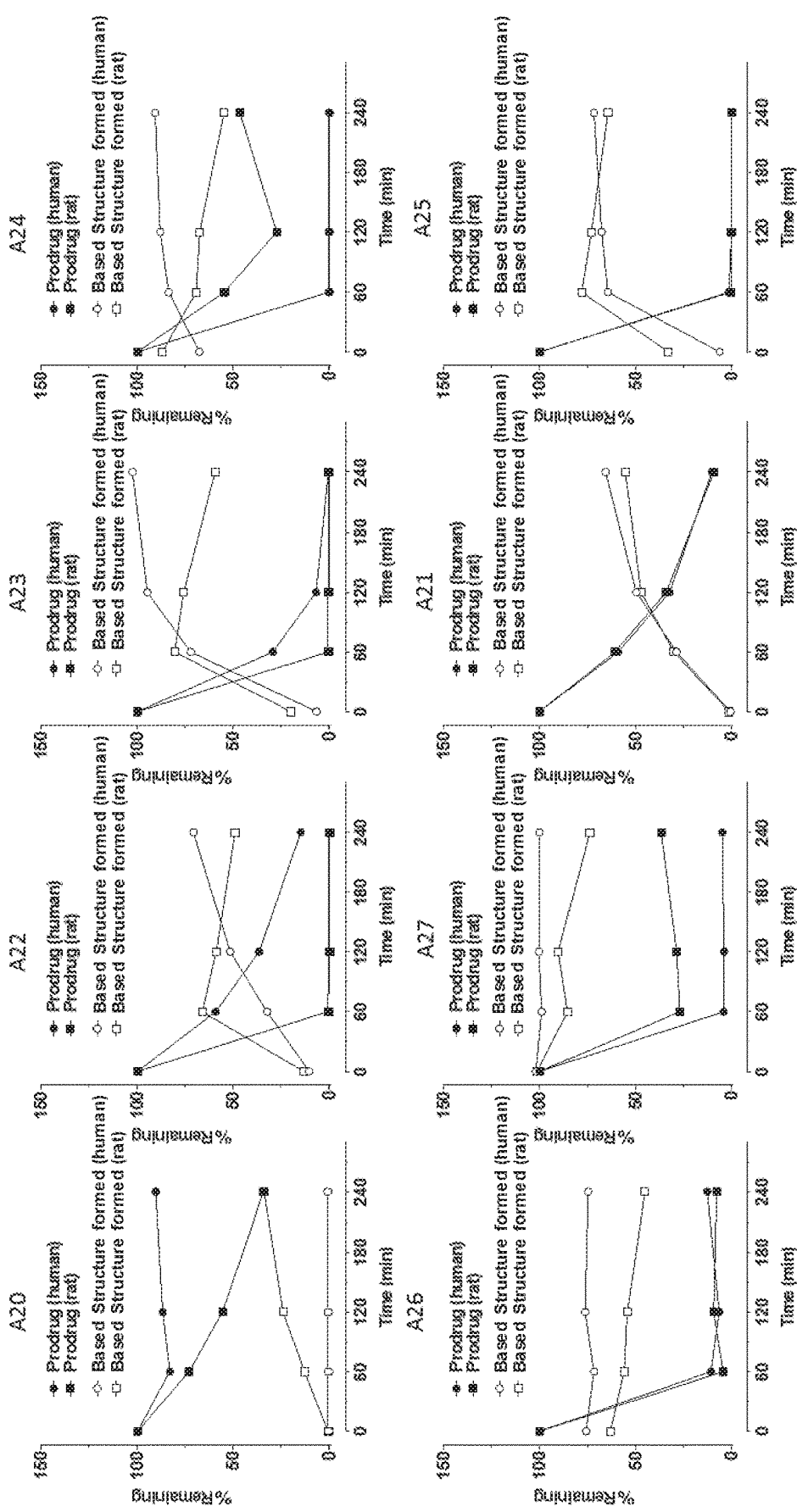
FIG 2. Formation of active pro-drugs

COMPOUNDS

1. CROSS REFERENCE TO RELATED APPLICATIONS

This application claims the benefit of U.S. Provisional Application No. 62/344,305, filed Jun. 1, 2016, which is hereby incorporated in its entirety by reference.

2. BACKGROUND

The small molecule peptidic compound, N-hexanoic-L-tyrosine-L-isoleucine-(6)-aminohexanoic amide ("Base Structure"), has been shown or predicted to have potential as a neuroprotective/neuroregenerative agent, to protect from or reverse neurodegenerative disease, to prevent or reverse the symptoms of dementia, to facilitate repair of traumatic injury to the nervous system, and to enhance cognitive function. Given Base Structure's therapeutic potential to treat Alzheimer's disease, Parkinson's disease, amyotrophic lateral sclerosis, other dementias and neurodegenerative diseases, spinal cord injury, traumatic brain injury, and sensorineural hearing and vision loss, there is a need in the art for compounds that retain Base Structure's therapeutic activities while possessing optimized pharmacokinetic and pharmacodynamic properties.

3. SUMMARY

Compounds have been synthesized that demonstrate increased stability in simulated intestinal fluid and simulated gastric fluid, but that can be hydrolyzed in plasma to produce Base Structure or Base Structure-like compounds that retain Base Structure's beneficial properties.

Accordingly, in a first aspect, compounds are provided.

In typical embodiments, the compounds possess a di-amino acid core structure and are substituted by one or more organic functional groups at the C-terminus, N-terminus, and/or the side-chain of the core.

In some embodiments, the compound is a compound of formula I:

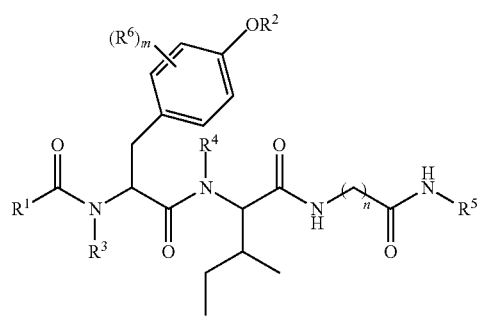

(I)

wherein:
n is 1, 2, 3, 4, 5, 6, 7, 8, or 9;
m is 0, 1, 2, 3, or 4;
$R^1$ is selected from the group consisting of: amino, substituted amino, alkoxy, substituted alkoxy, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, $C_1$-$C_{12}$ substituted alkynyl, $C_1$-$C_6$ alkyl aryl, $C_1$-$C_6$ substituted alkyl aryl, $C_1$-$C_6$ alkenyl aryl, $C_1$-$C_6$ substituted alkenyl aryl, $C_1$-$C_6$ alkynyl aryl, $C_1$-$C_6$ substituted alkynyl aryl, norleucine, tyrosine, phenylalanine, aspartic acid, arginine, isoleucine, serine, threonine, histidine, glycine, cysteine, methionine, tryptophan, lysine norvaline, norleucine, ornithine, S-benzyl cysteine, O-benzyl serine, O-benzyl threonine, cyclohexylalanine, 4-tetrahydropyranyl-glycine, and azaleucine;

$R^2$ is selected from the group consisting of: hydrogen, —CH($R^a$)OPO(OH)$_2$, —CO—Y, ⵟ-PO(OY)$_2$, ⵟ-PO(OH)$_2$, —C(=O)—Y, —CO—U, —C(=O)—(CH$_2$)$_r$U, and —CH$_2$—V, where $R^a$ is hydrogen or CH$_3$, where Y is —Z—(CH$_2$)$_q$—W—$R^b$, q is 0-4, where Z and W are independently selected from the group consisting of: CH$_2$, O, S, NR$^c$ and R$^b$, where $R^c$ is selected from the group consisting of: hydrogen, $C_1$-$C_4$ alkyl, and $C_3$-$C_6$ cycloalkyl, $R^b$ is selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, $C_1$-$C_{12}$ substituted alkynyl, $C_3$-$C_8$ cycloalkyl, $C_3$-$C_8$ substituted cycloalkyl, $C_6$-$C_{10}$ aryl, $C_6$-$C_{10}$ substituted aryl, $C_3$-$C_8$ heterocycloalkyl, $C_3$-$C_8$ substituted heterocycloalkyl, $C_4$-$C_{10}$ heteroaryl, and $C_4$-$C_{10}$ substituted heteroaryl, where r is 0-5, U is selected from aryl, heteroaryl or heterocycloalkyl, where V is —O—C(=O)-Q-(CH$_2$)$_r$—$R^d$, where Q is selected from the group consisting of: a bond, O, and N($R^c$), where $R^d$ is selected from the group consisting of: $C_6$-$C_{10}$ aryl, $C_4$-$C_{10}$ heteroaryl, $C_3$-$C_8$ heterocycloalkyl, a hexose, a pentose, and -(5-methyl-2-oxo-1,3-dioxol-4-yl)methyl), or alternatively —C(=O)—Y forms an amide bond thru a nitrogen atom on Y in which case Y is a selected from the group consisting of: glycine, sarcosine, N,N-dimethyl glycine, alanine, valine, leucine, isoleucine, lysine, ornithine, arigine, serine, and theronine;

$R^3$ and $R^4$ are independently selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, $C_1$-$C_{12}$ substituted alkynyl, $C_3$-$C_8$ cycloalkyl, $C_3$-$C_8$ substituted cycloalkyl, $C_6$-$C_{10}$ aryl, $C_6$-$C_{10}$ substituted aryl, $C_3$-$C_8$ heterocycloalkyl, $C_3$-$C_8$ substituted heterocycloalkyl, $C_4$-$C_{10}$ heteroaryl, $C_4$-$C_{10}$ substituted heteroaryl, ⵟ-CH($R^a$)OPO(OY)$_2$, ⵟ-CH($R^a$)OPO(OY)(OH) and ⵟ-CH($R^a$)OPO$_3$H$_2$, or optionally $R^3$ and $R^4$ together are bonded to form a fused bicyclic ring system or a spirocyclic ring system;

$R^5$ is selected from the group consisting of: hydrogen, ⵟ-CH$_2$—O—CO—Y, and ⵟ-CH($R^a$)—O—PO$_3$H$_2$;

each $R^6$ is independently selected from the group consisting of: hydrogen, deuterium, CH$_3$, F, $^{19}$F, and $^{18}$F;

wherein optionally Z and W are taken together to form a $C_3$-$C_8$ heterocycloalkyl or $C_4$-$C_{10}$ heteroaryl or fused bicyclic ring system in which one of the rings is a $C_4$-$C_{10}$ heteroaryl;

and wherein the amino acid of $R^1$, if present, is covalently bonded either thru the nitrogen atom of the N-terminus of the amino acid to the carbon atom of the C(=O) in

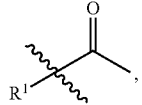

or a carbon atom of the amino acid of $R^1$ is bonded to the C(=O) such that

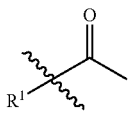

taken together represents amino acid where the C(=O) of

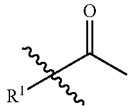

is the carboxy-terminus of the amino acid;

and wherein any and all heterocyclic and heteroaryl rings contain up to four heteroatoms selected from the group consisting of: O, N, and S;

with the proviso that when both Z and W are heteroatoms, the value of q cannot be 1;

and with the proviso that when both $R^2$ and $R^5$ are hydrogen and n is 5, at least one of the $R^3$ or $R^4$ groups is not hydrogen;

or a tautomer and/or a pharmaceutically acceptable salt thereof.

In various embodiments, the compound is selected from among certain specific compounds disclosed herein.

In another aspect, compositions comprising at least one of the compounds described herein are provided.

In a further aspect, pharmaceutical compositions comprising at least one of the compounds described herein are provided.

In a still further aspect, methods of treatment are provided.

The methods comprise administering at least one compound as described herein to a subject in an amount effective to treat, protect from, or reverse neurodegenerative disease, to prevent or reverse the symptoms of dementia, to facilitate repair of traumatic injury to the nervous system, or to enhance cognitive function. In various embodiments, the subject has a disease selected from Alzheimer's disease, Parkinson's disease, amyotrophic lateral sclerosis, other dementias and neurodegenerative diseases, spinal cord injury, traumatic brain injury, and/or sensorineural hearing loss. In typical embodiments, the method comprises administering a pharmaceutical composition comprising at least one of the compounds described herein, as described herein.

In various embodiments, the compound is administered as the sole medical treatment. In various embodiments, the compound is administered in combination with other medical and/or surgical interventions according to the prevailing standards of care.

These and other embodiments are described in further detail herein.

4. BRIEF DESCRIPTION OF THE DRAWINGS

These and other features, aspects, and advantages of the present invention will become better understood with regard to the following description, and accompanying drawings, where:

FIG. 1 are graphs containing data from experiments testing stability of various compounds synthesized as potential prodrugs of Base Structure in the presence of Simulated Intestinal Fluid (SIP), pH 6.8 (+/−Pancreatin) or Simulated Gastric Fluid (SGF), pH 1.2 (+/−Pepsin). The results demonstrate increased stability of some prodrugs even in the presence of enzymes native to either intestinal or gastric fluids over 240 minutes.

FIG. 2 are graphs showing data measuring the formation of Base Structure from various prodrugs in both human and rat plasma over 240 minutes, measured both as percent prodrug compound remaining (left y-axis).

5. DETAILED DESCRIPTION

5.1. Definitions

Various terms used in the specification and claims herein are defined as set forth below, unless otherwise specifically defined in this disclosure. All technical and scientific terms not defined herein have the meaning commonly understood by a person skilled in the art to which this invention belongs.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). $C_x$ alkyl refers to an alkyl group having x number of carbon atoms.

"Alkenyl" refers to straight or branched hydrocarbyl groups having from 1 to 6 carbon atoms and preferably 2 to 4 carbon atoms and having at least 1 and preferably from 1 to 2 sites of unsaturation (>C=C<). Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

In some embodiments, the substituted alkyl groups include halogenated alkyl groups and particularly halogenated methyl groups such as trifluoromethyl, difluoromethyl, fluoromethyl and the like.

"Alkyl aryl" refers to an alkyl group having from 1 to 8, preferably 1 to 5, or more preferably 1 to 3 carbon atoms in length and is substituted specifically at any one of the carbons along the chain with an aryl group. "Alkenyl aryl" refers to an alkenyl or alkene group having from 1 to 8, preferably 1 to 5, or more preferably 1 to 3 carbon atoms in length and is substituted specifically at any one of the carbons along the chain with an aryl group. The aryl group can include heteroatoms or not. "Alkynyl aryl" refers to an alkynyl or alkyne group having from 1 to 8, preferably 1 to 5, or more preferably 1 to 3 carbon atoms in length and is substituted specifically at any one of the carbons along the chain with an aryl group. The aryl group can include heteroatoms or not.

"Cycloalkyl" or "Cyclyl alkyl" refers to a saturated or partially saturated, but not aromatic, group having from 3 to 10 ring carbon atoms and no heteroatoms. Cycloalkyl encompasses single ring systems.

"Substituted alkenyl" refers to alkenyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Ar" and/or "aryl" refers to any group which is aromatic. This group must be cyclic; and does not contain heteroatoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(O)—.

"Acylamino" refers to the groups —NR$^{30}$C(O)alkyl, —NR$^{30}$C(O)substituted alkyl, —NR$^{30}$C(O)cycloalkyl, —NR$^{30}$C(O)substituted cycloalkyl, —NR$^{30}$C(O)alkenyl, —NR$^{30}$C(O)substituted alkenyl, alkoxy, substituted alkoxy-NR$^{30}$C(O)alkynyl, —NR$^{30}$C(O)substituted alkynyl, —NR$^{30}$C(O)aryl, —NR$^{30}$C(O)substituted aryl, —NR$^{30}$C(O)heteroaryl, —NR$^{30}$C(O)substituted heteroaryl, —NR$^{30}$C(O)heterocyclic, and —NR$^{30}$C(O)substituted heterocyclic wherein R$^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the groups H—C(N)—, alkyl-C(N)—, substituted alkyl-C(N)—, alkenyl-C(N)—, substituted alkenyl-C(N)—, alkynyl-C(N)—, substituted alkynyl-C(N)—, cycloalkyl-C(N)—, substituted cycloalkyl-C(N)—, aryl-C(N)—, substituted aryl-C(N)—, heteroaryl-C(N)—, substituted heteroaryl-C(N)—, heterocyclic-C(N)—, and substituted heterocyclic-C(N)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR$^{31}$R$^{32}$ where R$^{31}$ and R$^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —C(O)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl carbonyloxy" refers to the group —C(NR$^{33}$)OR$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{30}$C(O)NR$^{33}$R$^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{30}$C(S)NR$^{33}$R$^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where R$^{30}$ is hydrogen or alkyl and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocylyloxy, substituted heterocyclyloxy, heterocyclylthio, substituted heterocyclylthio, nitro, SO$_3$H, substituted sulfonyl, sulfonyloxy, thioacyl, thiol, alkylthio, a monosaccharide (which may be covalently bonded to the aryl group thru any oxygen atom on the saccharide), and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Ethylene glycol" refers to the group —O—CH2CH2-O-E, wherein E is either H or CH3.

"Guanidino" refers to the group —NHC(=NH)NH₂.

"Substituted guanidino" refers to —NR³⁶C(=NR³⁶)N (R³⁶)₂ where each R³⁶ is independently selected from the group consisting of hydrogen, alkyl, substituted alkyl, aryl, substituted aryl, heteroaryl, substituted heteroaryl, heterocyclic, and substituted heterocyclic and two R³⁶ groups attached to a common guanidino nitrogen atom are optionally joined together with the nitrogen bound thereto to form a heterocyclic or substituted heterocyclic group, provided that at least one R³⁶ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 4 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 2 to 10 ring carbon atoms and from 1 to 4 ring heteroatoms selected from the group consisting of nitrogen, sulfur, or oxygen. $C_x$ cycloalkyl or heterocycloalkyl refers to a group having x number of ring carbon atoms excluding the ring heteroatoms. Heterocycle encompasses single ring or multiple condensed rings, including fused, bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, dexahydroindole, dihydropyridine, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, imidazolinone, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO₂.

"Oxo" refers to the atom (=O) or (—O⁻).

"Phthalimido" refers to the group

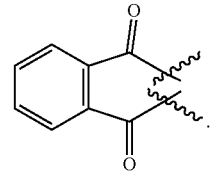 [SMILES: *C(=O)c1ccccc1C(*)=O]

Phthalimide functional groups are well known in the art and can be generated by covalently bonding a nitrogen atom to a C₆H₄(CO)₂ group.

"Polyethylene glycol" refers to the group —O—(CH₂CH₂—O)ₙ-E, wherein E is either H or CH₃, where n is between 2-20,000.

"Spirocyclic ring system" refers to a ring system with two rings that has a single ring carbon atom in common to both rings. Herein used the term bicyclic can incorporate up to four heteroatoms in either ring.

"Bicyclic ring" or "Bicyclic ring system" refers to a ring system with two rings that has two ring carbon atoms in common, and which can located at any position along either ring. Herein used the term bicyclic ring system can incorporate up to four heteroatoms in either ring.

"Sulfinyl" refers to the divalent group —SO—.

"Sulfonyl" refers to the divalent group —S(O)₂—.

"Substituted sulfonyl" refers to the group —SO₂-alkyl, —SO₂-substituted alkyl, —SO₂—OH, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO₂—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group-OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substitution" or "substitution" or "substituted" generally refers groups which are covalently bonded to an atom to replace a hydrogen atom. The atom in this general context can be a carbon atom or a heteroatom, for example a nitrogen atom.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Tautomer" refers to alternate forms of a compound that differ in the position of a proton, such as enol-keto and imine-enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluoromethyl, fluoromethyl and the like.

The term "ameliorating" refers to any therapeutically beneficial result in the treatment of a disease state, e.g., an inflammatory disease state, including lessening in the severity or progression, remission, or cure thereof. In some embodiments, "ameliorating" includes prophylaxis of a disease state.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can, in some embodiments, be a "prophylactically effective amount" as prophylaxis can be considered therapy.

"Subject" refers to a mammalian organism treated using a compound of the present invention. The "subject" can be a human or non-human mammalian organism.

"Treating" or "treatment" of a disease or disorder in a subject refers to 1) preventing the disease or disorder from occurring in a subject that is predisposed or does not yet display symptoms of the disease or disorder; 2) binding the disease or disorder or arresting its development; or 3) ameliorating or alleviating the cause of the regression of the disease or disorder.

As used herein, an agent is said to be "specific" if it reacts or associates more frequently, more rapidly, with greater duration and/or with greater affinity with a specified target than it does with alternative substances, especially as compared to substances that are structurally related to the target, e.g., an isoform of the target. In some embodiments, an agent is "specific" for a target if a concentration of the agent that produces a maximal effect in an in vitro or in vivo target assay (e.g., a binding assay or an enzyme activity assay) produces no measurable effect in a comparable assay carried out using another substance, especially one or more substances that are structurally related to the target.

As used herein, the term "contacting," as used herein, includes both directly contacting cells, for example, in vivo, in vitro, or ex vivo, or indirectly contacting cells, such as, for example, by administering an agent to a subject. Further, "contacting" a cell with an agent includes administering or applying a prodrug version of the agent.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

5.2. Additional Interpretational Conventions

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}$C, $^{32}$P and $^{35}$S are thus within the scope of the present technology. Procedures for inserting such labels into the compounds of the present technology will be readily apparent to those skilled in the art based on the disclosure herein.

Unless the specific stereochemistry is expressly indicated, all chiral, diastereomeric, and racemic forms of a compound are intended. Thus, compounds described herein include enriched or resolved optical isomers at any or all asymmetric atoms as are apparent from the depictions. Racemic mixtures, and d or l enriched stereomeric mixtures, as well as the individual optical isomers can be isolated or synthesized so as to be substantially free of their enantiomeric or diastereomeric partners, and these stereoisomers are all within the scope of the present technology.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

Herein any substituted functional group is substituted at from one to three different positions, and those one to three substituting groups are capable of each independently being substituted at one to three positions, wherein any and each substituting group is independently selected from the group consisting of: halogen, hydroxyl, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, acyl, acylamino, aminocarbonylamino, aminoacyl, acyloxy, amino, substituted amino, aminocarbonyl, aminothiocarbonyl, aminoacyl carbonyloxy, aminocarbonylamino, aminothiocarbonylamino, aminocarbonyloxy, aminosulfonyl, aminosulfonyloxy, aminosulfonylamino, amidino, $C_1$-$C_8$ alkoxy, substituted $C_1$-$C_8$ alkoxy, $C_3$-$C_7$ aryl, substituted $C_3$-$C_7$ aryl, $C_3$-$C_7$ aryloxy, substituted $C_3$-$C_7$ aryloxy, $C_3$-$C_7$ arylthio, substituted $C_3$-$C_7$ arylthio, carboxyl, carboxyl ester, (carboxyl ester)amino, (carboxyl ester)oxy, $C_3$-$C_{10}$ cycloalkyl, substituted $C_3$-$C_{10}$ cycloalkyl, $C_3$-$C_7$ heterocycloalkyl, guanidino, substituted guanidino, $C_3$-$C_7$ heteroaryloxy, $C_3$-$C_7$ substituted heteroaryloxy, $C_3$-$C_7$ heteroarylthio, $C_3$-$C_7$ substituted heteroarylthio, sulfonyl, substituted sulfonyl, sulfinyl, substituted sulfinyl, sulfonyloxy, substituted sulfonyloxy, thioacyl, alkylthio, substituted alkylthio, $C_3$-$C_7$ heteroaryl, and substituted $C_3$-$C_7$ heteroaryl.

Herein any and all heteroaryl and heterocycloalkyl substituents may contain up to four heteroatoms selected from the group consisting of: O, N, and S but may not contain a heteroatom-heteroatom bond such as: O—O, O—S, N—S, N—O and S—S bonds are not covered. It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be substituted one more time (at from one to three positions).

It is understood that the definitions presented herein are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

5.3. Compounds

In a first aspect, compounds are provided that demonstrate improved drug characteristics and enhanced solubility properties, improved DMPK properties demonstrated by increased stability in simulated intestinal fluid and simulated gastric fluid, but that can be hydrolyzed in plasma to produce Base Structure, or to produce Base Structure-like compounds that retain Base Structure's therapeutic activity, are provided.

In typical embodiments, the compounds possess a di-amino acid core structure and are substituted by one or more organic functional groups at the C-terminus, N-terminus, and/or the side-chain of the core.

In some embodiments, the compound is a compound of formula II:

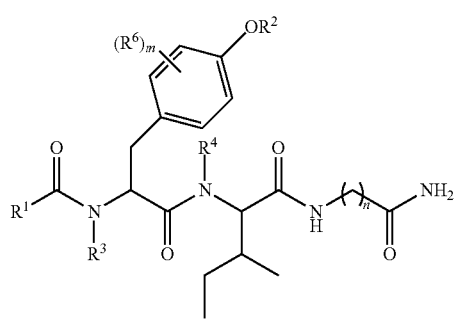

wherein:
n is 1, 2, 3, 4, 5, 6, 7, 8, or 9;
m is 0, 1, 2, 3, or 4;
$R^1$ is selected from the group consisting of: $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, and $C_1$-$C_{12}$ substituted alkynyl;
$R^2$ is selected from the group consisting of: hydrogen, ⸻PO(OY)$_2$, ⸻PO(OH)$_2$, —C(=O)—Y and —CO—U, where Y is —Z—(CH$_2$)$_q$—W—$R^b$, q is 0-4, where Z and W are independently selected from the group consisting of: CH$_2$, O, S, NR$^c$ and R$^b$, where R$^c$ is selected from the group consisting of: hydrogen, $C_1$-$C_4$ alkyl, and $C_3$-$C_6$ cycloalkyl, R$^b$ is selected from the group consisting of: hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl, or alternatively —C(=O)—Y forms an amide bond thru a nitrogen atom on Y in which case Y is a selected from the group consisting of: glycine, sarcosine, N,N-dimethyl glycine, alanine, valine, leucine, isoleucine, lysine, ornithine, arigine, serine, and theronine and where U is selected from the group consisting of: pyridine, 1,4-dihydropyridine, N-alkyl-1,4-dihydropyridine, and C-imidazole or U is selected from aryl, heteroaryl or heterocycloalkyl;
$R^3$ and $R^4$ are independently selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, and $C_1$-$C_{12}$ substituted alkynyl, or optionally $R^3$ and $R^4$ together are bonded to form a fused bicyclic ring system or a spirocyclic ring system;
each $R^6$ is independently selected from the group consisting of: hydrogen, deuterium, CH$_3$, F, $^{19}$F, and $^{18}$F;
wherein optionally Z and W are taken together to form a $C_3$-$C_8$ heterocycloalkyl or $C_4$-$C_{10}$ heteroaryl or bicyclic ring system in which one of the rings must be a $C_4$-$C_{10}$ heteroaryl;

and wherein any and all heterocyclic and heteroaryl rings contain up to four heteroatoms selected from the group consisting of: O, N, and S;
with the proviso that when both Z and W are heteroatoms, the value of q cannot be 1;
and with the proviso that when $R^2$ is hydrogen, at least one of the $R^3$ or $R^4$ groups is not hydrogen;
or a tautomer and/or a pharmaceutically acceptable salt thereof.

In some embodiments, the compound is a compound of formula III:

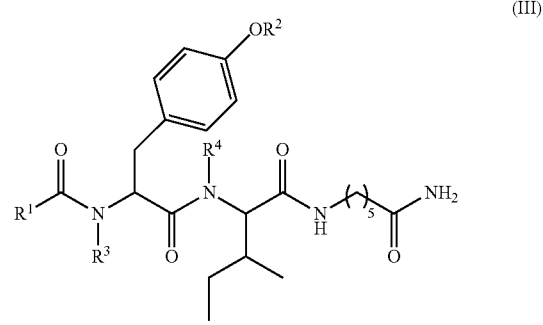

wherein:
$R^1$ is a $C_1$-$C_{12}$ alkyl or $C_1$-$C_{12}$ substituted alkyl;
$R^2$ is selected from the group consisting of: hydrogen, ⸻PO(OY)$_2$, ⸻PO(OH)$_2$, and —C(=O)—Y, where Y is —Z—(CH$_2$)$_q$—W—$R^b$, q is 0-4, where Z and W are independently selected from the group consisting of: CH$_2$, O, S, NR$^c$ and R$^b$, where R$^c$ is selected from the group consisting of: hydrogen, $C_1$-$C_4$ alkyl, and $C_3$-$C_6$ cycloalkyl, R$^b$ is selected from the group consisting of: hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_5$ heterocycloalkyl, and $C_3$-$C_5$ substituted heterocycloalkyl;
$R^3$ and $R^4$ are independently selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, and $C_1$-$C_{12}$ substituted alkynyl, or optionally $R^3$ and $R^4$ together are bonded to form a fused bicyclic ring system or a spirocyclic ring system, where the fused ring is a $C_3$-$C_8$ heterocycloalkyl or $C_6$-$C_{10}$ aryl or $C_4$-$C_{10}$ heteroaryl;
wherein optionally Z and W are taken together to form a $C_3$-$C_8$ heterocycloalkyl or $C_4$-$C_{10}$ heteroaryl or bicyclic ring system in which one of the rings must be a $C_4$-$C_{10}$ heteroaryl;
and wherein any and all heterocyclic and heteroaryl rings contain up to four heteroatoms selected from the group consisting of: O, N, and S;
with the proviso that when both Z and W are heteroatoms, the value of q cannot be 1;
and with the proviso that when $R^2$ is hydrogen, at least one of the $R^3$ or $R^4$ groups is not hydrogen;
or a tautomer and/or a pharmaceutically acceptable salt thereof.

In some embodiments, the compound is a compound of formula IV:

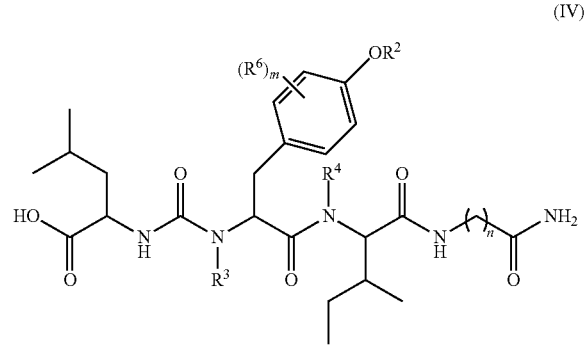

(IV)

wherein:

n is 1, 2, 3, 4, 5, 6, 7, 8, or 9;

m is 0, 1, 2, 3, or 4;

$R^2$ is selected from the group consisting of: hydrogen, —CH($R^a$)OPO(OH)$_2$, —CO—Y, ⁃PO(OY)$_2$, ⁃PO(OH)$_2$, —C(=O)—Y, —CO—U, —C(=O)—(CH$_2$)$_r$U, and —CH$_2$—V, where $R^a$ is hydrogen or CH$_3$, where Y is —Z—(CH$_2$)$_q$—W—$R^b$, q is 0-4, where Z and W are independently selected from the group consisting of: CH$_2$, O, S, NR$^c$ and $R^b$, where $R^c$ is selected from the group consisting of: hydrogen, C$_1$-C$_4$ alkyl, and C$_3$-C$_6$ cycloalkyl, $R^b$ is selected from the group consisting of: hydrogen, C$_1$-C$_{12}$ alkyl, C$_1$-C$_{12}$ substituted alkyl, C$_1$-C$_{12}$ alkenyl, C$_1$-C$_{12}$ substituted alkenyl, C$_1$-C$_{12}$ alkynyl, C$_1$-C$_{12}$ substituted alkynyl, C$_3$-C$_8$ cycloalkyl, C$_3$-C$_8$ substituted cycloalkyl, C$_6$-C$_{10}$ aryl, C$_6$-C$_{10}$ substituted aryl, C$_3$-C$_8$ heterocycloalkyl, C$_3$-C$_8$ substituted heterocycloalkyl, C$_4$-C$_{10}$ heteroaryl, and C$_4$-C$_{10}$ substituted heteroaryl, where r is 0-5, U is selected from aryl, heteroaryl or heterocycloalkyl, where V is —O—C(=O)-Q-(CH$_2$)$_r$—$R^d$, where Q is selected from the group consisting of: a bond, O, and N($R^c$), where $R^d$ is selected from the group consisting of: C$_6$-C$_{10}$ aryl, C$_4$-C$_{10}$ heteroaryl, C$_3$-C$_8$ heterocycloalkyl, a hexose, a pentose, and -(5-methyl-2-oxo-1,3-dioxol-4-yl)methyl), or alternatively —C(=O)—Y forms an amide bond thru a nitrogen atom on Y in which case Y is a selected from the group consisting of: glycine, sarcosine, N,N-dimethyl glycine, alanine, valine, leucine, isoleucine, lysine, ornithine, arigine, serine, and theronine;

$R^3$ and $R^4$ are independently selected from the group consisting of: hydrogen, C$_1$-C$_{12}$ alkyl, C$_1$-C$_{12}$ substituted alkyl, C$_1$-C$_{12}$ alkenyl, C$_1$-C$_{12}$ substituted alkenyl, C$_1$-C$_{12}$ alkynyl, and C$_1$-C$_{12}$ substituted alkynyl, or optionally $R^3$ and $R^4$ together are bonded to form a fused bicyclic ring system or a spirocyclic ring system;

each $R^6$ is independently selected from the group consisting of: hydrogen, deuterium, CH$_3$, F, $^{19}$F, and $^{18}$F;

wherein optionally Z and W are taken together to form a C$_3$-C$_8$ heterocycloalkyl or C$_4$-C$_{10}$ heteroaryl or bicyclic ring system in which one of the rings must be a C$_4$-C$_{10}$ heteroaryl;

and wherein any and all heterocyclic and heteroaryl rings contain up to four heteroatoms selected from the group consisting of: O, N, and S;

with the proviso that when both Z and W are heteroatoms, the value of q cannot be 1;

and with the proviso that when $R^2$ is hydrogen, at least one of the $R^3$ or $R^4$ groups is not hydrogen;

or a tautomer and/or a pharmaceutically acceptable salt thereof.

In some embodiments, the compound is a compound of formula V:

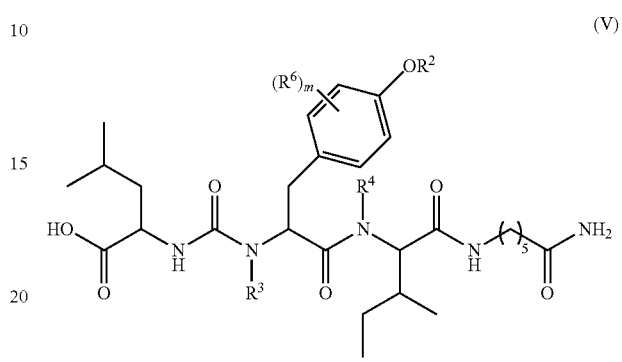

(V)

wherein:

m is 0, 1, 2, 3, or 4;

$R^2$ is selected from the group consisting of: hydrogen, ⁃PO(OY)$_2$, ⁃PO(OH)$_2$, and —C(=O)—Y, where Y is —Z—(CH$_2$)$_q$—W—$R^b$, q is 0-4, where Z and W are independently selected from the group consisting of: CH$_2$, O, S, NR$^c$ and $R^b$, where $R^c$ is selected from the group consisting of: hydrogen, C$_1$-C$_4$ alkyl, and C$_3$-C$_6$ cycloalkyl, $R^b$ is selected from the group consisting of: hydrogen, C$_1$-C$_{12}$ alkyl, C$_1$-C$_{12}$ substituted alkyl, C$_3$-C$_8$ cycloalkyl, C$_3$-C$_8$ substituted cycloalkyl, C$_3$-C$_8$ heterocycloalkyl, and C$_3$-C$_8$ substituted heterocycloalkyl, or alternatively —C(=O)—Y forms an amide bond thru a nitrogen atom on Y in which case Y is a selected from the group consisting of: glycine, sarcosine, N,N-dimethyl glycine, alanine, valine, leucine, isoleucine, lysine, ornithine, arigine, serine, and theronine;

$R^3$ and $R^4$ are independently selected from the group consisting of: hydrogen, C$_1$-C$_{12}$ alkyl, C$_1$-C$_{12}$ substituted alkyl, C$_1$-C$_{12}$ alkenyl, C$_1$-C$_{12}$ substituted alkenyl, C$_1$-C$_{12}$ alkynyl, and C$_1$-C$_{12}$ substituted alkynyl, or optionally $R^3$ and $R^4$ together are bonded to form a fused bicyclic ring system or a spirocyclic ring system, where the fused ring is a C$_3$-C$_8$ heterocycloalkyl or C$_6$-C$_{10}$ aryl or C$_4$-C$_{10}$ heteroaryl;

each $R^6$ is independently selected from the group consisting of: hydrogen, deuterium, CH$_3$, F, $^{19}$F, and $^{18}$F;

wherein optionally Z and W are taken together to form a C$_3$-C$_8$ heterocycloalkyl or C$_4$-C$_{10}$ heteroaryl or bicyclic ring system in which one of the rings must be a C$_4$-C$_{10}$ heteroaryl;

and wherein any and all heterocyclic and heteroaryl rings contain up to four heteroatoms selected from the group consisting of: O, N, and S;

with the proviso that when both Z and W are heteroatoms, the value of q cannot be 1;

and with the proviso that when $R^2$ is hydrogen, at least one of the $R^3$ or $R^4$ groups is not hydrogen;

or a tautomer and/or a pharmaceutically acceptable salt thereof.

In some embodiments, the compound is a compound of formula VI:

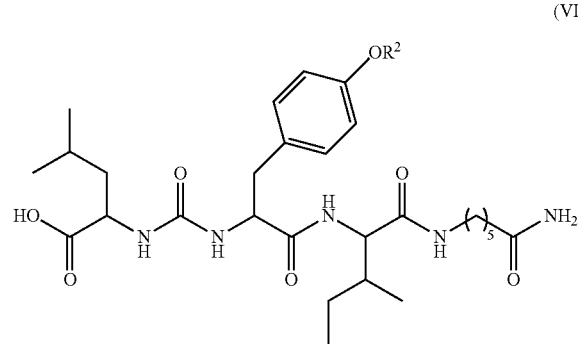

(VI)

wherein:
R² is selected from the group consisting of: hydrogen, -$\xi$- PO(OY)₂, -$\xi$- PO(OH)₂, and —C(=O)—Y, where Y is —Z—(CH₂)$_q$—W—R$^b$, q is 0-4, where Z and W are independently selected from the group consisting of: CH₂, O, S, NR$^c$ and R$^b$, where R$^c$ is selected from the group consisting of: hydrogen, $C_1$-$C_4$ alkyl, and $C_3$-$C_6$ cycloalkyl, R$^b$ is selected from the group consisting of: hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl;

wherein optionally Z and W are taken together to form a $C_3$-$C_8$ heterocycloalkyl or $C_4$-$C_{10}$ heteroaryl or bicyclic ring system in which one of the rings must be a $C_4$-$C_{10}$ heteroaryl;

wherein any and all heterocyclic rings contain up to four heteroatoms selected from the group consisting of: O, N, and S;

with the proviso that when both Z and W are heteroatoms, the value of q cannot be 1;

or a tautomer and/or a pharmaceutically acceptable salt thereof.

In some embodiments, the compound is a compound of Formula I, where R¹ is a $C_5$ alkyl.

In some embodiments, the compound is a compound of Formula I, where R² is —C(=O)—Y, where Z is N, and Z and W taken together form a $C_5$ heterocycle.

In some embodiments, the compound is a compound of Formula I, where R² is -$\xi$- PO(OH)₂.

In some embodiments, the compound is a compound of Formula I, where R⁵ is -$\xi$- CH₂—O—CO—Y.

In some embodiments, the compound is a compound of Formula I, where R¹ is a $C_1$-$C_{12}$ alkyl, R³ and R⁴ are both hydrogen and R⁵ is hydrogen.

In some embodiments, the compound is a compound of Formula II, where R¹ is $C_1$-$C_{12}$ alkynyl.

In some embodiments, the compound is a compound of Formula II, where R² is a —C(=O)—Y, where Z is CH₂, q is 0, W is N, and R³ and R⁴ together form a spirocyclic ring system where one ring is a $C_4$ heterocycle and the other is a $C_5$ cycloalkyl.

In some embodiments, the compound is a compound of Formula II, where m is 0, R¹ is a $C_1$-$C_{12}$ alkyl, and R³ and R⁴ together form a spirocyclic ring system.

In some embodiments, the compound is a compound of Formula II, where m is 1 or 2, R¹ is a $C_1$-$C_{12}$ alkyl, R³ and R⁴ together form a spirocyclic ring system, and R⁶ is selected from the group consisting of: hydrogen, deuterium, F, ¹⁹F, and ¹⁸F.

In some embodiments, the compound is a compound of Formula III, where R¹ is a $C_5$ alkyl.

In some embodiments, the compound is a compound of Formula III, where R³ and R⁴ are both hydrogen and R² is -$\xi$- PO(OH)₂.

In some embodiments, the compound is a compound of Formula III, where R¹ is a $C_1$-$C_{12}$ alkyl, R² is —C(=O)—Y, and R³ and R⁴ are both hydrogen.

In some embodiments, the compound is a compound of Formula III where R¹ is a $C_1$-$C_{12}$ alkyl, R² is -$\xi$- PO(OH)₂, and R³ and R⁴ are both hydrogen.

In some embodiments, the compound is a compound of Formula IV, where n is 5, m is 1 or 2, and R⁶ is selected from the group consisting of: hydrogen, deuterium, F, ¹⁹F, and ¹⁸F.

In some embodiments, the compound is a compound of Formula IV, where R⁵ is a $C_5$ alkyl.

In some embodiments, the compound is a compound of Formula IV, where m is 1 or 2, R³ and R⁴ are both hydrogen, and R⁶ is selected from the group consisting of: hydrogen, deuterium, F, ¹⁹F, and ¹⁸F.

In some embodiments, the compound is a compound of Formula IV, where m is 0, R³ and R⁴ are both hydrogen.

In some embodiments, the compound is a compound of Formula V, where R² is —C(=O)—Y, where Y is —Z—(CH₂)$_q$—W—R$^b$, q is 2, where Z is NH, W is N(CH₃) and R$^b$ is CH₃.

In some embodiments, the compound is a compound of Formula V, where R³ and R⁴ together form a spirocyclic ring system.

In some embodiments, the compound is a compound of Formula V, where m is 1 or 2, R² is —C(=O)—Y, and R⁶ is selected from the group consisting of: hydrogen, deuterium, F, ¹⁹F, and ¹⁸F.

In some embodiments, the compound is a compound of Formula V, where m is 1 or 2, R² is -$\xi$- PO(OH)₂, and R⁶ is selected from the group consisting of: hydrogen, deuterium, F, ¹⁹F, and ¹⁸F.

In some embodiments, the compound is a compound of Formula VI, where R² is -$\xi$- PO(OH)₂.

In some embodiments, the compound is a compound of Formula VI, where R² is hydrogen.

In some embodiments, the compound is a compound of Formula VI, where R² is —C(=O)—Y, and Z and W together form a $C_3$-$C_8$ heterocycloalkyl.

In some embodiments, the compound is a compound of Formula VI, where R² is -$\xi$- PO(OH)₂.

In some embodiments, the compound is a compound selected from the following structures:

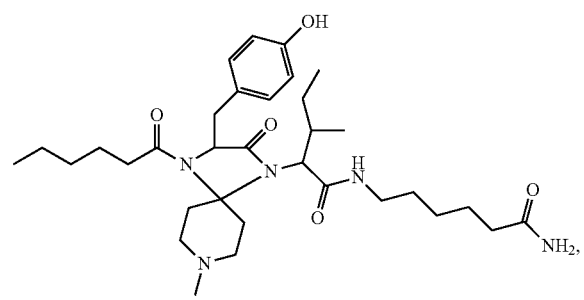

1

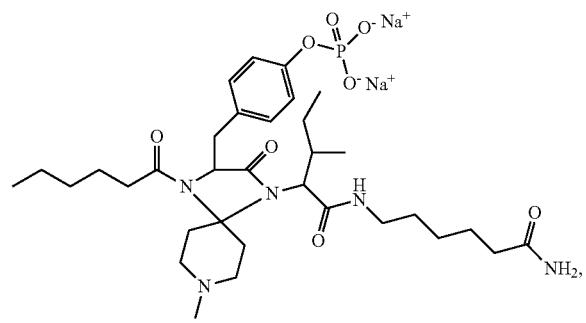
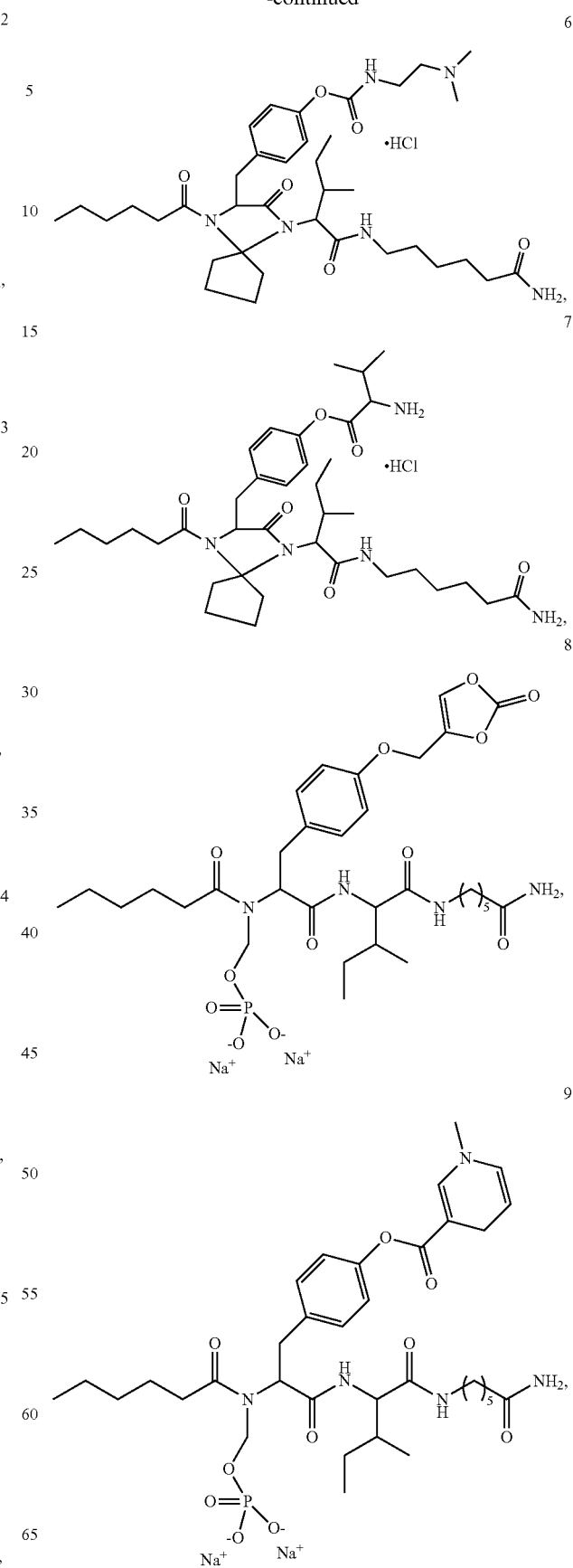

-continued
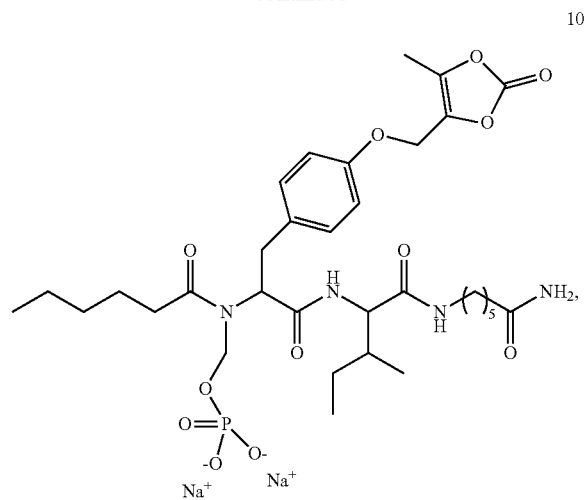
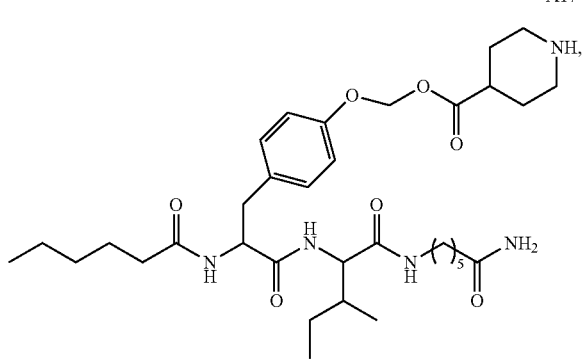
A17ᵃ
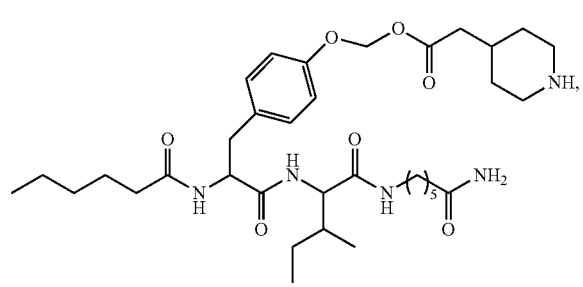
A17ᵇ
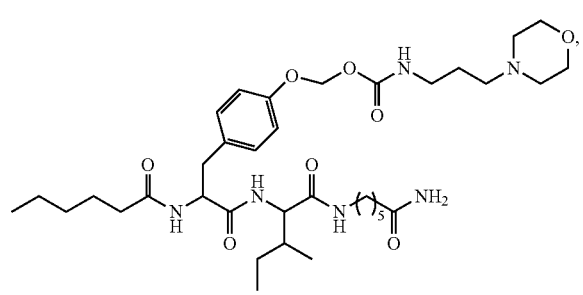
A17ᶜ
-continued
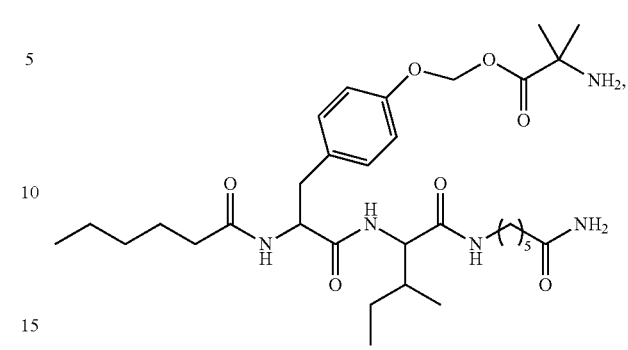
A17ᵉ
A17f
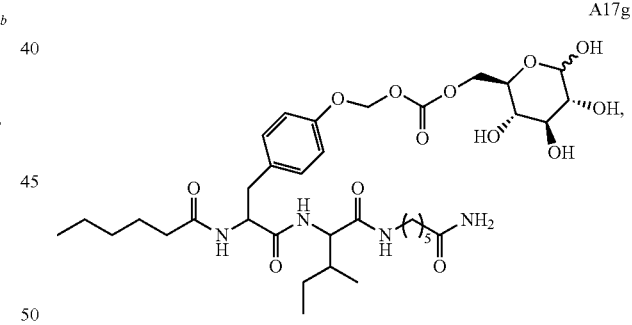
A17g
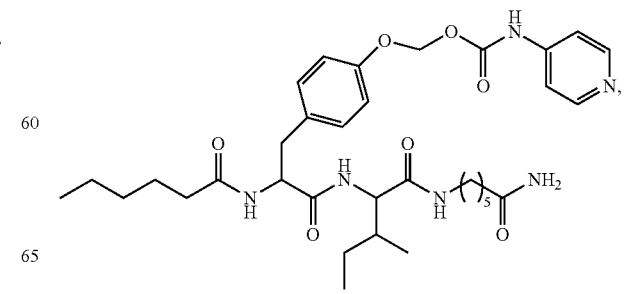
A17h

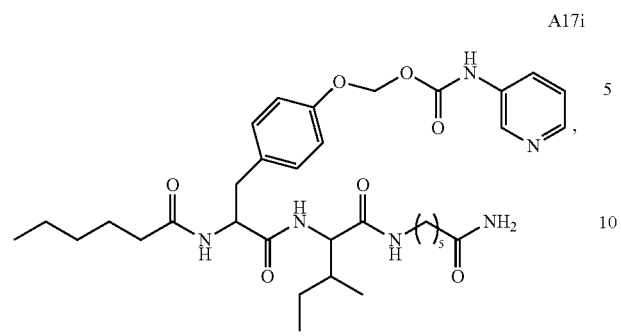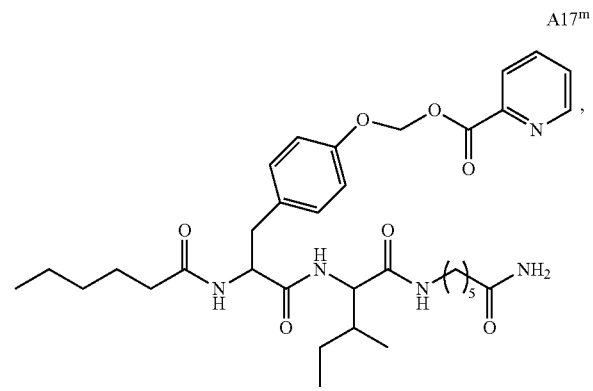

-continued
A21
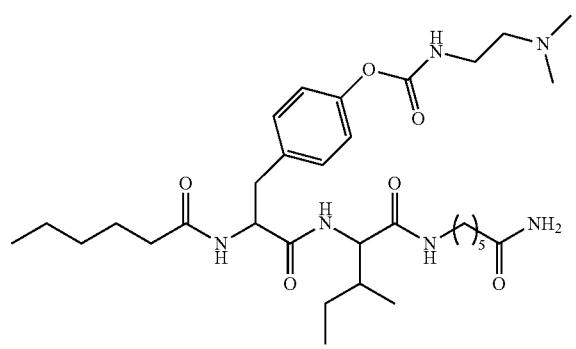
A22
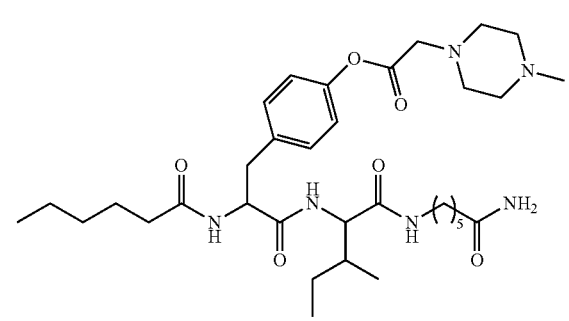
A23
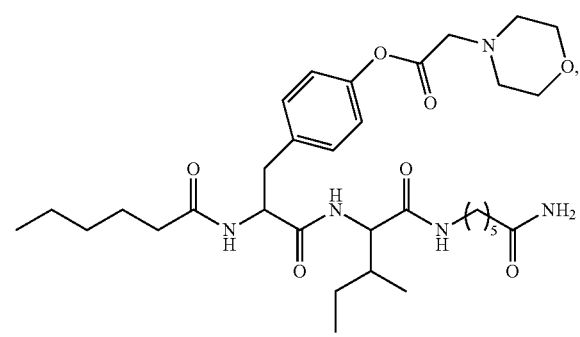
A24
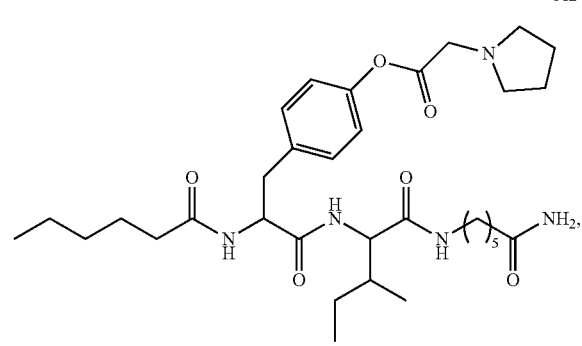
-continued
A25
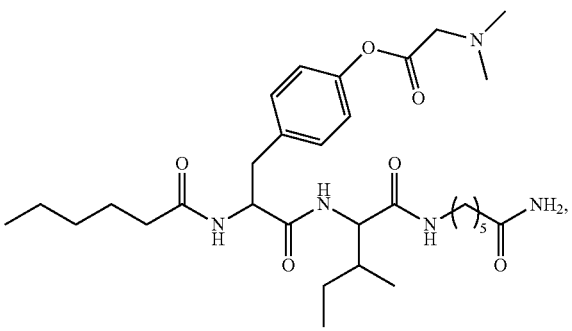
A26
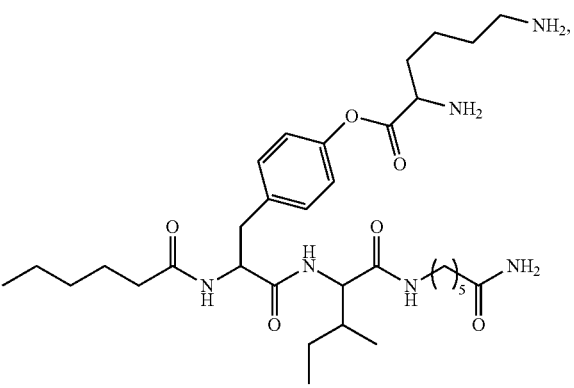
A27
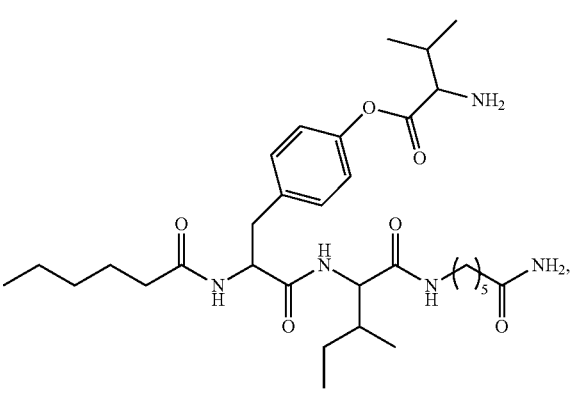
and
A28
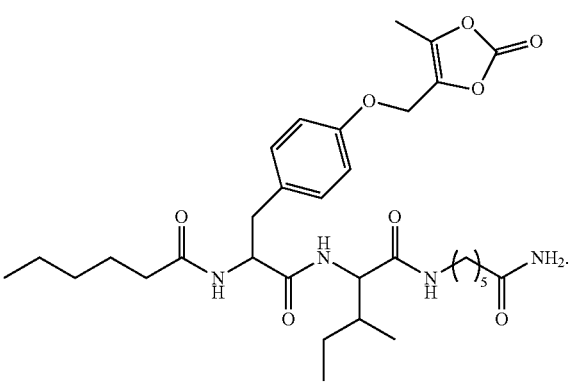

In some embodiments, the compound is a compound selected from the following structures:

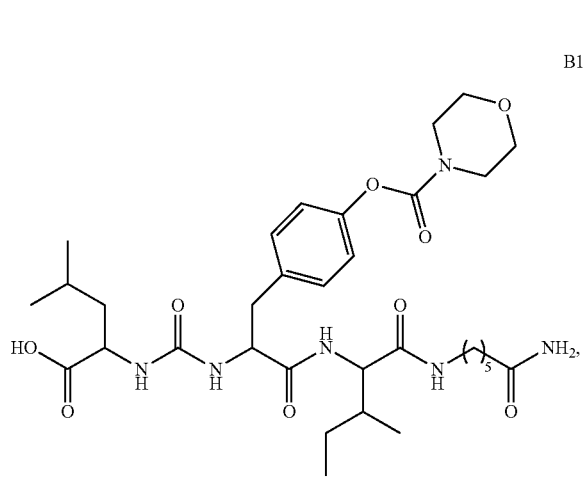

B1

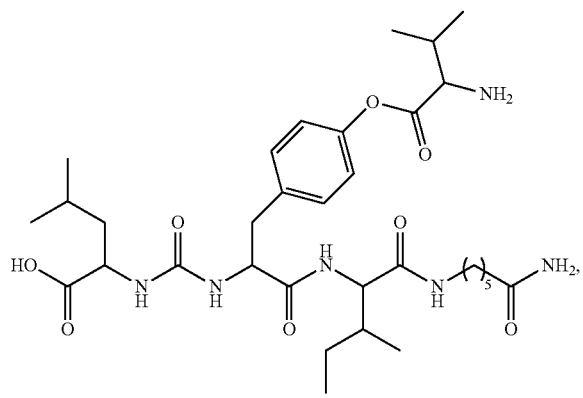

B2

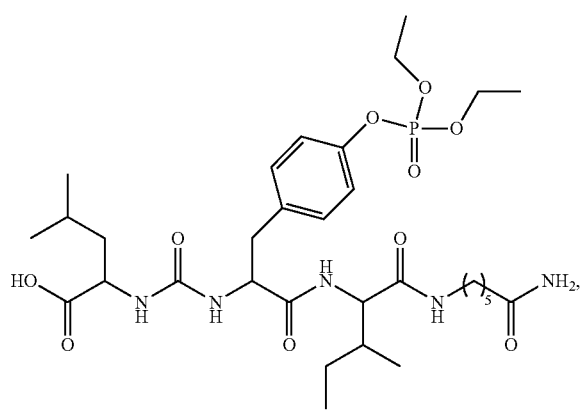

B3

-continued

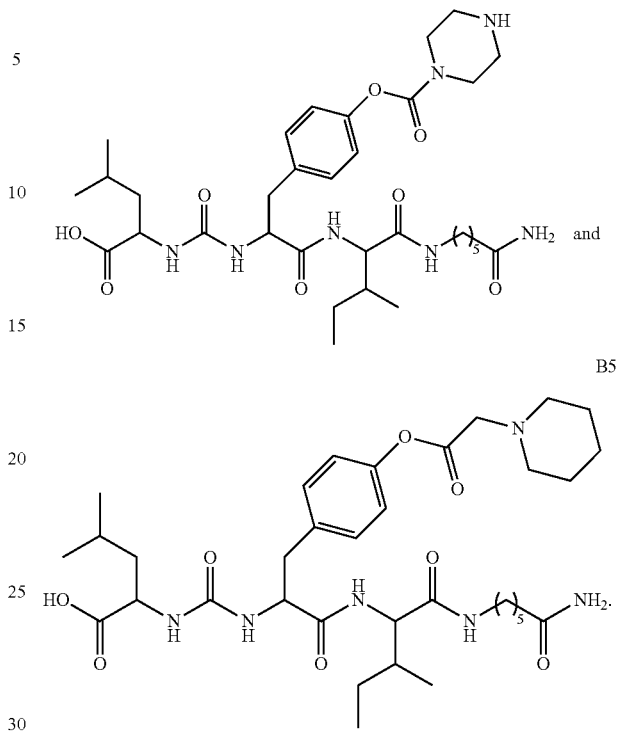

B4 and

B5

Synthesis 5.3.1. General Synthetic Methods

The compounds described herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactant or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional group are well known in the art. For example, numerous protecting groups are described in T. W. Greene and P. G. M. Wuts, Protecting Groups in Organic Synthesis, Third Edition, Wiley, New York, 1999, and references cited therein.

If the compounds described herein contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA), CombiChem (SAN DIEGO, Calif.). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

5.3.2. Synthesis Routes to Described Compounds

The following specific, non-limiting examples are illustrative of the invention.

In one general embodiment, the method comprises reacting an appropriately N-protected compound with nucleophilic coupling partner and HATU to give the desired amide. It is appreciated that other suitable coupling conditions and reagents, such as HOBt and/or DMAP, may be used to form a requisite amide. The skilled artisan will appreciate that there are many synthetic conditions or methods by which an amide functional group can be made, for example by reacting the starting carboxylate to synthesize a reactive derivative such as the corresponding acid chloride and then reacting that intermediate directly with the amine nucleophile to produce the desired amide. These synthetic methods are well within in the scope of the present technology disclosed.

On the other hand, it is generally known that the N-terminus of di-peptide derivatives can be produced by first protecting or blocking (i.e. putting on the desired amide group on the C-terminus if the functional groups are compatible so as to not interfere with the subsequent steps in the overall synthesis of the compound and thus, are "orthogonal") the C-terminus and reacting the free di-peptide amine with an activated electrophile such as an acid anhydride, acid chloride, phosphorus oxychloride or phosphonyl chloride.

Of course it is recognized that esterification reactions may be used to generate non-trivial groups on the tyrosine moiety. Such reactions can be accelerated by using anhydrides, or other acid catalysts, when reacting the free alcohol with a reactive carboxy compound. Functional groups which are appropriate for active carboxy compound include, but are not limited to, anhydrides, acid chlorides, Mitsunobu conditions or Steglich-type conditions or anhydrous acid conditions with the carboxylic acid.

In one general embodiment, the synthesis can include functionalizing the nitrogen atoms of the amides on the di-peptide derivative. Such reactions are commonly accomplished by protecting sensitive functional groups on the rest of the molecule whilst generating an anion on one or both of the nitrogen by adding a strong base such as sodium amide, LDA, a Grignard reagent, or LiN(i-Pr)$_2$. Of course this list of bases is not comprehensive. The next step would be to add the appropriate electrophile. In the case where the artisan would like to make a spirocyclic ring system with the two nitrogen atoms of the di-peptide derivative, one could add a di-functionalized electrophile such as 1,1 di-bromo-cyclopentane, or even the requisite carbonyl compound under strong Lewis acidic conditions will work.

Herein it is understood that amino, keto, thio, hydroxyl, and any other necessary protecting groups and their methods of deprotection are known in the art, such as those described in T. W. Greene and P. G. M. Wuts, Protecting Groups in Organic Synthesis, Third Edition, Wiley, New York, 1999.

Alternatively, the skilled artisan will recognize that there is additional synthetic functional group modifications that one can use to prepare spirocyclic and other bicyclic or tricyclic compounds from dipeptide derivative intermediates.

5.4. Compositions

In another aspect, compositions are provided that comprise at least one compound as described herein.

In various embodiments, the compositions comprise one compound as described herein. In other embodiments, the compositions comprise a plurality of compounds as described herein. In certain of these latter embodiments, the compositions comprise 2, 3, 4, or 5 or more of the herein described compounds. In typical embodiments comprising a plurality of compounds, the compounds are selected to have pharmacokinetic properties different from one another.

In certain embodiments, the composition comprises at least one compound as described herein, and Base Structure. In various embodiments, the composition comprises 1, 2, 3, 4, or 5 compounds as described herein, and Base Structure. In typical embodiments, the compounds are selected to have pharmacokinetic properties different from Base Structure. In certain embodiments in which a plurality of compounds as described herein are included, the compounds are selected to have pharmacokinetic properties different from one another.

In various embodiments, the composition comprises at least one compound of Formula I, or tautomers, stereoisomers, salts, solvates or hydrates thereof.

In various embodiments, the composition comprises at least one compound of Formula II, or tautomers, stereoisomers, salts, solvates or hydrates thereof.

In certain embodiments, the composition comprises at least one compound selected from the group consisting of Compound 1, Compound 2, Compound 3, Compound 4, Compound 5, Compound 6, Compound 7, Compound 8, Compound 9, and Compound 10, as described herein above, or tautomers, stereoisomers, salts, solvates or hydrates thereof.

In certain embodiments, the composition comprises at least one compound selected from the group consisting of compound 1-10, A2-A17, A17a-17m, A18-A34f, and B1-B5 as described herein above, tautomers, stereoisomers, salts, solvates or hydrates thereof.

In various embodiments, the composition is a solid.

In various other embodiments, the composition is a liquid.

In various fluid embodiments, at least one of the at least one compound in the composition is present at a concentration of at least 10 ng/mL, 50 ng/mL, 100 ng/mL, 500 ng/mL, 1 ug/mL, 10 ug/mL, 50 ug/mL, 75 ug/mL, 0.1 mg/ml, 0.2 mg/ml, 0.3 mg/ml, 0.4 mg/ml, even at least 0.5 mg/ml. In some fluid embodiments, at least one of the at least one compound in the composition is present at a concentration of at least 1 mg/ml, 2 mg/ml, 3 mg/ml, 4 mg/ml or 5 mg/ml. In some fluid embodiments, at least one of the at least one compound in the composition is present at a concentration of at least 10 mg/ml, 20 mg/ml, 30 mg/ml, 40 mg/ml or 50 mg/ml. In some fluid embodiments, at least one of the compound in the composition is present at a concentration of at least 100 mg/ml, 125 mg/ml, 150 mg/ml, 175 mg/ml, or 200 mg/ml. In some fluid embodiments, at least one of the at least one compound in the composition is present at a concentration of at least 250 mg/ml.

In certain fluid embodiments, each of the at least one compound in the composition is present at a concentration of at least 0.1 mg/ml, 0.2 mg/ml, 0.3 mg/ml, 0.4 mg/ml, even at least 0.5 mg/ml. In some fluid embodiments, each of the at least one compound in the composition is present at a concentration of at least 1 mg/ml, 2 mg/ml, 3 mg/ml, 4 mg/ml or 5 mg/ml. In some fluid embodiments, each of the at least one compound in the composition is present at a concentration of at least 10 mg/ml, 20 mg/ml, 30 mg/ml, 40 mg/ml or 50 mg/ml. In some fluid embodiments, each of the at least one compound in the composition is present at a concentration of at least 100 mg/ml, 125 mg/ml, 150 mg/ml, 175 mg/ml, or 200 mg/ml. In some fluid embodiments, each of the at least one compound in the composition is present at a concentration of at least 250 mg/ml.

5.5. Pharmaceutical Compositions

In a further aspect, pharmaceutical compositions are provided that comprise at least one of the compounds described herein and a pharmaceutically acceptable carrier or excipient.

In various embodiments, the pharmaceutical compositions comprise one compound as described herein. In other embodiments, the pharmaceutical compositions comprise a plurality of compounds as described herein. In certain of these latter embodiments, the pharmaceutical compositions comprise 2, 3, 4, or 5 or more of the herein described compounds. In typical embodiments comprising a plurality of compounds, the compounds are selected to have pharmacokinetic properties different from one another.

In certain embodiments, the pharmaceutical composition comprises at least one compound as described herein, and Base Structure. In various embodiments, the pharmaceutical composition comprises 1, 2, 3, 4, or 5 compounds as described herein, and Base Structure. In typical embodiments, the compounds are selected to have pharmacokinetic properties different from Base Structure. In certain embodiments in which a plurality of compounds as described herein are included, the compounds are selected to have pharmacokinetic properties different from one another.

In various embodiments, the pharmaceutical composition comprises at least one compound of Formula I, or tautomers, stereoisomers, salts, solvates or hydrates thereof.

In various embodiments, the pharmaceutical composition comprises at least one compound of Formula II, or tautomers, stereoisomers, salts, solvates or hydrates thereof.

In certain embodiments, the pharmaceutical composition comprises at least one compound selected from the group consisting of Compound 1, Compound 2, Compound 3, Compound 4, Compound 5, Compound 6, Compound 7, Compound 8, Compound 9, and Compound 10, as described herein above, or tautomers, stereoisomers, salts, solvates or hydrates thereof.

In certain embodiments, the pharmaceutical composition comprises at least one compound selected from the group consisting of Compound 1-10, A2-A17, A17a-17m, A18-A34f, and B1-B5, as described herein above, tautomers, stereoisomers, salts, solvates or hydrates thereof.

In various embodiments, the pharmaceutical composition is formulated for enteral route of administration.

Pharmaceutical compositions for enteral route of administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included. A pharmaceutical composition can include a cyclodextrin. A pharmaceutical composition can contain poloxamer and/or Vitamin E TPGS.

In embodiments in which the pharmaceutical composition is formulated for enteral route of administration in a solid dosage form, the composition will contain, on a weight percent (wt %) basis, from about 0.01-99.99 wt % of the compound of the present technology based on the total formulation, with the balance being one or more suitable pharmaceutical excipients. Preferably, the compound is present at a level of about 1-80 wt %.

In other embodiments, the pharmaceutical composition is formulated for inhalation suspended in solutions or mixtures of excipients (e.g., preservatives, viscosity modifiers, emulsifiers, buffering agents) in non-pressurized or pressurized dispensers that deliver a spray containing a metered dose of at least one compound as described herein. In certain inhalation embodiments, the pharmaceutical composition is formulated for nasal or oral administration.

In other embodiments, the pharmaceutical composition is formulated for topical administration. In certain topical embodiments, the pharmaceutical composition is formulated for enepidermic route, Epidermic route, Instillation administration, or Painting/Swabbing.

In other embodiments, the pharmaceutical composition is formulated for parenteral administration. In certain parenteral embodiments, the pharmaceutical composition is formulated for intravenous, subcutaneous, or intradermal administration. In other embodiments, the pharmaceutical composition is formulated for intrathecal or intracerebroventricular administration.

In typical parenteral embodiments, the composition will be in the form of a parenterally acceptable aqueous solution that is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In various fluid embodiments, at least one of the compound in the pharmaceutical composition is present at a concentration of at least 0.1 mg/ml, 0.2 mg/ml, 0.3 mg/ml, 0.4 mg/ml, even at least 0.5 mg/ml. In some fluid embodiments, at least one of the at least one compound in the pharmaceutical composition is present at a concentration of at least 1 mg/ml, 2 mg/ml, 3 mg/ml, 4 mg/ml or 5 mg/ml. In some fluid embodiments, at least one of the at least one compound in the pharmaceutical composition is present at a concentration of at least 10 mg/ml, 20 mg/ml, 30 mg/ml, 40 mg/ml or 50 mg/ml. In some fluid embodiments, at least one of the at least one compound in the pharmaceutical composition is present at a concentration of at least 100 mg/ml, 125 mg/ml, 150 mg/ml, 175 mg/ml, or 200 mg/ml. In some fluid embodiments, at least one of the at least one compound in the pharmaceutical composition is present at a concentration of at least 250 mg/ml.

In certain fluid embodiments, each of the at least one compound in the pharmaceutical composition is present at a concentration of at least 0.1 mg/ml, 0.2 mg/ml, 0.3 mg/ml, 0.4 mg/ml, even at least 0.5 mg/ml.

In some fluid embodiments, each of the at least one compound in the pharmaceutical composition is present at a concentration of at least 1 mg/ml, 2 mg/ml, 3 mg/ml, 4 mg/ml or 5 mg/ml. In some fluid embodiments, each of the at least one compound in the pharmaceutical composition is present at a concentration of at least 10 mg/ml, 20 mg/ml, 30 mg/ml, 40 mg/ml or 50 mg/ml. In some fluid embodiments, each of the at least one compound in the pharmaceutical composition is present at a concentration of at least 100 mg/ml, 125 mg/ml, 150 mg/ml, 175 mg/ml, or 200 mg/ml. In some fluid embodiments, each of the at least one compound in the pharmaceutical composition is present at a concentration of at least 250 mg/ml.

5.6. Methods of Use

In another aspect, methods of treatment are provided.

The methods comprise administering at least one compound as described herein to a subject in an amount effective to treat, protect from, or reverse neurodegenerative disease, to prevent or reverse the symptoms of dementia, to facilitate repair of traumatic injury to the nervous system, or to enhance cognitive function. In various embodiments, the subject has a disease selected from Alzheimer's disease, Parkinson's disease, amyotrophic lateral sclerosis, other dementias and neurodegenerative diseases, spinal cord injury, traumatic brain injury, and/or sensorineural hearing and vision loss. In typical embodiments, the method comprises administering a pharmaceutical composition comprising at least one of the compounds described herein, as described above.

In some aspects, a method for treating a disease state or condition is provided for, the method comprising administration of an effective amount of one or more compounds of the formulae as disclosed herein or a pharmaceutical composition as disclosed herein to a subject in need thereof.

In some aspects, a method for treating a disease state or condition is provided for, where the disease is neurodegenerative disease.

In some aspects, a method for treating a disease state or condition is provided for, where the disease is selected from the group consisting of: Alzheimer's disease, Parkinson's disease, amyotrophic lateral sclerosis, other dementias and neurodegenerative diseases, spinal cord injury, traumatic brain injury, sensorineural hearing and vision loss.

In some aspects, a method for treating a disease state or condition is provided for, where the disease is Alzheimer's disease.

In some aspects, a method for treating a disease state or condition is provided for, where the disease is Parkinson's disease.

In some aspects, a method for treating a disease state or condition is provided for, where wherein the route of administration is selected from the group consisting of: enteral, parenteral, inhalation, topical including but not limited to oral, intravenous, subcutaneous, intrathecal, and intracerebroventricular administration.

In some aspects, a method for treating a disease state or condition is provided for, where the administration is intravenous.

In some aspects, a method for treating a disease state or condition is provided for, where the method is performed in-vitro. In some aspects, a method for treating a disease state or condition is provided for, where the method is performed in-vivo.

In some aspects, a method for treating a disease state or condition is provided for, where the subject is a mammal. In some aspects, a method for treating a disease state or condition is provided for, where the subject is a human.

In some aspects, the use of one or more compounds disclosed herein is provided for in the manufacture of a medicament for treating a disease state or condition described herein.

In various embodiments, the compound is administered as the sole medical treatment. In various embodiments, the compound is administered in combination with other medical and/or surgical interventions according to the prevailing standards of care.

In various embodiments, the dose is determined without regard to patient weight. In certain embodiments, the dose is between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. Additionally, a dose can be administered daily or alternatively, a few times a week, where the subsequent dose is administered after 1, 2 or 3 day interval.

In some embodiments, the dose is determined based on patient weight. In certain embodiments, the dose is between 0.001 mg/kg patient weight to about 15 mg/kg per kg patient weight per administration, or 0.01 mg/kg to about 1.5 mg/kg.

The amount of compound administered will vary depending upon the disease treated, the route of administration, and the dosage schedule.

It will be understood, however, that the specific dose level for any particular subject will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

Therapy can extend for a number of days, a number of weeks or months, and in some cases, years.

A composition can be administered alone or in combination with other treatments, either simultaneously or sequentially dependent upon the condition to be treated.

Dosage amount and dosage schedule may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

6. EXAMPLES

The following synthetic and biological examples are offered to illustrate this the present technology and are not to be construed in any way as limiting the scope of this the present technology. Unless otherwise stated, all temperatures are in degrees Celsius.

The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992), and Organic Reactions, Volumes 1-40 (John Wiley, and Sons, 1991).

The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings. +If an abbreviation is not defined, it has its generally accepted meaning.

aq.=aqueous
LC-MS=liquid chromatography-mass spectrometry
MS=mass spectrometry
THF=tetrahydrofuran
NaHCO$_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trI zolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
Na$_2$CO$_3$=sodium carbonate
NMR=nuclear magnetic resonance
NaOH=sodium hydroxide
Na$_2$SO$_4$=sodium sulfate
TLC=thin layer chromatography
UV=ultraviolet
wt %=weight percent
µM=micromolar

6.1. Example 1: Syntheses

General Experimental Details:

Final compounds were confirmed by HPLC/MS analysis and determined to be ≥90%. $^1$H and $^{13}$C NMR spectra were recorded in CDCW (residual internal standard CHCW=δ 7.26), DMSO-d$_6$ (residual internal standard CD$_3$SOCD$_2$H=δ 2.50), methanol-d$_4$ (residual internal standard CD$_2$HOD=δ 3.20), or acetone-d$_6$ (residual internal standard CD$_3$COCD$_2$H=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

In general, the compounds of the present invention may be prepared as illustrated in the general reaction schemes described below, or by modifications thereof, using readily available starting materials, reagents, and conventional synthesis procedures, or could be inferred by one skilled in the art. Generally, compounds of the Formula I, may be prepared by standard solution phase or solid-phase synthesis from commercially available inputs by procedures well established in the art. For example, acylation of the amino terminal would then provide a common intermediate A2. The tyrosyl hydroxyl group of A2 can be acylated with a carboxylic acid derivative (A3), which may be a N—BOC protected amino-acid (such as α, β, γ or ω amino acid, or a di-amino acid derivative such as Lys or Orn) followed by removal of the amine protecting group under acidic conditions to provide A4 (Scheme 1 below).

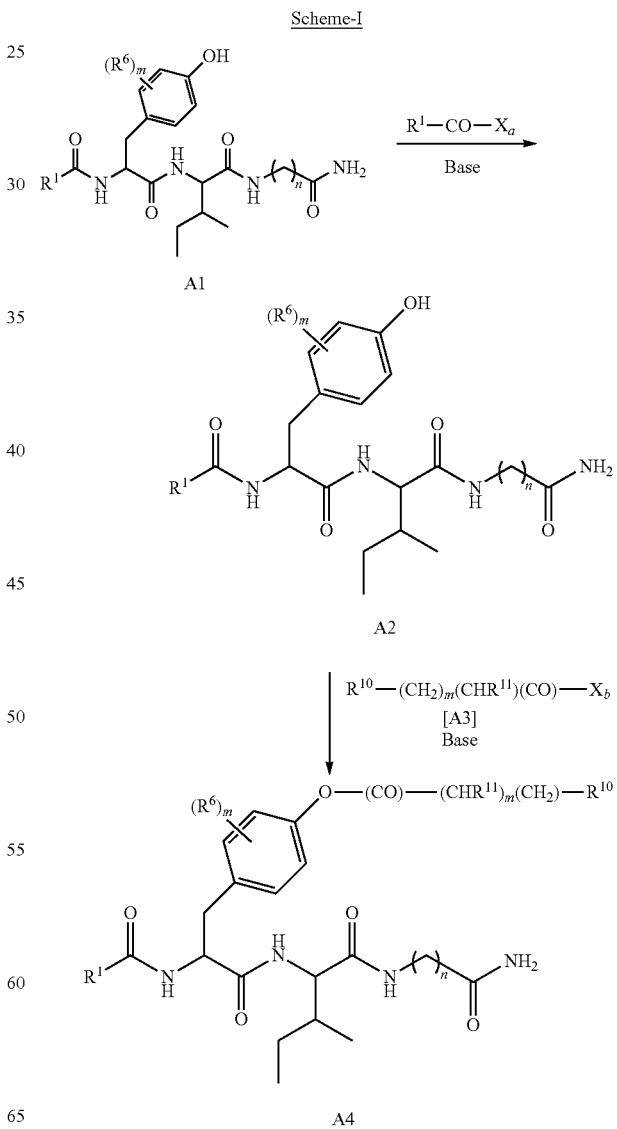

Scheme-I

Alternatively, the carboxylic acid A3 may represent N-mono or N,N-dialkylated amino acid derivatives, as several such analogs are commercially available, and the final product can then be converted to corresponding amine salt, A4, as depicted in Scheme-I Alternatively, the tyrosyl hydroxyl of A2 may be derivatized to provide a mixed carbonate derivative, A6, which could then be reacted with an alcohol or an amine derivative, A7, to provide the corresponding carbonate or carbamate derivatives such as A8 and A10, respectively (Scheme-II). A wide range of starting materials, alcohol or amine derivatives, represented by A7, are commercially available or could be prepared by short synthetic sequence reported in published literature. The carbamate derivatives, A10, could also be prepared directly from A2 via reaction with carbamoyl chlorides, A9. Some carbamoyl chlorides are commercially available and others could be prepared just prior to use from corresponding secondary amine and diphosgene.

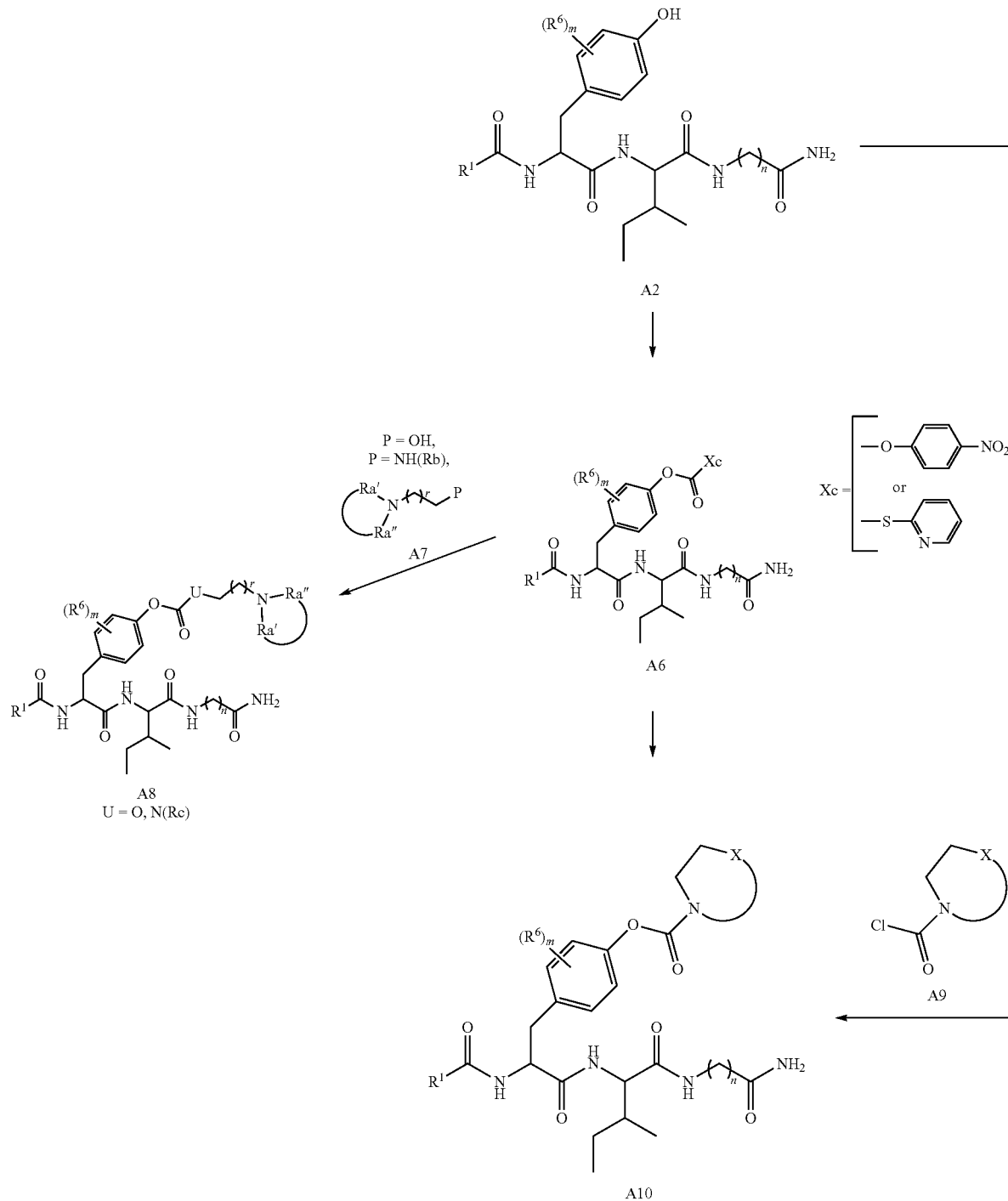

Tyrosyl hydroxyl could be converted to phosphate derivatives A12, A13, A15, as shown in Scheme-III. The reaction with 2-eq of appropriate alcohols with either POCl3 or 4-nitrophenyl phosphorodichloridate provides intermediate A14, which is then used to derivatize the phenolic hydroxyl of A2 to provide a desired product, A15.

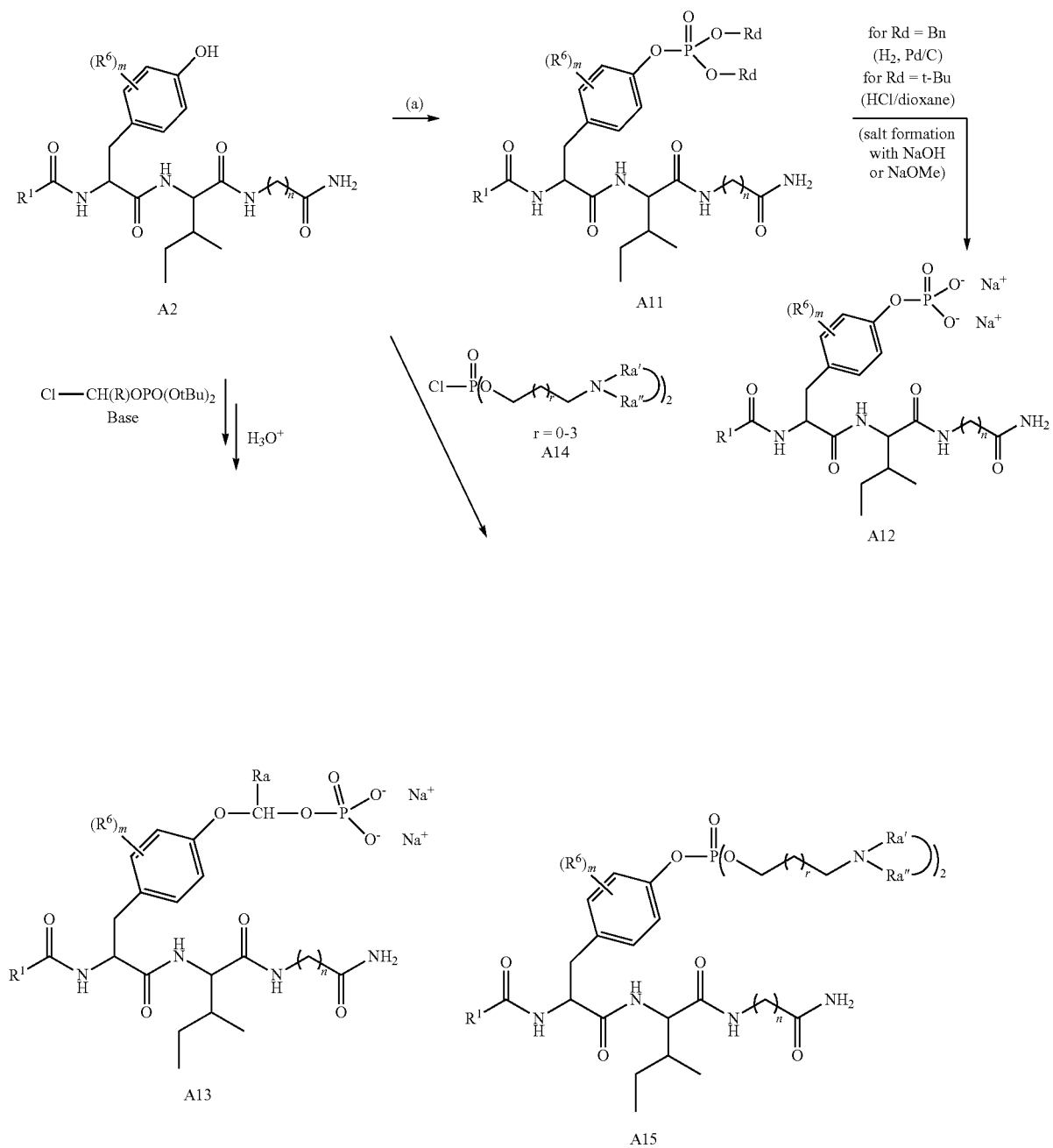

Scheme-III

Another variant of R2 derivatives where the prodrug moiety represents alkoxy-carbonyl based-derivatives can be prepared by route and chemistries shown in Scheme IV. For alkylation of A2, the alkoxy-carbonyl reagents, A16, where the amine is protected with an acid labile BOC group can be prepared utilizing the chemistries, as outlined in Scheme V, or via commercially available reagents. Table 1 below represents some non-limiting examples of these derivatives as a R2 substituent, where A17g represents an example of non-amine based, polyhydroxyl solubility enhancing moiety.

Scheme-IV
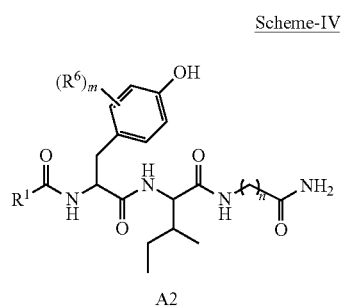 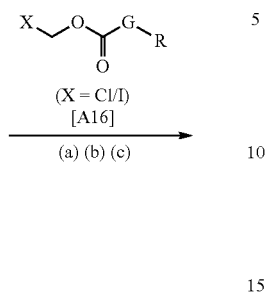 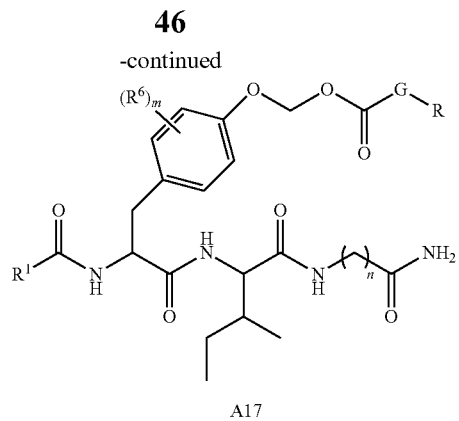
Scheme V: Preparation of Prodrug moiety (A16).
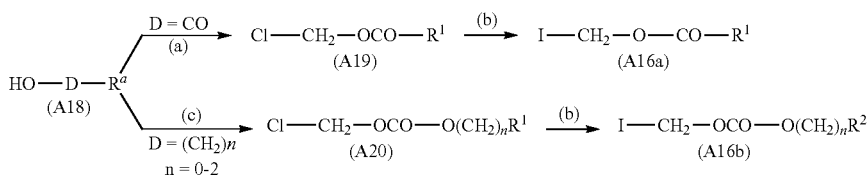
Reagents: (a) Cl—CH$_2$—OSO$_2$Cl, aq. NaHCO3, CH$_2$Cl$_2$ (b) NaI/acetone (if required), (c) Cl—CH$_2$—OCOCl, base,
TABLE 1
Representative Examples of Alkoxy-carbonyl-derived compounds, for simplicity shown for R$^6$ = H
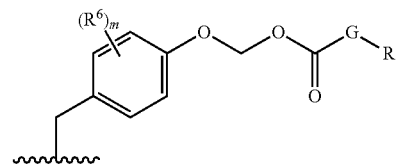
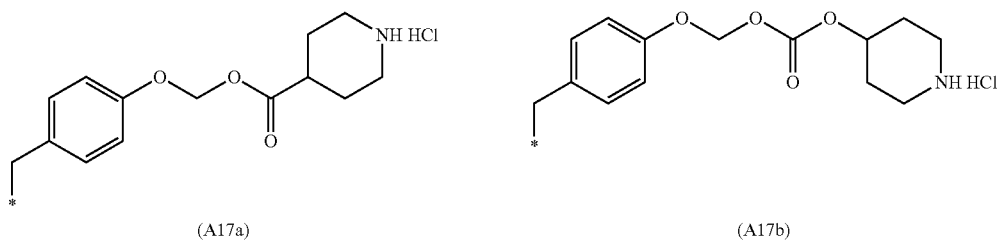
(A17a)  (A17b)
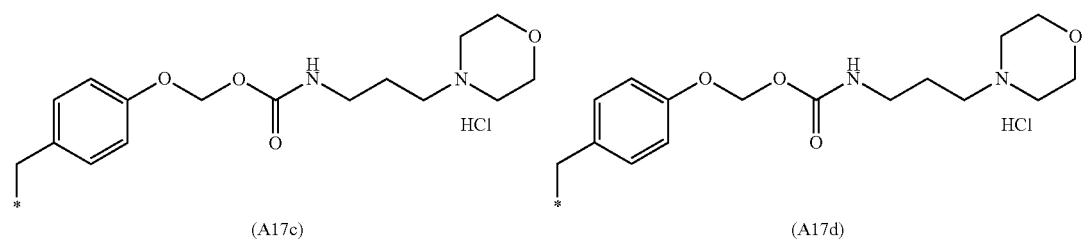
(A17c)  (A17d)

TABLE 1-continued

Representative Examples of Alkoxy-carbonyl-derived compounds, for simplicity shown for $R^6$ = H

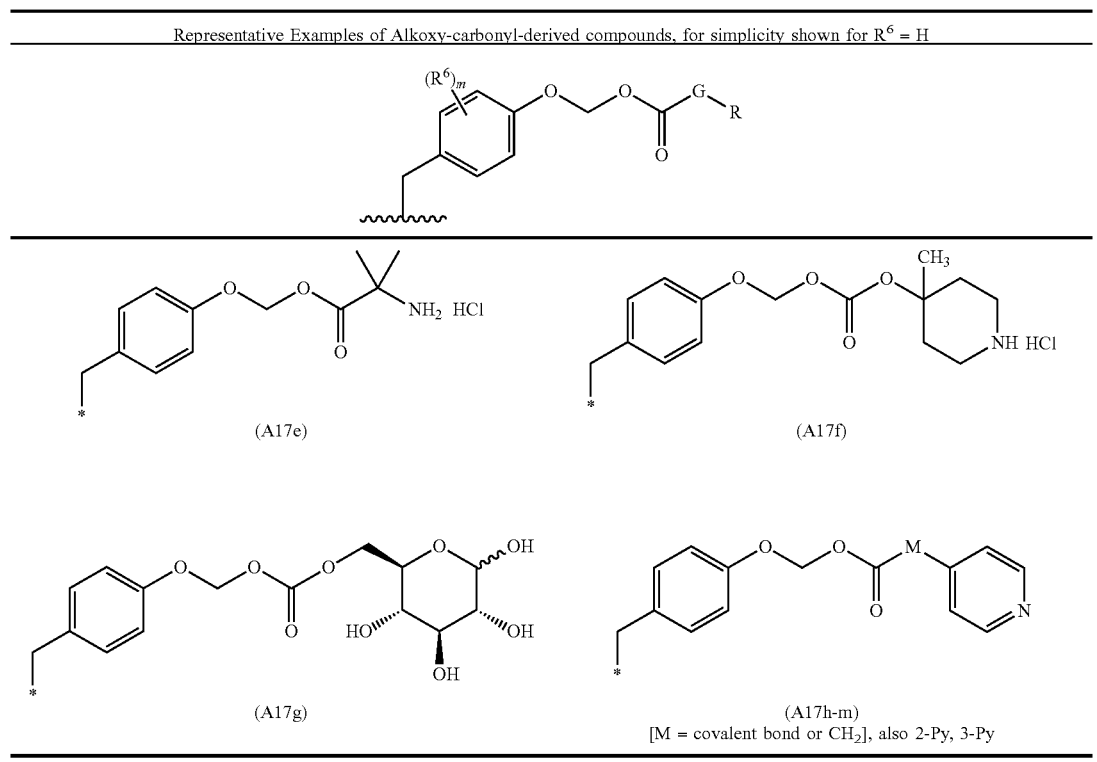

(A17e)

(A17f)

(A17g)

(A17h-m)
[M = covalent bond or $CH_2$], also 2-Py, 3-Py

Chemistries for incorporation of R3-R4 bicyclic derivatives are shown in the Schemes below. When symmetrical acyclic or cyclic ketones are used for ring formation, no new chiral center will be produced. However, unsymmetrical ketone or aldehyde derived cyclization will generate a new chiral center. The cyclization is expected to proceed via the intermediacy of a Schiff's base, and since chirally pure peptide derivative will be used, one would expect to obtain a thermodynamically stable cyclic-aminal (imidazolidinone) product. A literature report by Lydie, H. et. al. Tett. Letters (2015) 6240-6243, provides an example of cyclization reaction using 2-pyridine carboxaldehyde with a dipeptide, which provides two diastereomers in 46% and 11% yield]. The R3-R4 bridged mono- and/or spirocyclic aminals can be prepared either under acidic or base catalyzed conditions such as similar to or variations of conditions reported in the literature, such as, by, Gomes, P. et. al. Tetrahedron, 2004, 5551-62, DeMong. D. et. al. J. Med. Chem. 2014, 57, 2601-10, and reference cited therein. Subsequent N-acylation of A23A, followed by hydrogenation and removal of the acid labile protecting group, where applicable, will provide the target imidazolidinone derivatives A24A, Scheme VI.

Scheme VI

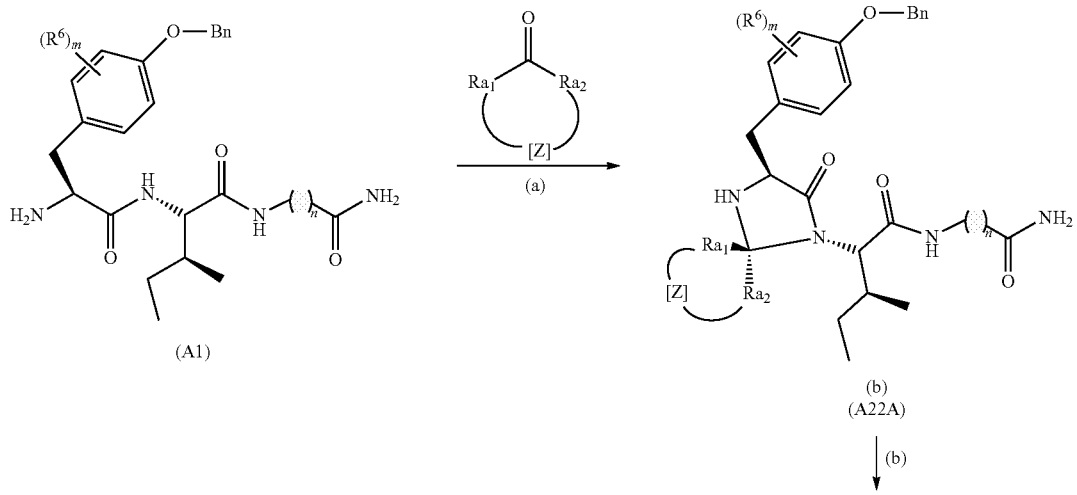

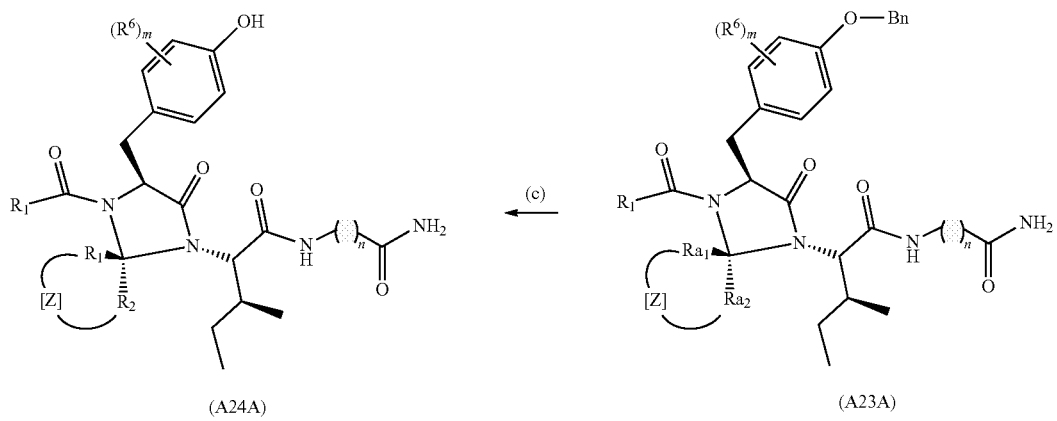

(A24A)  (A23A)

Reagents: (a) Cat. acid (pTSA or HOAc), in ROH (MeOH, EtOH, IPA) rt or gentle heat, (b) R¹COCl or (R¹—CO)₂O, Et₃N, THF or DMF, (c) H₂—Pd/C EtOH/IPA or galc. HOAc, RT, Alternatively, reaction of dipeptide (A25A) with a carbonyl compound could be used to prepare the cyclic aminals, A26A (Scheme VII). Subsequent N-acylation, followed by the coupling reaction shown, should provide the desired key intermediate (A23A), which would then be elaborated further as shown in Scheme VI.

Scheme VII

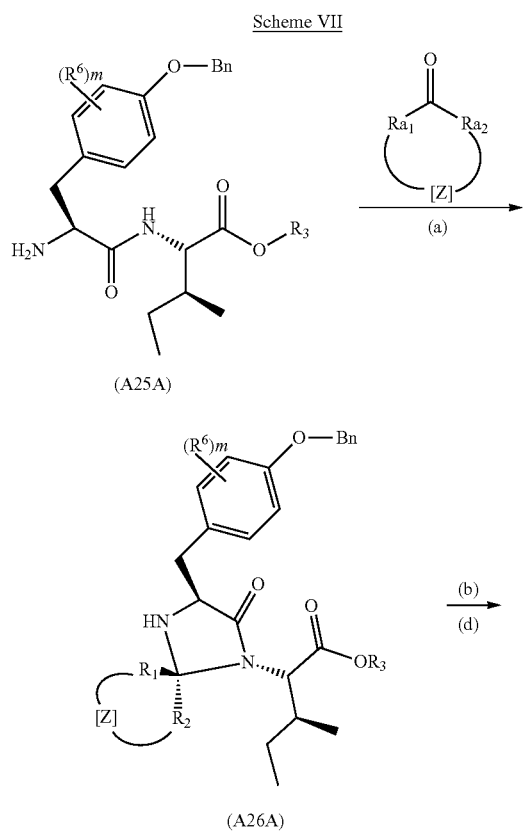

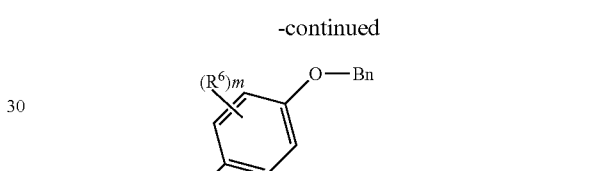

(A27A)

Reagents: (a) Cat. acid (pTSA or HOAc), in ROH (MeOH, EtOH, IPA) rt or gentle heat, (b) R¹COCl or (R¹—CO)₂O, Et₃N, THF or DMF, (c) H₂—Pd/C EtOH/IPA or galc. HOAc, RT, (d) R₃ = TBDMS, 0.5-1M aq HCl (e) EDCl, HOBt, NH₂⁻(CH₂)n—CONH₂

The alkoxy-carbonyl bearing an amino group can also be introduced at the C-terminal amide, which following esterase mediated bioconversion should regenerate A2. The chemistry to prepare reagents [A16] is similar to the one described above in Scheme V, except the prodrug generating reagents [A16] contains a CBZ protected amine. Some examples of the reagents used are shown in the box (insert) in Scheme VIII. Following synthesis of the protected penultimate intermediate, the final hydrogenation step in the presence of an acid would provide the desired prodrug derivative A33A.

Scheme VIII, C-terminal Amide Prodrugs

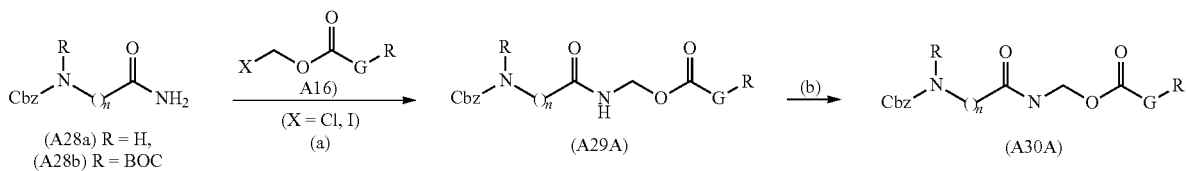

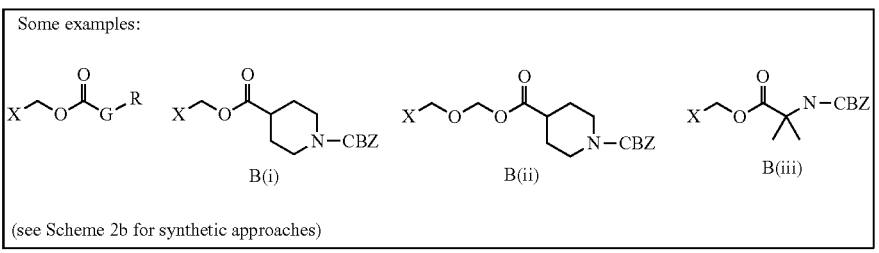

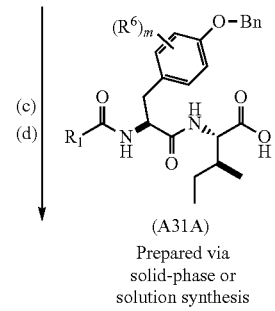

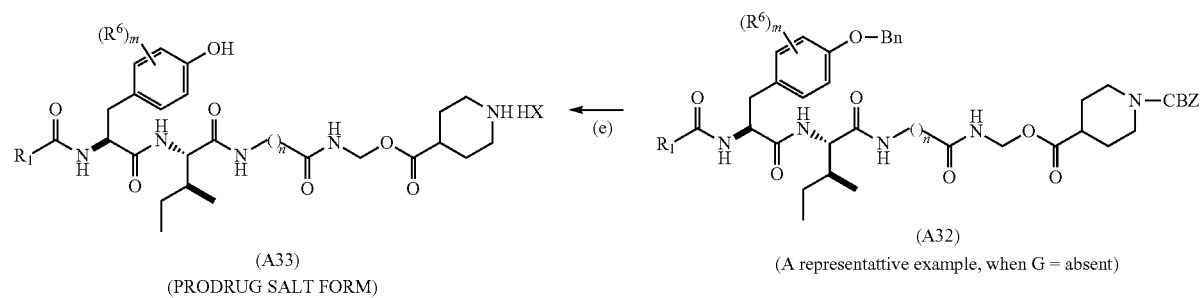

Reagents: (a) Cs₂CO₃, DMF, (b) 4M HCl/p-dioxane, (C) H2/Pd/c, (d) HATU, HBOT, DMF or EDCl, HOBt, DMF, (e) H₂/Pd—C glac HOAc/aq. HCl (1-1.5 eq.)

One may also be able to prepare derivatives incorporating dual prodrug moieties, one at the Tyr and other at the C-terminal amide, or at R3/R4 bridge and at R2, or some combination of the chemistries described above. As an example, dual prodrug analogs from one of these approaches, and corresponding proposed synthetic route, is shown in Scheme IX, below.

Scheme IX

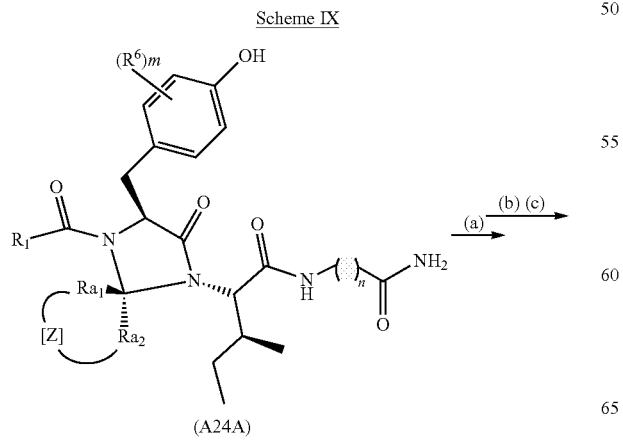

-continued

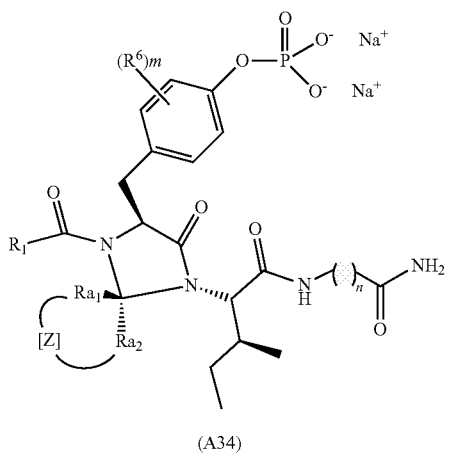

(a) (BnO)₂PO—O—PO(OBn)₂/ (non-aq) Base/DMF, (b) H₂/Pd—C, glac HOAc, (c) salt formation, (e.g. Ion-exchange resin)

Some Examples of (Cyclic Aminal) Imidazolidinone Fragments: CH(Ra)O

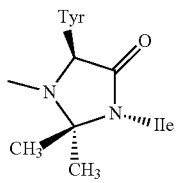
(A34a)

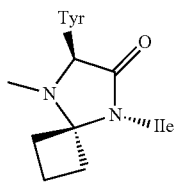
(A34b)

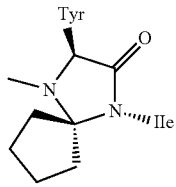
(A34c)

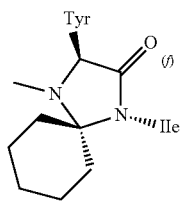
(A34d)

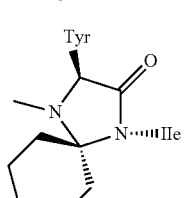
(A34e)

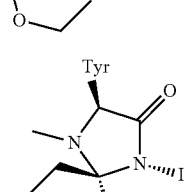
(A34f)

Furthermore, the tyrosine analogs with R6 variants such as F, $^2$H and CH$_3$ are reported in the published primary literature and/or in the patents and references cited therein. [For (R$_6$)$_m$ as $^2$H: 2,6-didetutero tyrosine, Nishiyama, B. et. al. J. Labeled Compounds and Radiopharmaceuticals, 1994, 34(9), 831-37; 2,3,4,6-tetradeutero tyrosine: Walker, T. E. et al. al J. Org Chem. 1986, 51(8), 1775-79; for (R$_6$)$_m$ as CH3: 2-methyl tyrosine, Schmidt, E. W. Tett. Letters, 2004, 3921-24; for 2,3-dimethyl tyrosine or 2,5-dimethyl tyrosine, Santagada, V. J. Med. Chem. 2006, 49(6), 1882-90, for 2,6-dimethyl tyrosine EP1481965A1 (2004) and EP2959918A1 (2015); and for (R$_6$)$_m$ as F: 2,6- or 2,3- or 2,4-difluoro and/or 2,3,5- or 2,3,6-trifluoro tyrosine, Seyedsayamdost, H. et. al. J. Am. Chem. Soc 2006, 49(6), 1882-90; and 2,3,5,6-tetrafuloro tyrosine is commercially available.] In addition, the derivative of A2 where R6 is 2-fluoro, such derivatives should be accessible via regiospecific electrophilic fluorination of the tyrosine-containing peptide or peptide mimetics utilizing in-situ generated CH$_3$COOF, as described by Hebel, D., Tett. Letters, 1990, 31(5), 619-622. Other such R6 derivatives should be accessible from extension of these chemistries.

The following specific, non-limiting examples are illustrative of the invention.

Example-1A

To a mixture of 4-nitrophenyl phosphorodichloridate (504 mg, 1.98 mmol) in THF (30 mL) at 0° C. was added, 2-(dimethylamino)ethanol (397 μL, 3.97 mmol) and stirred for two hours at room temperature. THF was evaporated and crude product was dissolved in DMF (20 mL) followed by addition of Base Structure (500 mg, 0.992 mmol) and LiOH.H$_2$O (208 mg, 4.96 mmol) and the mixture was stirred at room temperature overnight. Quenched with 4 Molar HCl, concentrated, washed (DCM/CH$_3$CN), and purified by preparative HPLC using Isocratic 40% MeOH vs 60% aqueous formic acid solution (0.1%), pure fractions were combined, (HCl Salt was formed by addition of 4 Molar HCl) to give the title compound, as a white solid, after lyophilization. [(obs) MH$^+$=727.5]

Example-1B

Step-1: A mixture of Base Structure (500 mg, 0.992 mmol) in DMF, tetrabenzyl diphosphate (587 mg, 1.09 mmol) and LiOH.H$_2$O (46 mg, 1.09 mmol) was stirred at room temperature overnight. Concentrated, washed (DCM) and used in the next step without further purification.

Step-2: 4-((S)-3-((2S,3S)-1-(6-amino-6-oxohexylamino)-3-methyl-1-oxopentan-2-ylamino)-2-hexanamido-3-oxopropyl)phenyl dibenzyl phosphate was dissolved in acetic acid (15 mL) and 10% Pd/C 0.5 eq (w/w) was added and stirred for two hours under hydrogen atmosphere. Reaction mixture was filtered through a pad of celite. Filtrate was concentrated, washed (DCM) and purified by preparative HPLC (Isocratic 70% MeOH vs 30% ammonium acetate buffer (pH 8) to give the desired compound after lyophilization as a white solid ($NH_4^+$ Salt). [(obs) $MH^+$=684.5]

Example-1C

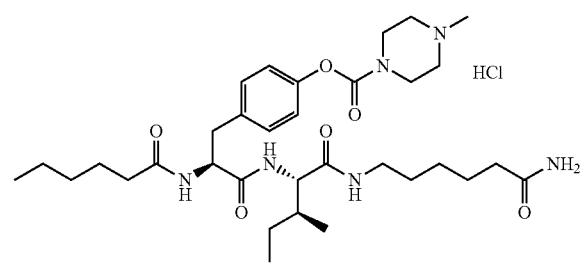 [SMILES: CCCCCC(=O)N[C@@H](Cc1ccc(OC(=O)N2CCN(C)CC2)cc1)C(=O)N[C@H](C(=O)NCCCCCC(N)=O)[C@@H](C)CC ; Cl]

Base Structure (564.9 mg, 1.119 mmol) was dissolved in dry DMF (12 mL) then $LiOH.H_2O$ (46.9 mg, 1.119 mmol) and bis(4-nitrophenyl)carbonate (374.6 mg, 1.231 mmol) were added. The solution was stirred at room temperature under nitrogen atmosphere for 17 h. N-methylpiperazine hydrochloride (198.8 mg, 1.455 mmol) was added and the mixture stirred for another 6 h then quenched with HCl and concentrated to dryness. The solid was washed (DCM, EtOAc) then purified by Biotage C-18 reverse phase flash chromatography (30%-100% MeOH vs 0.1% aqueous formic acid) to give the title compound Base Structure-C-PIPM (227.6 mg, 30%) after treatment with HCl and lyophilization. [(obs) $MH^+$=631.4 and $M+Na^+$=653.4]

Example-1D

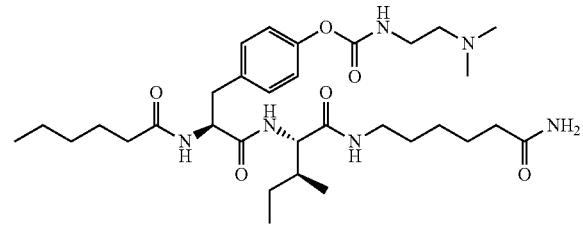 [SMILES: CCCCCC(=O)N[C@@H](Cc1ccc(OC(=O)NCCN(C)C)cc1)C(=O)N[C@H](C(=O)NCCCCCC(N)=O)[C@@H](C)CC]

Base Structure (508.1 mg, 1.007 mmol) was dissolved in dry DMF (8 mL) then $LiOH.H_2O$ (42.2 mg, 1.007 mmol) and bis(4-nitrophenyl)carbonate (336.9 mg, 1.107 mmol) were added. The solution was stirred at room temperature under nitrogen atmosphere overnight. N,N-dimethylethane-1,2-diamine hydrochloride (163.1 mg, 1.309 mmol) was added and the mixture stirred for another 4 h then quenched with HCl and concentrated to dryness. The solid was washed (DCM, EtOAc) then purified by preparative HPLC (50%-70% MeOH vs 0.1% aqueous formic acid) to give the title compound (154.8 mg, 12%) after treatment with HCl and lyophilization. [(obs) $MH^+$=619.5 and $M+Na^+$=641.6]

Example-1E

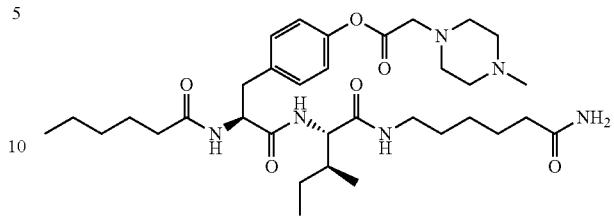

To a solution of Base Structure (200 mg; 0.39 mmol) and 2-(4-methylpiperazin-1-yl)acetic acid (175.6 mg; 1.1 mmol) in anhydrous DMF (15 mL), EDC HCl (247.3 mg; 1.3 mmol) and HOBt (61 mg; 039 mmol) were added at 0° C. The mixture was warmed to room temperature and stirred overnight. The reaction was quenched with 4M HCl in 1,4-dioxane (0.5 mL). The solvent was evaporated in vacuum and the solid material was dissolved in methanol (2 mL). Product was precipitated by adding diethylether to the above solution, and was separated by filtration. Crude product was purified by reverse phase HPLC using methanol (B): 0.1% formic acid in water (D), [gradient elution; 10 to 100% of B vs D in 20 min]. The combined fractions were acidified with HCl and lyophilized to offer the compound (206 mg, 82%) as white solid. [(obs) $MH^+$=645.4]

Example-1F

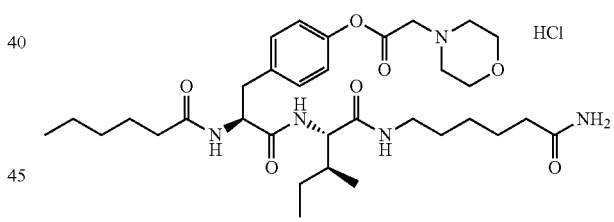

Step-1: A mixture of 2-morpholinoacetic acid (975 mg, 6.73 mmol), 4-nitrophenol (850 mg, 6.12 mmol), DCC (1386 mg, 6.73 mmol) and DMAP (40 mg, 0.306 mmol) in DCM (50 mL) was stirred at room temperature overnight. Reaction mixture was filtered, concentrated and washed with DCM gave 4-nitrophenyl 2-morpholinoacetate as a white solid which was used in the next step without further purification.

Step-2: A mixture of 4-nitrophenyl 2-morpholinoacetate (288 mg, 0.95 mmol), Base Structure (400 mg, 0.79 mmol), and $LiOH.H_2O$ (74 mg, 1.75 mmol) in DMF (10 mL) was stirred at room temperature overnight. Quenched with 4 molar HCl, Concentrated and washed ($DCM/THF/CH_3CN$) gave the desired compounds as a white solid (HCl Salt). [(obs) $MH^+$=632.5, $M+Li^+$=638.5]

Example-1 G

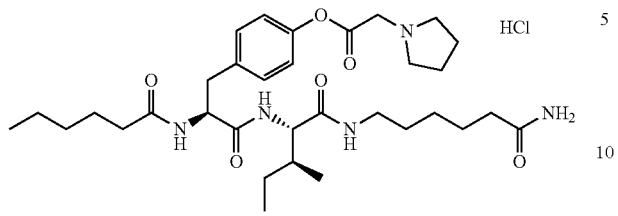

Step-1: A mixture of 2-(pyrrolidin-1-yl)acetic acid hydrochloride (1000 mg, 6.06 mmol), 4-nitrophenol (842 mg, 6.06 mmol), DCC (1500 mg, 7.27 mmol) and DMAP (39 mg, 0.30 mmol) in CH$_3$CN (50 mL) was stirred at room temperature overnight. Reaction mixture was filtered, concentrated and washed with DCM gave 4-nitrophenyl 2-(pyrrolidin-1-yl)acetate hydrochloride as yellow viscous oil which was used in the next step without further purification.

Step-2: A mixture of 4-nitrophenyl 2-(pyrrolidin-1-yl) acetate hydrochloride (187 mg, 0.66 mmol), Base Structure (300 mg, 0.59 mmol), and LiOH.H$_2$O (55 mg, 1.31 mmol) in DMF (10 mL) was stirred at room temperature overnight. Quenched with 4 molar HCl, concentrated, washed (DCM/CH$_3$CN) and purified by preparative HPLC using isocratic 40% MeOH and 60% 0.1% aqueous formic acid solution gave the desired compounds as a white solid 4 molar HCl was added to make HCl Salt of the final product) after lyophilization. [(obs) MH$^+$=616.5 and M+Na$^+$=638.4]

Example-1H

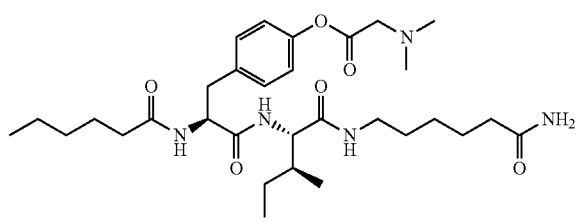 [SMILES: CCCCCC(=O)N[C@@H](Cc1ccc(OC(=O)CN(C)C)cc1)C(=O)N[C@H](C(=O)NCCCCCC(N)=O)[C@@H](C)CC]

To a solution of Base Structure (200 mg; 0.39 mmol) and 2-(dimethylamino) acetic acid (124.4 mg; 1.1 mmol) in anhydrous DMF (15 mL), EDC HCl (191.7 mg; 1 mmol) and HOBt (61.2 mg; 0.39 mmol) were added at 0° C. The mixture was warmed to room temperature and stirred overnight. The reaction was quenched with 4M HCl in 1,4-dioxane (0.5 mL). The solvent was evaporated in vacuum and the solid material was dissolved in methanol (2 mL). Product was precipitated by adding diethylether to the above solution, and was separated by filtration. The crude product was purified by reverse phase HPLC using methanol (B): 0.1% formic acid in water (D), [gradient elution; 10 to 100% of B vs D in 20 min]. The combined fractions were acidified with HCl and lyophilized to offer as white solid (94 mg 40%). In addition, 63 mg of Base Structure was also recovered from this reaction. [(obs) MH$^+$=590.4 and M+Na$^+$=612.4]

Example-1I

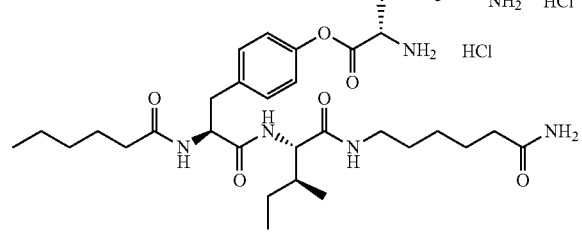

Step-1: A mixture of Boc-(S)-Lys(Boc)-OH (741 mg, 2.14 mmol), 4-nitrophenol (282.7 mg, 2.03 mmol), DCC (441.3 mg, 2.14 mmol) and DMAP (26.1 mg, 0.214 mmol) in dry acetonitrile (20 mL) was stirred at room temperature under nitrogen atmosphere overnight. Reaction mixture was filtered, concentrated and crude product was purified by flash chromatography (silica gel, hexanes/EtOAc) to provide (S)—4-nitrophenyl 2,6-bis(tert-butoxycarbonylamino) hexanoate (548.7 mg, 55%).

Step-2: (S)—4-nitrophenyl 2,6-bis(tert-butoxycarbonylamino)hexanoate (512.0 mg, 1.095 mmol) in solution in dry DMF (5 mL) was added to a solution of Base Structure (460.6 mg, 0.9127 mmol) and LiOH.H$_2$O (40.2 mg, 0.958 mmol). The mixture was stirred at room temperature under nitrogen atmosphere overnight. Concentration and washing (DCM, acetonitrile) gave bis(Boc-protected)—(578.2 mg, 76%).

Step-3: Bis(Boc-protected)—(307.1 mg, 0.369 mmol) was stirred in a DMF (1.5 mL)/4N HCl in dioxane (8 mL) mixture at room temperature for 3.5 h then concentrated, washed (DCM) and purified by preparative HPLC (40%-100% MeOH vs 0.1% aqueous formic acid), after treatment with HCl and lyophilisation provided the title compound (204.1 mg, 68%). [(obs) MH$^+$=633.5 and M+Na$^+$=655.6]

Example-1J

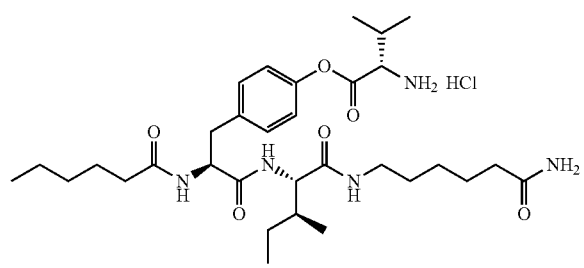 [SMILES: CCCCCC(=O)N[C@@H](Cc1ccc(OC(=O)[C@@H](N)C(C)C)cc1)C(=O)N[C@H](C(=O)NCCCCCC(N)=O)[C@@H](C)CC ; Cl]

Step-1: To a solution of 4-nitrophenol (1 g, 7.2 mmol) and (S)—2-(tert-butoxycarbonylamino)-3-methylbutanoic acid (1.8 g, 8.6 mmol) in anhydrous acetonitrile (25 mL), was added DCC (1.8 g, 8.6 mmol) and DMAP (44 mg, 0.36 mmol). The mixture was stirred overnight under nitrogen atmosphere. The solvent evaporated in vacuum and crude mixture was purified by normal phase column chromatography using DCM (100%) as eluent to offer (S)—4-nitrophenyl-2-(tert-butoxycarbonylamino)-3-methylbutanoate (0.7 g, 29%).

(S)—4-nitrophenyl-2-(tert-butoxycarbonylamino)-3-methylbutanoate and Base Structure (300 mg; 0.59 mmol) was dissolved in anhydrous DMF (25 mL). LiOH $H_2O$ (24.9 mg, 0.59 mmol) was added to the solution. The mixture was stirred at room temperature under nitrogen atmosphere overnight. The solvent was evaporated in vacuum, solid material was washed with DCM (100%) and then acetonitrile (100%) to offer pure BOC-protected-product (300 mg), which was dissolved in a mixture of DMF (3 mL) and 1,4-dioxane (1 mL). 4 M HCl in 1,4-dioxane (10 mL) was added to the above solution. The mixture was stirred at room temperature for 4 h. The solvent was evaporated in vacuum and the crude product was purified by reverse phase HPLC using methanol (B): 0.1% formic acid in water (D), [gradient elution; 40 to 100% of B vs D in 20 min]. The combined fractions were acidified with HCl and lyophilized to offer the compound (180 mg, 50%) as white solid. [(obs) $MH^+$=604.4, $M+Na^+$=626.5]

6.2. Example 2: Stability in Simulated Intestinal Fluid, Simulated Gastric Fluid, and Plasma|Permeability Experiments were conducted to assess the metabolic stability of test compounds in the simulated intestinal fluid (SIF), simulated gastric fluid (SGF), and plasma.

Plasma Stability Study
Assay Conditions
[Compound]=1 µM
Time=0, 60, 120, and 240 min
Temperature=37° C.
Experimental Protocol
Human and rat plasma (K2 EDTA) were obtained from Bioreclamation.

Compounds were dissolved as 0.3 mM DMSO stocks. Compounds were transferred to the plasma at 1 µM on a 96-well deep well plate. After mixing, samples were transferred to several 96-well plates (25 L/well), and incubated at 37° C. The extent of metabolism was calculated as the disappearance of the test compound, compared to the 0-min control reaction incubations. Propantheline was included as a positive control to verify assay performance.

At each of the time points, 150 µL of quench solution (50% acetonitrile, 50% methanol with 0.05% formic acid) with internal standard (bucetin for positive ESI mode and warfarin for negative ESI mode) was transferred to each well. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed in the table below.

TABLE 1

| Gradient Conditions | | | |
|---|---|---|---|
| Time (min) | Flow (µL/min) | % A | % B |
| 0 | 500 | 98 | 2 |
| 0.30 | 500 | 98 | 2 |
| 1.40 | 500 | 2 | 98 |
| 2.00 | 500 | 2 | 98 |
| 2.01 | 500 | 98 | 2 |
| 2.50 | 500 | 98 | 2 |

Initial rates of the clearance of test compounds were calculated using linear regression of semi-log plot of % remaining of compounds versus time. The elimination rate constant (equals to −slope) of the linear regression was then used to determine t1/2 values.

Metabolic Stability in SIF and SGF (Simulated Intestinal and Gastric Fluid)

Assay Conditions

[Drug]=5 µM

Buffer 1=SGF without enzyme

Buffer 2=SGF with 0.32% pepsin

Buffer 3=SIF without enzyme

Buffer 4=SIF with 1% pancreatin

Time=0, 60, 120, and 240 min

Temperature=37° C.

Experimental Protocol

SIF was prepared freshly with 8.7 mM NaOH, 28.65 mM NaH2PO4, 105.85 mM NaCl, with a final pH of 6.8. SGF was prepared freshly with 34.2 mM NaCl, with a final pH of 1.2. Enzymes such as pepsin or pancreatin were added to some buffers. Human and rat plasma (K2 EDTA) were purchased from BioreclamationIVT.

Compounds were dissolved as 1.5 mM DMSO stocks. Compounds were transferred to SIF, SGF, or plasma at 5 µM on a 96-well deep well plate. After mixing, samples were transferred to several 96-well plates (25 µL/well), and incubated at 37° C. The extent of metabolism was calculated as the disappearance of the test compound, compared to the 0-min control reaction incubations. Candesartan Cilexetil and omeprazole were included as positive controls for SIF and SGF, respectively, to verify assay performance.

At each of the time points, 150 µL of quench solution (100% acetonitrile with 0.1% formic acid) with internal standard (bucetin for positive ESI mode and warfarin for negative ESI mode) was transferred to each well. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed in the table below.

TABLE 1

Gradient Conditions

| Time (min) | Flow (μL/min) | % A | % B |
|---|---|---|---|
| 0 | 500 | 98 | 2 |
| 0.30 | 500 | 98 | 2 |
| 1.40 | 500 | 2 | 98 |
| 2.00 | 500 | 2 | 98 |
| 2.01 | 500 | 98 | 2 |
| 2.50 | 500 | 98 | 2 |

Initial rates of the clearance of test compounds were calculated using linear regression of semi-log plot of % remaining of compounds versus time. The elimination rate constant (equals to −slope) of the linear regression was then used to determine t1/2 values.

Permeability Study

Caco Experiment Methods

Assay Conditions

[Compound]=10 μM

[GF120918]=0 or 10 μM

Buffer=HBSS, pH 7.4 with 5 mM HEPES

Time=1 hr

Controls=Digoxin

Experimental Protocol

Caco-2 cell plates were obtained commercially and were maintained for 21 days at 37° C. with 5% $CO_2$. Cells were washed with Hank's Balanced Salt Solution (HBSS) 30 min before starting the experiment. Test compound solutions were prepared by diluting from DMSO stock into HBSS buffer in the presence or absence of 10 μM of P-gp inhibitor GF120918. The final DMSO concentration is 0.2%. Prior to each experiment, cell monolayer integrity was verified by transendothelial electrical resistance (TEER). Transport experiment was initiated by adding test compounds to the apical (75 μL) side. Transport plates were incubated at 37° C. in a humidified incubator with 5% $C_{O2}$. Samples were taken from the donor and acceptor compartments after 1 hr and analyzed by liquid chromatography with tandem mass spectrometry (LC/MS/MS).

Apparent permeability (Papp) values were calculated using the following equation:

$$Papp=(dQ/dt)/A/C_0$$

where dQ/dt is the initial rate of amount of test compound transported across cell monolayer, A is the surface area of the filter membrane, and $C_0$ is the initial concentration of the test compound. $C_0$ is calculated for each condition using a 4-point calibration curve. To calculate Papp each pro-drug and MM-201 were monitored simultaneously and the concentrations were added up to determine the final compound concentration in the system.

Absorption quotient between the two assay conditions was calculated by the following equation:

$$\text{Absorption quotient (AQ)}=(Papp,\text{A-B with inhibitor}-Papp,\text{A-B without inhibitor})/Papp,\text{A-B with inhibitor}$$

where Papp, A-B with inhibitor and Papp, A-B without inhibitor represent the apparent permeability of test compound from the apical to basal side of the cellular monolayer in the presence and absence of 10 μM P-gp inhibitor GF 120918, respectively.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (10 mm×2.1 mm) at a flow rate of 0.5 mL/min. The mobile phase consisted of 0.1% formic acid in water (solvent A) and 0.1% formic acid in acetonitrile (solvent B).

TABLE 1

Gradient Conditions

| Time (min) | Flow (μL/min) | % A | % B |
|---|---|---|---|
| 0 | 500 | 98 | 2 |
| 0.30 | 500 | 98 | 2 |
| 1.40 | 500 | 2 | 98 |
| 2.00 | 500 | 2 | 98 |
| 2.01 | 500 | 98 | 2 |
| 2.50 | 500 | 98 | 2 |

6.3. Example 3: In-Vivo Pharmacokinetics

Methods and Materials:

1. Eighy (8) male JVC SD rats (purchased from Charles River Lab) were monitored daily for body condition and health status during the 3-5 days acclimation period. The rats were randomly assigned into one group (n=4).

2. On Day 1,

Rats are weighed and PO dosed with

Group 1: 13.2 mg/kg of A20 (10 mL/kg of 1.32 mg/mL)

Group 2: 14.2 mg/kg of A22 (10 mL/kg of 1.42 mg/mL).

3. The dosed rats were individually placed into a metabolic cage, and have access to food and water at all times. The urine from each rat was collected daily from the metabolic cages, and kept in dry ice.

4. At predose (0 min), 5 min, 15 min, 30 min, 1 hr, 2 hr, 8 hr, and 24 hr post dosing, approximately 200 ul blood samples were collected from each rat and transferred to EDTA tubes.

5. The blood samples in EDTA vials were centrifuged at 4° C. and 6,000 rpm for 10 minutes to generate ~100 μl of plasma per sample. Blood samples were processed as quickly as possible and remain no longer than 2 min at room temperature and no longer than 15 minutes at 4° C. prior to processing.

6. All samples were transferred for bioanalytic assay using LCMS
Data for each study are shown below:
| Compound ID | Structure |
|---|---|
| Base Structure | N-hexanoic-L-tyrosine-L-isoleucine-(6)-aminohexanoic amide |//
A26
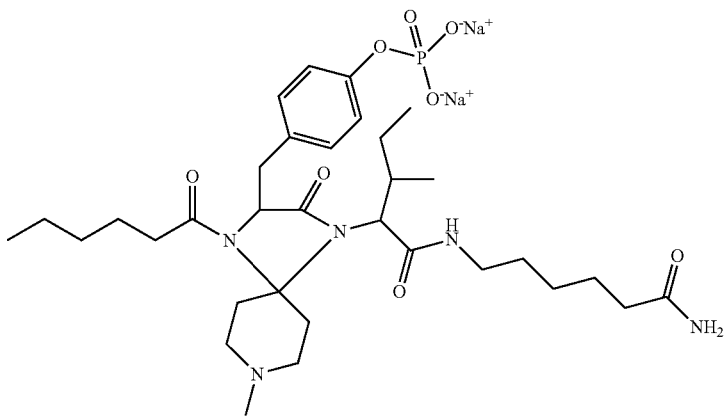
2
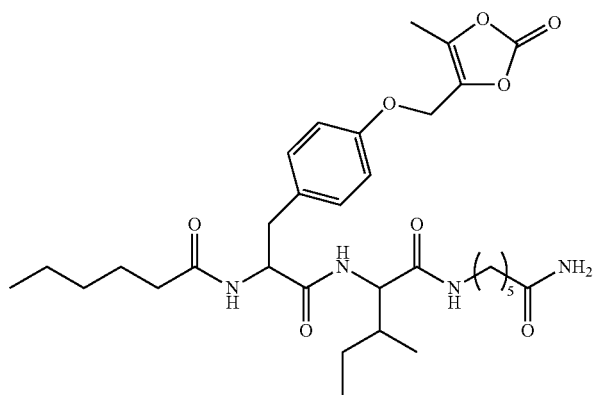
A28

-continued
| Compound ID | Structure |
|---|---|
| A18 | 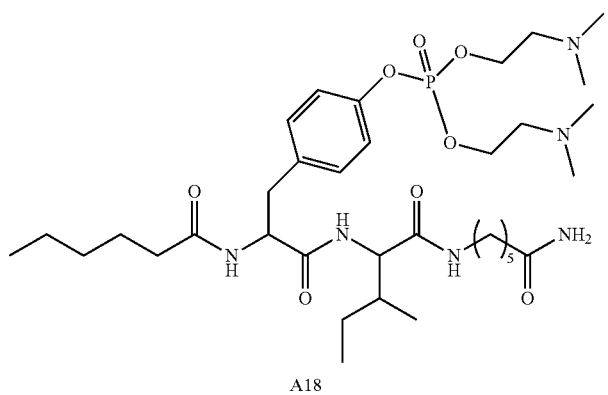 A18 |
| A29 | 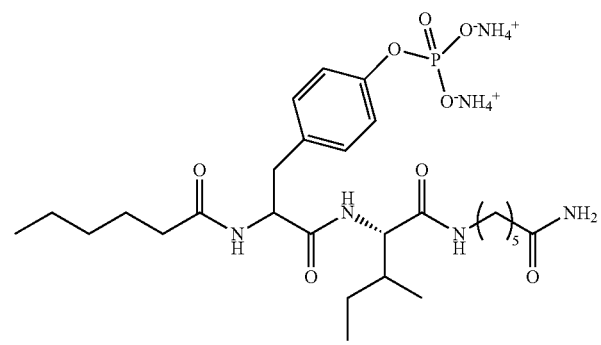 |
| A30 | 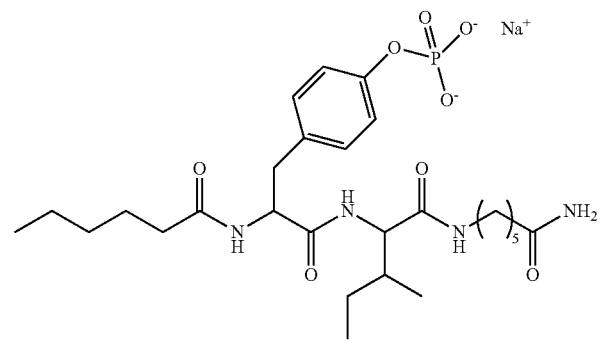 |
| A20 | 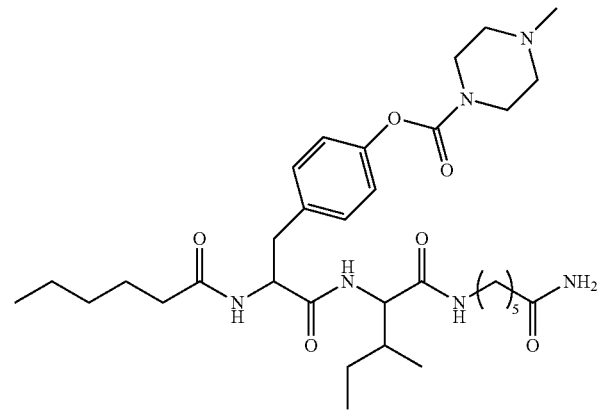 |

-continued
| Compound ID | Structure |
|---|---|
| A21 | 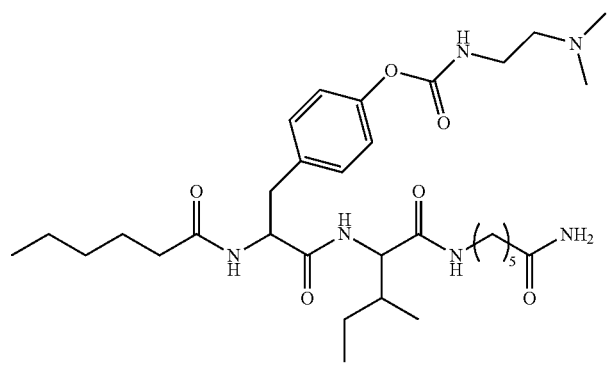 |
| A22 | 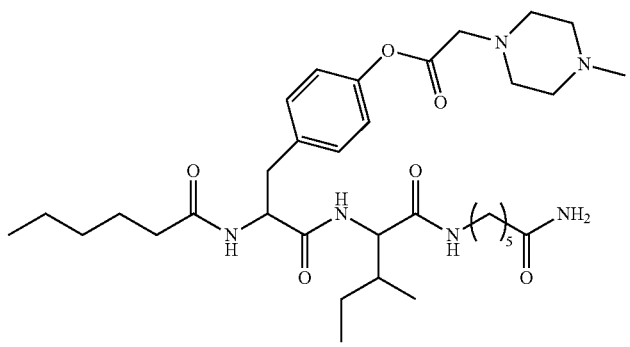 |
| A23 | 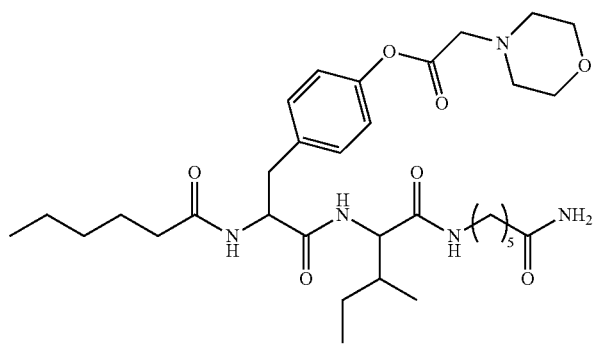 |
| A24 | 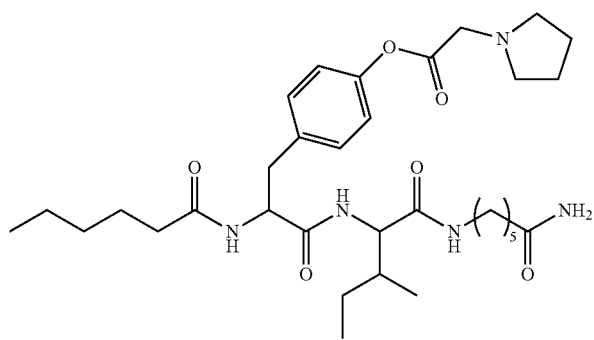 |

| Compound ID | Structure |
|---|---|
| A25 | 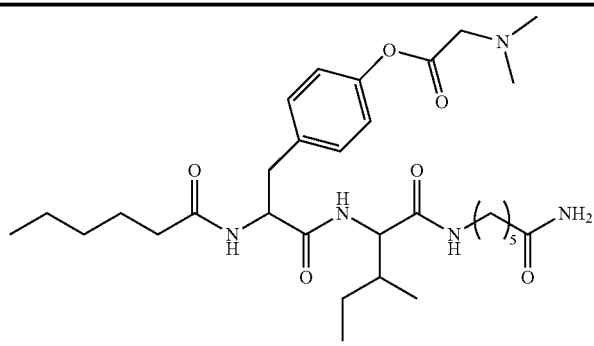 |
| A26 | 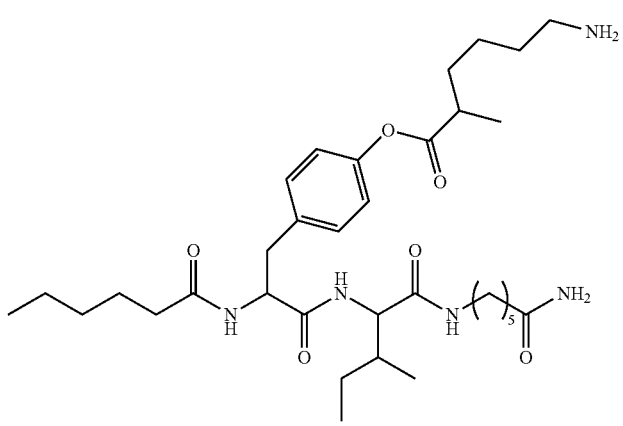 |
| A27 | 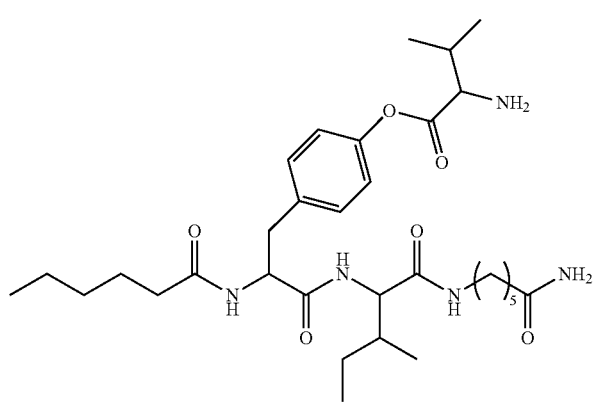 |
| | Plasma Stability (% Parent Remaining) | | | | | | | | |
|---|---|---|---|---|---|---|---|---|---|
| | Human Plasm | | | | Rat Plasma | | | | |
| Compound ID | 0 min | 60 min | 120 min | 240 min | Half-Life (min) | 0 min | 60 min | 120 min | 240 min | Half-Life (min) |
| Base Structure | 100% | 98% | 102% | 98% | 12558.0 | 100% | 87% | 89% | 83% | 1095.1 |
| A26 | 100% | 106% | 123% | 109% | NA | 100% | 112% | 117% | 111% | NA |
| 2 | 100% | 113% | 90% | 72% | 424.5 | 100% | 82% | 77% | 83% | 1083.6 |
| A28 | — | — | — | — | — | — | — | — | — | — |
| A18 | — | — | — | — | — | — | — | — | — | — |
| A29 | — | — | — | — | — | — | — | — | — | — |
| A30 | 100% | 36% | 20% | 12% | 84.2 | 100% | 88% | 87% | 86% | 1307.4 |
| A20 | 100% | 83% | 87% | 90% | 2957.7 | 100% | 73% | 56% | 34% | 157.0 |

Plasma Stability (% Parent Remaining)

| | Human Plasm | | | | | Rat Plasma | | | | |
| --- | --- | --- | --- | --- | --- | --- | --- | --- | --- | --- |
| Compound ID | 0 min | 60 min | 120 min | 240 min | Half-Life (min) | 0 min | 60 min | 120 min | 240 min | Half-Life (min) |
| A21 | 100% | 59% | 33% | 11% | 73.4 | 100% | 61% | 34% | 9% | 69.7 |
| A22 | 100% | 59% | 37% | 15% | 87.9 | 100% | 1% | 0% | 0% | 8.7 |
| A23 | 100% | 29% | 7% | 1% | 31.3 | 100% | 1% | 1% | 0% | 8.2 |
| A24 | 100% | 0% | 0% | 0% | 7.3 | 100% | 55% | 27% | 47% | 64.2 |
| A25 | 100% | 2% | 0% | 0% | 10.1 | 100% | 1% | 0% | 0% | 8.2 |
| A26 | 100% | 11% | 7% | 13% | 18.8 | 100% | 5% | 10% | 8% | 13.5 |
| A27 | 100% | 4% | 4% | 5% | 13.2 | 100% | 27% | 29% | 37% | 31.9 |

SIF Stability (pH 6.8)

| | −Pancreatin | | | | | +Pancreatin | | | | |
| --- | --- | --- | --- | --- | --- | --- | --- | --- | --- | --- |
| Compound ID | 0 min | 60 min | 120 min | 240 min | Half-Life (min) | 0 min | 60 min | 120 min | 240 min | Half-Life (min) |
| BASE STRUCTURE | 100% | 119% | — | 113% | Neg. | — | — | — | — | — |
| A26 | Not in report | Not in report | Not in report | Not in report | Not in report | Not in report | Not in report | Not in report | Not in report | Not in report |
| 2 | 100% | 82% | 82% | 78% | 801.5 | 100% | 94% | 51% | 34% | 142.4 |
| A28 | | | | | | | | | | |
| A18 | 100% | 25% | 17% | 8% | 30.2 | 100% | 40% | 12% | 25% | 39.4 |
| A29 | 100% | 96% | 97% | 103% | Neg. | 100% | 94% | 98% | 104% | Neg. |
| A30 | 100% | 43% | 22% | 8% | 68.4 | 100% | 70% | 51% | 34% | 156.6 |
| A20 | 100% | 65% | 57% | 51% | 95.4 | 100% | 62% | 54% | 61% | 86.6 |
| A21 | — | — | — | — | — | 100% | 95% | 97% | 93% | 3006.4 |
| A22 | 100% | 74% | 61% | 59% | 335.8 | 100% | 69% | 64% | 63% | 425.9 |
| A23 | 100% | 93% | 95% | 79% | 744.0 | 100% | 66% | 41% | 20% | 104.5 |
| A24 | 100% | 62% | 38% | 14% | 83.5 | 100% | 13% | 1% | 0% | 18.8 |
| A25 | — | — | — | — | — | 100% | 27% | 7% | 1% | 34.7 |
| A26 | 100% | 11% | 1% | 0% | 19.6 | 100% | 78% | 52% | 37% | 166.9 |
| A27 | 100% | 63% | 59% | 24% | 122.6 | 100% | 49% | 24% | 5% | 57.1 |

SGF Stability (pH 1.2)

| | −Pepsin | | | | | +Pepsin | | | | |
| --- | --- | --- | --- | --- | --- | --- | --- | --- | --- | --- |
| Compound ID | 0 min | 60 min | 120 min | 240 min | Half-Life (min) | 0 min | 60 min | 120 min | 240 min | Half-Life (min) |
| BASE STRUCTURE | 100% | 127% | — | 122% | Neg. | 100% | 13% | — | 0.2% | 26.0 |
| A26 | Not in report | Not in report | Not in report | Not in report | Not in report | Not in report | Not in report | Not in report | Not in report | Not in report |
| 2 | 100% | 84% | 78% | 67% | 430.2 | 100% | 94% | 89% | 73% | 517.4 |
| A28 | — | — | — | — | — | — | — | — | — | — |
| A18 | 100% | 51% | 14% | 15% | 42.6 | 100% | 52% | 17% | 18% | 46.4 |
| A29 | 100% | 117% | 129% | 123% | Neg. | 100% | 86% | 63% | 49% | 225.0 |
| A30 | 100% | 95% | 98% | 89% | 1713.6 | 100% | 95% | 64% | 54% | 248.3 |
| A20 | 100% | 70% | 57% | 60% | 116.5 | 100% | 57% | 37% | 26% | 84.5 |
| A21 | — | — | — | — | — | 100% | 87% | 74% | 54% | 265.1 |
| A22 | 100% | 70% | 51% | 55% | 124.5 | 100% | 52% | 26% | 10% | 73.5 |
| A23 | 100% | 92% | 85% | 83% | 892.2 | 100% | 79% | 65% | 45% | 211.0 |
| A24 | 100% | 97% | 89% | 84% | 916.4 | 100% | 74% | 61% | 43% | 201.9 |
| A25 | — | — | — | — | — | 100% | 94% | 91% | 65% | 389.4 |
| A26 | 100% | 63% | 33% | 115% | 75.9 | 100% | 88% | 36% | 120% | 80.3 |
| A27 | 100% | 115% | 107% | 105% | Neg. | 100% | 102% | 95% | 71% | 449.7 |

| | Caco-2 Cells Permeability | | | | |
|---|---|---|---|---|---|
| | −GF120918 | | +GF120918 | | |
| Compound ID | $P_{app\ A-B}$ | Recovery Rate | $P_{app\ A-B}$ | Recovery Rate | Abs. Quotient |
| BASE STRUCTURE | 0.064 | 87% | 0.41 | 83% | 0.84 |
| A26 | 0.1 | 91% | 0.5 | 96% | 0.82 |
| 2 | — | — | — | — | — |
| A28 | — | — | — | — | — |
| A18 | 0.04 | 48% | 0.08 | 90% | 0.54 |
| A29 | 0.028 | 86% | 0.17 | 76% | 0.83 |
| A30 | — | — | — | — | — |
| A20 | 0.06 | 71% | 0.5 | 90% | 0.88 |
| A21 | 0.099 | 84% | 0.2 | 84% | 0.50 |
| A22 | 0.1 | 107% | 0.7 | 104% | 0.78 |
| A23 | 0.1 | 91% | 0.4 | 96% | 0.78 |
| A24 | 0.1 | 72% | 0.6 | 72% | 0.88 |
| A25 | 0.092 | 91% | 0.4 | 83% | 0.77 |
| A26 | 0.044 | 94% | 0.29 | 89% | 0.85 |
| A27 | 0.117 | 90% | 0.39 | 94% | 0.70 |

| | Rat PK (PO Route, 10 mg/kg Equiv., n = 4) Parent (BASE STRUCTURE) | | | | |
|---|---|---|---|---|---|
| Compound ID | "$AUC_{0-24}$ (ng · h/mL)" | "$AUC_{0-inf}$ (ng · h/mL)" | "Cmax (ng/mL)" | "Tmax (h)" | "Half-Life (h)" |
| BASE STRUCTURE | 0.4 ± 0.2 | — | 0.9 ± 0.5 | 0.4 ± 0.5 | — |
| A26 | — | — | — | — | — |
| 2 | — | — | — | — | — |
| A28 | — | — | — | — | — |
| A18 | 4.1 ± 3.8 | 6.8 ± 4 | 3.1 ± 2.5 | 0.2 ± 0.1 | 3.5 ± 2.6 |
| A29 | 35.9 ± 27.6 | 48.6 ± 26.5 | 39.7 ± 74.2 | 2.1 ± 4 | 15.7 ± 14.3 |
| A30 | | | | | |
| A20 | 0.8 ± 1 | 1.61 | 1.7 ± 1.3 | 0.3 ± 0 | 0.17 |
| A21 | 7.4 ± 0.9 | 47.8 ± 1 | 0.6 ± 0.1 | 0.9 ± 0.8 | 81.7 ± 5.7 |
| A22 | 25.1 ± 4.4 | 91.3 | 1.4 ± 0.1 | 15 ± 10.5 | 58.8 |
| A23 | 5.1 ± 1.4 | 12.4 ± 8.8 | 5.5 ± 6.2 | 0.2 ± 0.2 | 22.1 ± 17.1 |
| A24 | 0.4 ± 0.2 | 1.1 ± 0.9 | 0.3 ± 0.1 | 0.4 ± 0.4 | 5 ± 5.1 |
| A25 | 10.9 ± 4 | 31 ± 26.1 | 3.1 ± 3.5 | 0.3 ± 0.2 | 42.5 ± 49.9 |
| A26 | 14.1 ± 6.3 | 28 ± 12 | 6.8 ± 6.6 | 1.1 ± 1.9 | 8.9 ± 0.5 |
| A27 | 29.6 ± 35 | 9.0 | 2.8 ± 2.7 | 18.1 ± 11.8 | 13.4 |

| | Rat PK (PO Route, 10 mg/kg Equiv., n = 4) Prodrug | | | | |
|---|---|---|---|---|---|
| Compound ID | "AUC0-24 (ng · h/mL)" | "AUC0-inf (ng · h/mL)" | "Cmax (ng/mL)" | "Tmax (h)" | "Half-Life (h)" |
| BASE STRUCTURE | — | — | — | — | — |
| A26 | — | — | — | — | — |
| 2 | — | — | — | — | — |
| A28 | — | — | — | — | — |
| A18 | 4.9 ± 2.6 | — | 3.8 ± 0.1 | 1.5 ± 0.7 | — |
| A29 | 0 | 0 | 0 | 0 | 0 |
| A30 | | | | | |
| A20 | 0 | 0 | 0 | 0 | 0 |
| A21 | 2.8 ± 1.9 | 6.46 | 1.6 ± 0.5 | 0.8 ± 0.4 | 1.32 |
| A22 | 0 | 0 | 0 | 0 | 0 |
| A23 | 0 | 0 | 0 | 0 | 0 |
| A24 | 0.2 ± 0.1 | — | 0.5 ± 0.1 | 0.9 ± 0.3 | — |
| A25 | 91.2 ± 3.8 | 3709.5 | 4.2 ± 0.1 | 9.3 ± 10.2 | 667.8 |
| A26 | 0 | 0 | 0 | 0 | 0 |
| A27 | 0 | 0 | 0 | 0 | 0 |

| Parameter | Unit | Animal 1 | Animal 2 | Animal 3 | Animal 4 | Average | Std. Dev. | Combined |
|---|---|---|---|---|---|---|---|---|
| | | | BASE STRUCTURE (20 mg/kg) Dosed as Parent (Base Structure) | | | | | |
| 5 Lambda_z | 1/h | | | | | | | 0.4 ± 0.5 |
| 6 t1/2 | h | | | | | | | 0.9 ± 0.5 |
| 7 Tmax | h | 0.08 | 0.25 | 1 | | 0.4433333 | 0.4895236 | |
| 8 Cmax | ng/ml | 0.689 | 1.54 | 0.551 | | 0.9266667 | 0.5356252 | 0 ± 0 |
| 9 Tlag | h | 0 | 0 | 0 | | 0 | 0 | 0.8 ± 0.2 |
| 10 Clast_obs/Cmax | | 0.8577649 | 0.6 | 1 | | 0.819255 | 0.2027616 | 0.4 ± 0.2 |
| 11 AUC 0-t | ng/ml*h | 0.61636 | 0.517525 | 0.206625 | | 0.4468367 | 0.2138184 | |
| 12 AUC 0-inf_obs | ng/ml*h | | | | | | | |
| 13 AUC 0-t/0-inf_obs | | | | | | | | |
| 14 AUMC 0-inf_obs | ng/ml*h^2 | | | | | | | |
| 15 MRT 0-inf_obs | h | | | | | | | |
| 16 Vz/F_obs | (mg/kg)(ng/ml) | | | | | | | |
| 17 Cl/F_obs | (mg/kg)(ng/ml)/h | | | | | | | |
| | | | | Prodrug | | | | |
| 21 Lambda_z | 1/h | | | | | | | |
| 22 t1/2 | h | | | | | | | |
| 23 Tmax | h | | | | | | | |
| 24 Cmax | ng/ml | | | | | | | |
| 25 Tlag | h | | | | | | | |
| 26 Clast_obs/Cmax | | | | | | | | |
| 27 AUC 0-t | ng/ml*h | | | | | | | |
| 28 AUC 0-inf_obs | ng/ml*h | | | | | | | |
| 29 AUC 0-t/0-inf_obs | | | | | | | | |
| 30 AUMC 0-inf_obs | ng/ml*h^2 | | | | | | | |
| 31 MRT 0-inf_obs | h | | | | | | | |
| 32 Vz/F_obs | (mg/kg)(ng/ml) | | | | | | | |
| 33 Cl/F_obs | (mg/kg)(ng/ml)/h | | | | | | | |
| | | Dosed as A18 (10 mg/kg equivalent of Base Structure) Parameters for Parent (Base Structure) following dosing of A18 | | | | | | |
| 38 Lambda_z | 1/h | 0.3302821 | 1.5184227 | 0.123071 | 0.1201033 | 0.5229698 | 0.6708888 | 0.5 ± 0.7 |
| 39 t1/2 | h | 2.0986519 | 0.4564916 | 5.6320917 | 5.7712605 | 3.4896239 | 2.641384 | 3.5 ± 2.6 |
| 40 Tmax | h | 0.25 | 0.08 | 0.08 | 0.25 | 0.165 | 0.0981495 | 0.2 ± 0.1 |
| 41 Cmax | ng/ml | 1.3 | 3.37 | 1.27 | 6.62 | 3.14 | 2.5196428 | 3.1 ± 2.5 |
| 42 Tlag | h | 0 | 0 | 0 | 0 | 0 | 0 | 0 ± 0 |
| 43 Clast_obs/Cmax | | 0.4638462 | 0.0836795 | 0.7102362 | 0.026284 | 0.3210115 | 0.3240825 | 0.3 ± 0.3 |
| 44 AUC 0-t | ng/ml*h | 1.663875 | 3.218 | 1.90263 | 9.77745 | 4.1404888 | 3.8195962 | 4.1 ± 3.8 |
| 45 AUC 0-inf_obs | ng/ml*h | 3.4895869 | 3.403719 | 9.2317325 | 11.226203 | 6.8378105 | 3.999685 | 6.8 ± 4 |
| 46 AUC 0-t/0-inf_obs | | 0.4768114 | 0.9454364 | 0.2060967 | 0.8709489 | 0.6248234 | 0.3467035 | 0.6 ± 0.3 |
| 47 AUMC 0-inf_obs | ng/ml*h^2 | 10.678131 | 2.5861986 | 76.049072 | 97.479622 | 46.698256 | 47.200073 | 46.7 ± 47.2 |
| 48 MRT 0-inf_obs | h | 3.0599986 | 0.7598155 | 8.2377898 | 8.6832225 | 5.1852066 | 3.9010672 | 5.2 ± 3.9 |
| 49 Vz/F_obs | (mg/kg)(ng/ml) | 8.6764271 | 1.9348781 | 8.8015882 | 7.4167273 | 6.7074052 | 3.2425711 | 6.7 ± 3.2 |
| 50 Cl/F_obs | (mg/kg)(ng/ml)/h | 2.8656687 | 2.9379628 | 1.0832203 | 0.8907731 | 1.9444062 | 1.1087024 | 1.9 ± 1.1 |
| | | | | Data for Prodrug A18 | | | | |
| 54 Lambda_z | 1/h | — | — | | | | | |
| 55 t1/2 | h | — | — | | | | | |
| 56 Tmax | h | 2 | 1 | | | 1.5 | 0.7071068 | 1.5 ± 0.7 |

-continued

| | Parameter | Unit | Animal 1 | Animal 2 | Animal 3 | Animal 4 | Average | Std. Dev. | Combined |
|---|---|---|---|---|---|---|---|---|---|
| 57 | Cmax | ng/ml | 3.84 | 3.68 | | | 3.76 | 0.1131371 | 3.8 ± 0.1 |
| 58 | Tlag | h | 0 | 0 | | | 0 | 0 | 0 ± 0 |
| 59 | Clast_obs/Cmax | | 1 | 1 | | | 1 | 0 | 1 ± 0 |
| 60 | AUC 0-t | ng/ml*h | 6.8 | 3.09875 | | | 4.949375 | 2.617179 | 4.9 ± 2.6 |
| 61 | AUC 0-inf_obs | ng/ml*h | — | — | | | | | |
| 62 | AUC 0-t/0-inf_obs | | — | — | | | | | |
| 63 | AUMC 0-inf_obs | ng/ml*h^2 | — | — | | | | | |
| 64 | MRT 0-inf_obs | h | — | — | | | | | |
| 65 | Vz/F_obs | (mg/kg)/(ng/ml) | — | — | | | | | |
| 66 | Cl/F_obs | (mg/kg)/(ng/ml)/h | — | — | | | | | |

Sample dosed as 2 (10 mg/kg, equivalent of Base Structure) Parameters for Parent (Base Structur) following dosing of 2

| | Parameter | Unit | Animal 1 | Animal 2 | Animal 3 | Animal 4 | Average | Std. Dev. | Combined |
|---|---|---|---|---|---|---|---|---|---|
| 71 | Lambda_z | 1/h | 0.1912491 | 0.0584922 | 0.0219906 | — | 0.0905773 | 0.0890741 | 0.1 ± 0.1 |
| 72 | t1/2 | h | 3.6243165 | 11.85024 | 31.520108 | — | 15.664888 | 14.333787 | 15.7 ± 14.3 |
| 73 | Tmax | h | 0.08 | 0.08 | 0.08 | 8 | 2.06 | 3.96 | 2.1 ± 4 |
| 74 | Cmax | ng/ml | 151 | 4.73 | 1.36 | 1.65 | 39.685 | 74.225665 | 39.7 ± 74.2 |
| 75 | Tlag | h | 0 | 0 | 0 | 0 | 0 | 0 | 0 ± 0 |
| 76 | Clast_obs/Cmax | | 0.0042848 | 0.0501057 | 0.3117647 | 0.3369697 | 0.1757812 | 0.1728955 | 0.2 ± 0.2 |
| 77 | AUC 0-t | ng/ml*h | 75.7995 | 30.4074 | 12.9897 | 24.48944 | 35.92151 | 27.551283 | 35.9 ± 27.6 |
| 78 | AUC 0-inf_obs | ng/ml*h | 79.182523 | 34.459219 | 32.270635 | — | 48.637459 | 26.475426 | 48.6 ± 26.5 |
| 79 | AUC 0-t/0-inf_obs | | 0.9572756 | 0.882417 | 0.4025238 | — | 0.7474055 | 0.3010124 | 0.7 ± 0.3 |
| 80 | AUMC 0-inf_obs | ng/ml*h^2 | 284.76414 | 414.61785 | 1486.3623 | — | 728.58144 | 659.46145 | 728.6 ± 659.5 |
| 81 | MRT 0-inf_obs | h | 3.5963005 | 12.032131 | 46.059284 | — | 20.562572 | 22.480048 | 20.6 ± 22.5 |
| 82 | Vz/F_obs | (mg/kg)/(ng/ml) | 0.6603457 | 4.9613088 | 14.091419 | — | 6.5710244 | 6.8587039 | 6.6 ± 6.9 |
| 83 | Cl/F_obs | (mg/kg)/(ng/ml)/h | 0.1262905 | 0.2901981 | 0.3098792 | — | 0.2421226 | 0.1007951 | 0.2 ± 0.1 |

Data for Prodrug 2

| | Parameter | Unit | Animal 1 | Animal 2 | Animal 3 | Animal 4 | Average | Std. Dev. | Combined |
|---|---|---|---|---|---|---|---|---|---|
| 87 | Lambda_z | 1/h | 0 | | | | 0 | | 0 |
| 88 | t1/2 | h | 0 | | | | 0 | | 0 |
| 89 | Tmax | h | 0.25 | | | | 0 | | 0 |
| 90 | Cmax | ng/ml | 0.765 | | | | 0 | | 0 |
| 91 | Tlag | h | 0 | | | | 0 | | 0 |
| 92 | Clast_obs/Cmax | | 1 | | | | 0 | | 0 |
| 93 | AUC 0-t | ng/ml*h | 0.089275 | | | | 0 | | 0 |
| 94 | AUC 0-inf_obs | ng/ml*h | — | | | | 0 | | 0 |
| 95 | AUC 0-t/0-inf_obs | | | | | | 0 | | 0 |
| 96 | AUMC 0-inf_obs | ng/ml*h^2 | | | | | 0 | | 0 |
| 97 | MRT 0-inf_obs | h | | | | | 0 | | 0 |
| 98 | Vz/F_obs | (mg/kg)/(ng/ml) | | | | | 0 | | 0 |
| 99 | Cl/F_obs | (mg/kg)/(ng/ml)/h | | | | | 0 | | 0 |

Dosed as A20 (10 mg/kg, equivalent of Base Structure) Parameters for Parent (Base Structure) following dosing of A20

| | Parameter | Unit | Animal 1 | Animal 2 | Animal 3 | Animal 4 | Average | Std. Dev. | Combined |
|---|---|---|---|---|---|---|---|---|---|
| 104 | Lambda_z | 1/h | — | | | 4.021864 | 4.021864 | 0 | 4.0 ± 0 |
| 105 | t1/2 | h | — | | | 0.1723448 | 0.1723448 | 0 | 0.1 ± 0 |
| 106 | Tmax | h | 0.25 | | | 0.25 | 0.25 | 0 | 0.3 ± 0 |
| 107 | Cmax | ng/ml | | | | 2.66 | 1.7125 | 1.3399674 | 1.7 ± 1.3 |
| 108 | Tlag | h | 0 | | | 0 | 0 | 0 | 0 ± 0 |
| 109 | Clast_obs/Cmax | | | | | 0.0582707 | 0.5291353 | 0.6659032 | 0.5 ± 0.7 |
| 110 AUC 0-t | ng/ml*h | | | | 1.5726 | 0.8309375 | 1.0488692 | 0.8 ± 1 |
| 111 AUC 0-inf_obs | ng/ml*h | | | | 1.6111393 | 1.6111393 | | 1.611139 |
| 112 AUC 0-t/0-inf_obs | | | | | 0.9760794 | 0.9760794 | | 0.976079 |

-continued

| Parameter | Unit | Animal 1 | Animal 2 | Animal 3 | Animal 4 | Average | Std. Dev. | Combined |
|---|---|---|---|---|---|---|---|---|
| 113 AUMC 0-inf_obs | ng/ml*h^2 | — | — | — | 0.6699418 | 0.6699418 | | 0.669942 |
| 114 MRT 0-inf_obs | h | — | — | — | 0.4158187 | 0.4158187 | | 0.415819 |
| 115 Vz/F_obs | (mg/kg)(ng/ml) | — | — | — | 1.5432616 | 1.5432616 | | 1.543262 |
| 116 Cl/F_obs | (mg/kg)(ng/ml)/h | — | — | — | 6.2067878 | 6.2067878 | | 6.2067878 |

Data for Prodrug A20

| | | | | | | | | |
|---|---|---|---|---|---|---|---|---|
| 120 Lambda_z | 1/h | 0 | | | | 0 | | 0 |
| 121 t1/2 | h | 0 | | | | 0 | | 0 |
| 122 Tmax | h | 0 | | | | 0 | | 0 |
| 123 Cmax | ng/ml | 0 | | | | 0 | | 0 |
| 124 Tlag | h | 0 | | | | 0 | | 0 |
| 125 Clast_obs/Cmax | | 0 | | | | 0 | | 0 |
| 126 AUC 0-t | ng/ml*h | 0 | | | | 0 | | 0 |
| 127 AUC 0-inf_obs | ng/ml*h | 0 | | | | 0 | | 0 |
| 128 AUC 0-t/0-inf_obs | | 0 | | | | 0 | | 0 |
| 129 AUMC 0-inf_obs | ng/ml*h^2 | 0 | | | | 0 | | 0 |
| 130 MRT 0-inf_obs | h | 0 | | | | 0 | | 0 |
| 131 Vz/F_obs | (mg/kg)(ng/ml) | 0 | | | | 0 | | 0 |
| 132 Cl/F_obs | (mg/kg)(ng/ml)/h | 0 | | | | 0 | | 0 |

Dosed as A21 (10 mg/kg, equivalent of Base Structure) Parent (Base Structure) following dose of A21

| | | | | | | | | |
|---|---|---|---|---|---|---|---|---|
| 137 Lambda_z | 1/h | 0.0080896 | 0.0089246 | — | — | 0.0085071 | 0.0005904 | 0 ± 0 |
| 138 t1/2 | h | 85.683945 | 77.667256 | — | — | 81.6756 | 5.6686552 | 81.7 ± 5.7 |
| 139 Tmax | h | 0.25 | 0.25 | 1 | 2 | 0.875 | 0.8291562 | 0.9 ± 0.8 |
| 140 Cmax | ng/ml | 0.744 | 0.604 | 0.555 | 0.577 | 0.62 | 0.0850608 | 0.6 ± 0.1 |
| 141 Tlag | h | 0 | 0 | 0 | 0 | 0 | 0 | 0 ± 0 |
| 142 Clast_obs/Cmax | | 0.4475806 | 0.5745033 | 0.8630631 | 0.9341421 | 0.7048223 | 0.2315052 | 0.7 ± 0.2 |
| 143 AUC 0-t | ng/ml*h | 7.284615 | 8.222465 | 6.27042 | 8.02234 | 7.44996 | 0.8837489 | 7.4 ± 0.9 |
| 144 AUC 0-inf_obs | ng/ml*h | 48.448677 | 47.103872 | — | — | 47.776275 | 0.9509207 | 47.8 ± 1 |
| 145 AUC 0-t/0-inf_obs | | 0.1503574 | 0.1745603 | — | — | 0.1624588 | 0.017114 | 0.2 ± 0 |
| 146 AUMC 0-inf_obs | ng/ml*h^2 | 6167.4557 | 5387.4053 | — | — | 5777.4305 | 551.5789 | 5777.4 ± 551.6 |
| 147 MRT 0-inf_obs | h | 127.29874 | 114.37288 | — | — | 120.83581 | 9.139968 | 120.8 ± 9.1 |
| 148 Vz/F_obs | (mg/kg)(ng/ml) | 25.514794 | 23.787888 | — | — | 24.651341 | 1.2211068 | 24.7 ± 1.2 |
| 149 Cl/F_obs | (mg/kg)(ng/ml)/h | 0.206404 | 0.2122968 | — | — | 0.2093504 | 0.0041668 | 0.2 ± 0 |

Data for Prodrug A21

| | | | | | | | | |
|---|---|---|---|---|---|---|---|---|
| 153 Lambda_z | 1/h | 0.5256781 | — | — | — | 0.5256781 | | 0.525678 |
| 154 t1/2 | h | 1.3185771 | — | — | — | 1.3185771 | | 1.318577 |
| 155 Tmax | h | 0.25 | 1 | 1 | 1 | 0.8125 | 0.375 | 0.8 ± 0.4 |
| 156 Cmax | ng/ml | 2.18 | 1.89 | 1.01 | 1.38 | 1.615 | 0.5215681 | 1.6 ± 0.5 |
| 157 Tlag | h | 0 | 0 | 0 | 0 | 0 | | 0 ± 0 |
| 158 Clast_obs/Cmax | | 0.2027523 | 0.6296296 | 0.6049505 | 0.5862319 | 0.5058911 | 0.2028725 | 0.5 ± 0.2 |
| 159 AUC 0-t | ng/ml*h | 5.61855 | 2.381305 | 1.497735 | 1.885 | 2.8456475 | 1.8836413 | 2.8 ± 1.9 |
| 160 AUC 0-inf_obs | ng/ml*h | 64.593687 | — | — | — | 64.593687 | | 6.459369 |
| 161 AUC 0-t/0-inf_obs | | 0.8698296 | — | — | — | 0.8698296 | | 0.86983 |
| 162 AUMC 0-inf_obs | ng/ml*h^2 | 13.688243 | — | — | — | 13.688243 | | 13.68824 |
| 163 MRT 0-inf_obs | h | 2.1191302 | — | — | — | 2.1191302 | | 2.11913 |
| 164 Vz/F_obs | (mg/kg)(ng/ml) | 2.9450319 | — | — | — | 2.9450319 | | 2.945032 |
| 165 Cl/F_obs | (mg/kg)(ng/ml)/h | 1.5481389 | — | — | — | 1.5481389 | | 1.5481389 |

-continued

| Parameter | Unit | Animal 1 | Animal 2 | Animal 3 | Animal 4 | Average | Std. Dev. | Combined |
|---|---|---|---|---|---|---|---|---|
| | | | | | | | | |
| | | Dosed as A22 (10 mg/kg, equivalent of Base Structure) Parameters for Parent (Base Structure) following dosing of A22 | | | | | | |
| 170 Lambda_z | 1/h | — | 0.0117847 | — | — | 0.0117847 | | 0.011785 |
| 171 t1/2 | h | — | 58.817694 | — | — | 58.817694 | | 58.81769 |
| 172 Tmax | h | 24 | 4 | 24 | 8 | 15 | 10.519823 | 15 ± 10.5 |
| 173 Cmax | ng/ml | 1.51 | 1.32 | 1.35 | 1.55 | 1.4325 | 0.1144188 | 1.4 ± 0.1 |
| 174 Tlag | h | 0 | 0 | 0 | 0 | 0 | 0 | 0 ± 0 |
| 175 Clast_obs/Cmax | | 1 | 0.6477273 | — | 0.4251613 | 0.7682221 | 0.2826374 | 0.8 ± 0.3 |
| 176 AUC 0-t | ng/ml*h | 28.915155 | 18.755375 | 26.459875 | 26.3888 | 25.129801 | 4.408945 | 25.1 ± 4.4 |
| 177 AUC 0-inf_obs | ng/ml*h | — | 91.307251 | — | — | 91.307251 | | 91.30725 |
| 178 AUC 0-t/0-inf_obs | | — | 0.2054095 | — | — | 0.2054095 | | 0.205409 |
| 179 AUMC 0-inf_obs | ng/ml*h^2 | — | 8134.3242 | — | — | 8134.3242 | | 8134.324 |
| 180 MRT 0-inf_obs | h | — | 89.087384 | — | — | 89.087384 | | 89.08738 |
| 181 Vz/F_obs | (mg/kg)/(ng/ml) | — | 9.2934564 | — | — | 9.2934564 | | 9.293456 |
| 182 Cl/F_obs | (mg/kg)/(ng/ml)/h | — | 0.1095203 | — | — | 0.1095203 | | 0.1095203 |
| | | | | Data for Prodrug A22 | | | | |
| 186 Lambda_z | 1/h | 0 | | | | 0 | | 0 |
| 187 t1/2 | h | 0 | | | | 0 | | 0 |
| 188 Tmax | h | 0 | | | | 0 | | 0 |
| 189 Cmax | ng/ml | 0 | | | | 0 | | 0 |
| 190 Tlag | h | 0 | | | | 0 | | 0 |
| 191 Clast_obs/Cmax | | 0 | | | | 0 | | 0 |
| 192 AUC 0-t | ng/ml*h | 0 | | | | 0 | | 0 |
| 193 AUC 0-inf_obs | ng/ml*h | 0 | | | | 0 | | 0 |
| 194 AUC 0-t/0-inf_obs | | 0 | | | | 0 | | 0 |
| 195 AUMC 0-inf_obs | ng/ml*h^2 | 0 | | | | 0 | | 0 |
| 196 MRT 0-inf_obs | h | 0 | | | | 0 | | 0 |
| 197 Vz/F_obs | (mg/kg)/(ng/ml) | 0 | | | | 0 | | 0 |
| 198 Cl/F_obs | (mg/kg)/(ng/ml)/h | 0 | | | | 0 | | 0 |
| | | Dosed as A23 (10 mg/kg, equivalent of Vase Structure) Parameters for Parent (Base Structure) following dosing of A23 | | | | | | |
| 203 Lambda_z | 1/h | 0.0435952 | 0.0738764 | 0.0440852 | 0.014645 | 0.0440505 | 0.0241832 | 0 ± 17.1 |
| 204 t1/2 | h | 15.899634 | 9.3825196 | 15.722913 | 47.329796 | 22.083715 | 17.101536 | 22.1 ± 17.1 |
| 205 Tmax | h | 0.08 | 0.5 | 0.08 | 0.25 | 0.2275 | 0.1985573 | 0.2 ± 0.2 |
| 206 Cmax | ng/ml | 2.51 | 3.48 | 14.6 | 1.28 | 5.4675 | 6.1545288 | 5.5 ± 6.2 |
| 207 Tlag | h | 0 | 0 | 0 | 0 | 0 | 0 | 0 ± 0 |
| 208 Clast_obs/Cmax | | 0.0454183 | 0.0321839 | 0.0165753 | 0.2234375 | 0.0794038 | 0.0967434 | 0.1 ± 0.1 |
| 209 AUC 0-t | ng/ml*h | 3.56898 | 4.61648 | 6.95044 | 5.29615 | 5.1080125 | 1.4189386 | 5.1 ± 1.4 |
| 210 AUC 0-inf_obs | ng/ml*h | 6.1839488 | 6.1325248 | 12.439815 | 24.824934 | 12.395306 | 8.7996405 | 12.4 ± 8.8 |
| 211 AUC 0-t/0-inf_obs | | 0.5771361 | 0.7527862 | 0.5587253 | 0.2133399 | 0.5254969 | 0.2257381 | 0.5 ± 0.2 |
| 212 AUMC 0-inf_obs | ng/ml*h^2 | 156.19016 | 90.340465 | 316.30901 | 1873.3254 | 609.04125 | 848.18063 | 609 ± 848.2 |
| 213 MRT 0-inf_obs | h | 25.257349 | 14.731366 | 25.47147 | 75.461445 | 35.219327 | 27.290489 | 35.2 ± 27.3 |
| 214 Vz/F_obs | (mg/kg)/(ng/ml) | 37.093326 | 22.072662 | 18.23449 | 27.505596 | 26.226518 | 8.1823099 | 26.2 ± 8.2 |
| 215 Cl/F_obs | (mg/kg)/(ng/ml)/h | 1.6170897 | 1.6306497 | 0.08038705 | 0.4028208 | 1.1136077 | 0.6115504 | 1.1 ± 0.6 |
| | | | | Data for Prodrug A23 | | | | |
| 219 Lambda_z | 1/h | 0 | | | | 0 | | 0 |
| 220 t1/2 | h | 0 | | | | 0 | | 0 |
| 221 Tmax | h | 0 | | | | 0 | | 0 |
| 222 Cmax | ng/ml | 0 | | | | 0 | | 0 |

-continued

| | Parameter | Unit | Animal 1 | Animal 2 | Animal 3 | Animal 4 | Average | Std. Dev. | Combined |
|---|---|---|---|---|---|---|---|---|---|
| 223 | Tlag | h | 0 | | | | 0 | | 0 |
| 224 | Clast_obs/Cmax | | 0 | | | | 0 | | 0 |
| 225 | AUC 0-t | ng/ml*h | 0 | | | | 0 | | 0 |
| 226 | AUC 0-inf_obs | ng/ml*h | 0 | | | | 0 | | 0 |
| 227 | AUC 0-t/0-inf_obs | | 0 | | | | 0 | | 0 |
| 228 | AUMC 0-inf_obs | ng/ml*h^2 | 0 | | | | 0 | | 0 |
| 229 | MRT 0-inf_obs | h | 0 | | | | 0 | | 0 |
| 230 | Vz/F_obs | (mg/kg)(ng/ml) | | | | | | | |
| 231 | Cl/F_obs | (mg/kg)(ng/ml)/h | | | | | | | |
| | | | Dosed as A24 (10 mg/kg, equivalent of Base Structure) Parameters for Parent (Base Structure) following dosing of A24 | | | | | | |
| 236 | Lambda_z | 1/h | 0.2216601 | 0.0152996 | 0.6866692 | 0.0645992 | 0.3243095 | 0.3234895 | 0.3 ± 0.3 |
| 237 | t1/2 | h | 3.1270727 | 45.304992 | 1.009434 | 10.729971 | 4.9554926 | 5.1117072 | 5 ± 5.1 |
| 238 | Tmax | h | 0.5 | 1 | 0.217 | 0.08 | 0.415 | 0.4373786 | 0.4 ± 0.4 |
| 239 | Cmax | ng/ml | 0.351 | 0.287 | 0.217 | 0.218 | 0.26825 | 0.0641632 | 0.3 ± 0.1 |
| 240 | Tlag | h | 0 | 0 | 0 | 0 | 0 | 0 | 0 ± 0 |
| 241 | Clast_obs/Cmax | | 0.3019943 | 0.158885 | 0.4046083 | 0.4284404 | 0.323482 | 0.1226806 | 0.3 ± 0.1 |
| 242 | AUC 0-t | ng/ml*h | 0.530985 | 0.35458 | 0.12241 | 0.616765 | 0.406185 | 0.2184112 | 0.4 ± 0.2 |
| 243 | AUC 0-inf_obs | ng/ml*h | 1.0091947 | | 0.2502736 | 2.0626041 | 1.1073575 | 0.9101442 | 1.1 ± 0.9 |
| 244 | AUC 0-t/0-inf_obs | | 0.5261472 | | 0.4891047 | 0.2990225 | 0.4380915 | 0.1218531 | 0.4 ± 0.1 |
| 245 | AUMC 0-inf_obs | ng/ml*h^2 | 4.9662575 | | 0.3669321 | 36.618365 | 13.983852 | 19.736498 | 14 ± 19.7 |
| 246 | MRT 0-inf_obs | h | 4.9210102 | | 1.4661237 | 17.753463 | 8.0468655 | 8.5818169 | 8 ± 8.6 |
| 247 | Vz/F_obs | (mg/kg)(ng/ml) | 44.703091 | | 58.188531 | 75.051126 | 59.31425 | 15.205303 | 59.3 ± 15.2 |
| 248 | Cl/F_obs | (mg/kg)(ng/ml)/h | 9.9088907 | | 39.95627 | 4.8482401 | 18.2378 | 18.978184 | 18.2 ± 19 |
| | | | | | Data for Prodrug A24 | | | | |
| 252 | Lambda_z | 1/h | — | — | — | — | | | |
| 253 | t1/2 | h | — | — | — | — | | | |
| 254 | Tmax | h | 1 | 1 | 1 | 0.5 | 0.875 | 0.25 | 0.9 ± 0.3 |
| 255 | Cmax | ng/ml | 0.503 | 0.678 | 0.513 | 0.503 | 0.54925 | 0.0859627 | 0.5 ± 0.1 |
| 256 | Tlag | h | 0 | 0 | 0 | 0 | 0 | 0 | 0 ± 0 |
| 257 | Clast_obs/Cmax | | 1 | 1 | 1 | 1 | 1 | 0 | 1 ± 0 |
| 258 | AUC 0-t | ng/ml*h | 0.188625 | 0.25425 | 0.192375 | 0.062875 | 0.1745313 | 0.0802895 | 0.2 ± 0.1 |
| 259 | AUC 0-inf_obs | ng/ml*h | — | — | — | — | | | |
| 260 | AUC 0-t/0-inf_obs | | — | — | — | — | | | |
| 261 | AUMC 0-inf_obs | ng/ml*h^2 | — | — | — | — | | | |
| 262 | MRT 0-inf_obs | h | — | — | — | — | | | |
| 263 | Vz/F_obs | (mg/kg)(ng/ml) | — | — | — | — | | | |
| 264 | Cl/F_obs | (mg/kg)(ng/ml)/h | — | — | — | — | | | |
| | | | Dose as A25 (10 mg/kg, equivalent of Base Structure) Parameters for Parent (Base Structure) following dosing of A25 | | | | | | |
| 269 | Lambda_z | 1/h | 0.1243062 | 0.0152996 | 0.0061827 | 0.0980479 | 0.0609591 | 0.0590866 | 0.1 ± 0.1 |
| 270 | t1/2 | h | 5.5761279 | 45.304992 | 112.11041 | 7.0694775 | 42.515252 | 49.907149 | 42.5 ± 49.9 |
| 271 | Tmax | h | 0.25 | 0.08 | 0.5 | 0.25 | 0.27 | 0.1730125 | 0.3 ± 0.2 |
| 272 | Cmax | ng/ml | 8.15 | 0.862 | 0.699 | 2.67 | 3.09525 | 3.4861992 | 3.1 ± 3.5 |
| 273 | Tlag | h | 0 | 0 | 0 | 0 | 0 | 0 | 0 ± 0 |
| 274 | Clast_obs/Cmax | | 0.0342331 | 0.3422274 | 0.5035765 | 0.0700375 | 0.2375186 | 0.2244443 | 0.2 ± 0.2 |
| 275 | AUC 0-t | ng/ml*h | 16.115725 | 7.403555 | 11.877475 | 8.2102 | 10.91212 | 4.0022368 | 10.9 ± 4 |
| 276 | AUC 0-inf_obs | ng/ml*h | 18.401708 | 26.685135 | 68.810354 | 10.117432 | 31.003657 | 26.096229 | 31 ± 26.1 |
| 277 | AUC 0-t/0-inf_obs | | 0.8780299 | 0.2774412 | 0.1726117 | 0.8114905 | 0.5348933 | 0.3613762 | 0.5 ± 0.4 |
| 278 | AUMC 0-inf_obs | ng/ml*h^2 | 158.76057 | 1811.7945 | 10702.647 | 123.73178 | 3199.2334 | 5063.9044 | 3199.2 ± 5063.9 |

-continued

| Parameter | Unit | Animal 1 | Animal 2 | Animal 3 | Animal 4 | Average | Std. Dev. | Combined |
|---|---|---|---|---|---|---|---|---|
| 279 MRT 0-inf_obs | h | 8.6274912 | 67.895273 | 155.53832 | 12.229564 | 61.072662 | 68.572231 | 61.1 ± 68.6 |
| 280 Vz/F_obs | (mg/kg)(ng/ml) | 4.3716877 | 24.49352 | 23.505348 | 10.080072 | 15.612819 | 9.9687179 | 15.6 ± 10 |
| 281 Cl/F_obs | (mg/kg)(ng/ml)/h | 0.5434278 | 0.3747405 | 0.145327 | 0.9983931 | 0.5129721 | 0.3564752 | 0.5 ± 0.4 |
|  |  |  |  | Data for Prodrug A25 |  |  |  |  |
| 295 Lambda_z | 1/h | 0.001038 |  |  |  | 0.001038 |  | 0.001038 |
| 286 t1/2 | h | 667.7753 |  |  |  | 667.7753 |  | 667.7753 |
| 287 Tmax | h | 1 | 24 | 4 | 8 | 9.25 | 10.242884 | 9.3 ± 10.2 |
| 288 Cmax | ng/ml | 4.23 | 4.21 | 4 | 4.28 | 4.18 | 0.1235584 | 4.2 ± 0.1 |
| 289 Tlag | h | 0 | 0 | 0 | 0 | 0 | 0 | 0 ± 0 |
| 290 Clast_obs/Cmax |  | 0.8888889 | 1 | 0.9625 | 0.885514 | 0.9342257 | 0.0564327 | 0.9 ± 0.1 |
| 291 AUC 0-t | ng/ml*h | 87.1052 | 93.73835 | 88.82275 | 95.084 | 91.187575 | 3.8273909 | 91.2 ± 3.8 |
| 292 AUC 0-inf_obs | ng/ml*h | 3709.4746 |  |  |  | 3709.4746 |  | 3709.475 |
| 293 AUC 0-t/0-inf_obs |  | 0.0234818 |  |  |  | 0.0234818 |  | 0.023482 |
| 294 AUMC 0-inf_obs | ng/ml*h^2 | 3577773.1 |  |  |  | 3577773.1 |  | 3577773 |
| 295 MRT 0-inf_obs | h | 964.49592 |  |  |  | 964.49592 |  | 964.4959 |
| 296 Vz/F_obs | (mg/kg)(ng/ml) | 2.5971228 |  |  |  | 2.5971228 |  | 2.597123 |
| 297 Cl/F_obs | (mg/kg)(ng/ml)/h | 0.0026958 |  |  |  | 0.0026958 |  | 0.0026958 |
|  |  | Dosed as A26 (10 mg/kg, equivalent of Base Structure) Parameters for Parent (Base Structure) following dosing of A26 |  |  |  |  |  |  |
| 302 Lambda_z | 1/h | 0.074747 | 0.0804088 |  |  | 0.0775779 | 0.0040035 | 0.1 ± 0 |
| 303 t1/2 | h | 9.2732385 | 8.6202849 |  |  | 8.9467617 | 0.4617079 | 8.9 ± 0.5 |
| 304 Tmax | h | 0.25 | 0.08 | 4 | 0.08 | 1.1025 | 1.9333283 | 1.1 ± 1.9 |
| 305 Cmax | ng/ml | 15.5 | 8.31 | 1.5 | 1.84 | 6.7875 | 6.5995221 | 6.8 ± 6.6 |
| 306 Tlag | h | 0 | 0 | 0 | 0 | 0 | 0 | 0 ± 0 |
| 307 Clast_obs/Cmax |  | 0.0658065 | 0.07858 | 0.64 | 0.3625 | 0.2867216 | 0.2724423 | 0.3 ± 0.3 |
| 308 AUC 0-t | ng/ml*h | 22.797 | 11.33965 | 14.321275 | 7.97054 | 14.107116 | 6.347608 | 14.1 ± 6.3 |
| 309 AUC 0-inf_obs | ng/ml*h | 36.443024 | 19.460647 |  |  | 27.951836 | 12.008354 | 28 ± 12 |
| 310 AUC 0-t/0-inf_obs |  | 0.6255518 | 0.5826965 |  |  | 0.6041241 | 0.0303033 | 0.6 ± 0 |
| 311 AUMC 0-inf_obs | ng/ml*h^2 | 724.50431 | 430.36668 |  |  | 577.43549 | 207.98671 | 577.4 ± 208 |
| 312 MRT 0-inf_obs | h | 19.880466 | 22.114716 |  |  | 20.997591 | 1.5798534 | 21 ± 16 |
| 313 Vz/F_obs | (mg/kg)(ng/ml) | 3.3710606 | 6.3905596 |  |  | 5.3081001 | 1.9229761 | 5 ± 1.9 |
| 314 Cl/F_obs | (mg/kg)(ng/ml)/h | 0.2744009 | 0.5138575 |  |  | 0.3941292 | 0.1693214 | 0.4 ± 0.2 |
|  |  |  |  | Data for Prodrug A26 |  |  |  |  |
| 318 Lambda_z | 1/h | 0 | 0 |  |  | 0 |  | 0 |
| 319 t1/2 | h | 0 | 0 |  |  | 0 |  | 0 |
| 320 Tmax | h | 0 | 0 |  |  | 0 |  | 0 |
| 321 Cmax | ng/ml | 0 | 0 |  |  | 0 |  | 0 |
| 322 Tlag | h | 0 | 0 |  |  | 0 |  | 0 |
| 323 Clast_obs/Cmax |  | 0 | 0 |  |  | 0 |  | 0 |
| 324 AUC 0-t | ng/ml*h | 0 | 0 |  |  | 0 |  | 0 |
| 325 AUC 0-inf_obs | ng/ml*h | 0 | 0 |  |  | 0 |  | 0 |
| 326 AUC 0-t/0-inf_obs |  | 0 | 0 |  |  | 0 |  | 0 |
| 327 AUMC 0-inf_obs | ng/ml*h^2 | 0 | 0 |  |  | 0 |  | 0 |
| 328 MRT 0-inf_obs | h | 0 | 0 |  |  | 0 |  | 0 |
| 329 Vz/F_obs | (mg/kg)(ng/ml) | 0 | 0 |  |  | 0 |  | 0 |
| 330 Cl/F_obs | (mg/kg)(ng/ml)/h | 0 | 0 |  |  | 0 |  | 0 |

-continued

| Parameter | Unit | Animal 1 | Animal 2 | Animal 3 | Animal 4 | Average | Std. Dev. | Combined |
|---|---|---|---|---|---|---|---|---|
| | | Dosed as A27 (10 mg/kg, equivalent of Base Structure) Parameters for Parent (Base Structure) following dosing of A27 | | | | | | |
| 335 Lambda_z | 1/h | — | — | 0.0517028 | — | 0.0517028 | | 0.051703 |
| 336 t1/2 | h | — | — | 13.406364 | — | 13.406364 | | 13.40636 |
| 337 Tmax | h | 24 | 24 | 0.5 | 24 | 18.125 | 11.75 | 18.1 ± 11.8 |
| 338 Cmax | ng/ml | 0.72 | 2.13 | 1.55 | 6.68 | 2.77 | 2.6701186 | 2.8 ± 2.7 |
| 339 Tlag | h | 0 | 0 | 0 | 0 | 0 | 0 | 0 ± 0 |
| 340 Clast_obs/Cmax | | 1 | 1 | 0.143871 | 1 | 0.7859677 | 0.4280645 | 0.8 ± 0.4 |
| 341 AUC 0-t | ng/ml*h | 8.586975 | 24.54622 | 4.686395 | 80.391315 | 29.552726 | 34.964384 | 29.6 ± 35 |
| 342 AUC 0-inf_obs | ng/ml*h | — | — | 8.9995036 | — | 8.9995036 | | 8.999504 |
| 343 AUC 0-t/0-inf_obs | | — | — | 0.5207393 | — | 0.5207393 | | 0.520739 |
| 344 AUMC 0-inf_obs | ng/ml*h^2 | — | — | 238.35106 | — | 238.35106 | | 238.3511 |
| 345 MRT 0-inf_obs | h | — | — | 26.484912 | — | 26.484912 | | 26.48491 |
| 346 Vz/F_obs | (mg/kg)(ng/ml) | — | — | 21.491512 | — | 21.491512 | | 21.49151 |
| 347 Cl/F_obs | (mg/kg)(ng/ml)/h | — | — | 1.1111724 | — | 1.1111724 | | 1.111724 |
| | | Data for Prodrug A27 | | | | | | |
| 351 Lambda_z | 1/h | 0 | | | | 0 | | 0 |
| 352 t1/2 | h | 0 | | | | 0 | | 0 |
| 353 Tmax | h | 0 | | | | 0 | | 0 |
| 354 Cmax | ng/ml | 0 | | | | 0 | | 0 |
| 355 Tlag | h | 0 | | | | 0 | | 0 |
| 356 Clast_obs/Cmax | | 0 | | | | 0 | | 0 |
| 357 AUC 0-t | ng/ml*h | 0 | | | | 0 | | 0 |
| 358 AUC 0-inf_obs | ng/ml*h | 0 | | | | 0 | | 0 |
| 359 AUC 0-t/0-inf_obs | | 0 | | | | 0 | | 0 |
| 360 AUMC 0-inf_obs | ng/ml*h^2 | 0 | | | | 0 | | 0 |
| 361 MRT 0-inf_obs | h | 0 | | | | 0 | | 0 |
| 362 Vz/F_obs | (mg/kg)(ng/ml) | 0 | | | | 0 | | 0 |
| 363 Cl/F_obs | (mg/kg)(ng/ml)/h | 0 | | | | 0 | | 0 |

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

We claim:
1. A compound of formula (II):

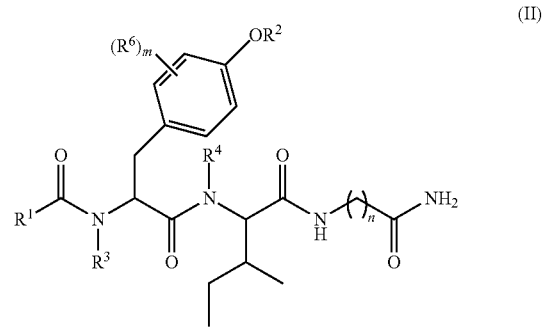

wherein:
n is 3, 4, 5, 6, 7, 8, or 9;
m is 0, 1, 2, 3, or 4;
$R^1$ is selected from $C_1$-$C_{12}$ alkyl, $C_1$-$C_{12}$ substituted alkyl, $C_2$-$C_{12}$ alkenyl, $C_2$-$C_{12}$ substituted alkenyl, $C_2$-$C_{12}$ alkynyl, and $C_2$-$C_{12}$ substituted alkynyl;
$R^2$ is selected from hydrogen, -$\xi$-$PO(OY)_2$, -$\xi$-$PO(OH)_2$, —C(=O)—Y and —CO—U;
each Y is independently —Z—$(CH_2)_q$—W—$R^b$,
or —C(=O)—Y forms an amide bond through a nitrogen atom on Y, and Y is selected from glycine, sarcosine, N,N-dimethylglycine, alanine, valine, leucine, isoleucine, lysine, ornithine, arginine, serine, and threonine;
q is 0-4;
each Z and W is independently selected from $CH_2$, O, S, $NR^c$ and $R^b$,
or Z and W are taken together to form a $C_3$-$C_8$ heterocycloalkyl or $C_4$-$C_{10}$ heteroaryl or bicyclic ring system in which one of the rings is a $C_4$-$C_{10}$ heteroaryl;
each $R^c$ is independently selected from hydrogen, $C_1$-$C_4$ alkyl, and $C_3$-$C_6$ cycloalkyl;
each $R^b$ is independently selected from hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl;
U is selected from pyridine, 1,4-dihydropyridine, N-alkyl-1,4-dihydropyridine, and C-imidazole, or U is aryl, heteroaryl or heterocycloalkyl;
$R^3$ and $R^4$ are independently selected from hydrogen, $C_1$-$C_{12}$ alkyl, $C_1$-$C_{12}$ substituted alkyl, $C_2$-$C_{12}$ alkenyl, $C_2$-$C_{12}$ substituted alkenyl, $C_2$-$C_{12}$ alkynyl, and $C_2$-$C_{12}$ substituted alkynyl,
or $R^3$ and $R^4$ are taken together to form a fused bicyclic ring system or a spirocyclic ring system; and each $R^6$ is independently selected from hydrogen, deuterium, $CH_3$, F, $^{19}F$, and $^{18}F$;

wherein each heterocyclic and heteroaryl ring contains up to four heteroatoms selected from O, N, and S;

with the proviso that when both Z and W are heteroatoms, the value of q cannot be 1;

and with the proviso that when $R^2$ is hydrogen, at least one of the $R^3$ or $R^4$ groups is not hydrogen;

or a tautomer or a pharmaceutically acceptable salt thereof, or a pharmaceutically acceptable salt of the tautomer.

2. The compound of claim 1, wherein:

m is 0;

$R^1$ is a $C_1$-$C_{12}$ alkyl; and $R^3$ and $R^4$ are taken together to form a spirocyclic ring system, or a tautomer or a pharmaceutically acceptable salt thereof, or a pharmaceutically acceptable salt of the tautomer.

3. The compound of claim 1, wherein:

m is 1 or 2;

$R^1$ is a $C_1$-$C_{12}$ alkyl;

$R^3$ and $R^4$ are taken together to form a spirocyclic ring system; and $R^6$ is selected from hydrogen, deuterium, F, $^{19}F$, and $^{18}F$, or a tautomer or a pharmaceutically acceptable salt thereof, or a pharmaceutically acceptable salt of the tautomer.

4. A pharmaceutical composition comprising the compound of claim 1, or a tautomer or a pharmaceutically acceptable salt thereof, or a pharmaceutically acceptable salt of the tautomer, and a pharmaceutically acceptable carrier or excipient.

5. The compound of claim 1, wherein:

$R^1$ is selected from $C_1$-$C_{12}$ alkyl optionally substituted with 1-5 substituents independently selected from alkoxy, cyano, halo, and hydroxy; $C_2$-$C_{12}$ alkenyl optionally substituted with 1-5 substituents independently selected from alkoxy, cyano, halo, and hydroxy; and $C_2$-$C_{12}$ alkynyl optionally substituted with 1-5 substituents independently selected from alkoxy, cyano, halo, and hydroxy;

each $R^b$ is independently selected from hydrogen; $C_1$-$C_{12}$ alkyl optionally substituted with 1-5 substituents independently selected from alkoxy, cyano, halo, and hydroxy; $C_3$-$C_8$ cycloalkyl optionally substituted with 1-5 substituents selected from $C_1$-$C_6$ alkyl, alkoxy, cyano, halo, hydroxy, and oxo; and $C_3$-$C_8$ heterocycloalkyl optionally substituted with 1-5 substituents selected from $C_1$-$C_6$ alkyl, alkoxy, cyano, halo, hydroxy, and oxo; and $R^3$ and $R^4$ are independently selected from hydrogen; $C_1$-$C_{12}$ alkyl optionally substituted with 1-5 substituents independently selected from alkoxy, cyano, halo, and hydroxy; $C_2$-$C_{12}$ alkenyl optionally substituted with 1-5 substituents independently selected from alkoxy, cyano, halo, and hydroxy; and $C_2$-$C_{12}$ alkynyl optionally substituted with 1-5 substituents independently selected from alkoxy, cyano, halo, and hydroxy;

or a tautomer or a pharmaceutically acceptable salt thereof, or a pharmaceutically acceptable salt of the tautomer.

6. The compound of claim 1, which is of formula (III):

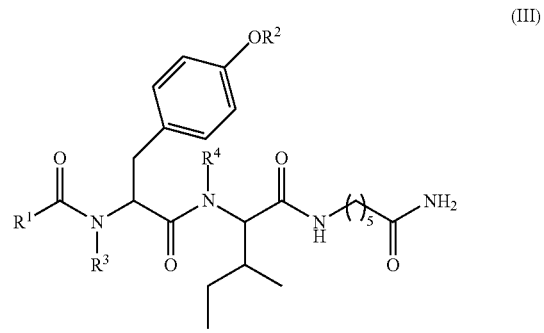

(III)

wherein:

$R^1$ is a $C_1$-$C_{12}$ alkyl or $C_1$-$C_{12}$ substituted alkyl;

$R^2$ is selected from hydrogen, $-PO(OY)_2$, $-PO(OH)_2$, and $-C(=O)-Y$;

each Y is independently $-Z-(CH_2)_q-W-R^b$;

q is 0-4;

Z and W are independently selected from $CH_2$, O, S, $NR^c$ and $R^b$, or Z and W are taken together to form a $C_3$-$C_8$ heterocycloalkyl or $C_4$-$C_{10}$ heteroaryl or bicyclic ring system in which one of the rings is a $C_4$-$C_{10}$ heteroaryl;

each $R^c$ is independently selected from hydrogen, $C_1$-$C_4$ alkyl, and $C_3$-$C_6$ cycloalkyl;

each $R^b$ is independently selected from hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl; and $R^3$ and $R^4$ are independently selected from hydrogen, $C_1$-$C_{12}$ alkyl, $C_1$-$C_{12}$ substituted alkyl, $C_2$-$C_{12}$ alkenyl, $C_2$-$C_{12}$ substituted alkenyl, $C_2$-$C_{12}$ alkynyl, and $C_2$-$C_{12}$ substituted alkynyl, or $R^3$ and $R^4$ are taken together to form a fused bicyclic ring system or a spirocyclic ring system, wherein the fused ring is $C_3$-$C_8$ heterocycloalkyl, $C_6$-$C_{10}$ aryl, or $C_4$-$C_{10}$ heteroaryl;

wherein each heterocyclic and heteroaryl ring contains up to four heteroatoms selected from O, N, and S;

with the proviso that when both Z and W are heteroatoms, the value of q cannot be 1;

and with the proviso that when $R^2$ is hydrogen, at least one of the $R^3$ or $R^4$ groups is not hydrogen;

or a tautomer or a pharmaceutically acceptable salt thereof, or a pharmaceutically acceptable salt of the tautomer.

7. The compound of claim 6, wherein:

$R^1$ is a $C_1$-$C_{12}$ alkyl;

$R^2$ is $-C(=O)-Y$; and $R^3$ and $R^4$ are each hydrogen, or a tautomer or a pharmaceutically acceptable salt thereof, or a pharmaceutically acceptable salt of the tautomer.

8. The compound of claim 6, wherein:

$R^1$ is a $C_1$-$C_{12}$ alkyl;

$R^2$ is $-C(=O)-CH(NH_2)^iPr$; and $R^3$ and $R^4$ are each hydrogen, or a tautomer or a pharmaceutically acceptable salt thereof, or a pharmaceutically acceptable salt of the tautomer.

9. The compound of claim 6, wherein:
$R^1$ is a $C_1$-$C_{12}$ alkyl;
$R^2$ is —C(=O)—CH(NH$_2$)$^i$Pr; and
$R^3$ and $R^4$ are each hydrogen;
m is 1 or 2; and
$R^6$ is F,
or a tautomer or a pharmaceutically acceptable salt thereof, or a pharmaceutically acceptable salt of the tautomer.

10. The compound of claim 6, wherein:
$R^1$ is a $C_1$-$C_{12}$ alkyl;
$R^2$ is -$\xi$- PO(OH)$_2$; and
$R^3$ and $R^4$ are each hydrogen,
or a tautomer or a pharmaceutically acceptable salt thereof, or a pharmaceutically acceptable salt of the tautomer.

11. A compound selected from:

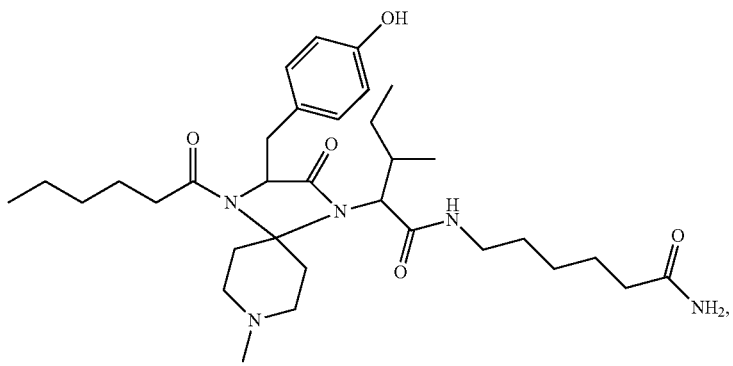

1

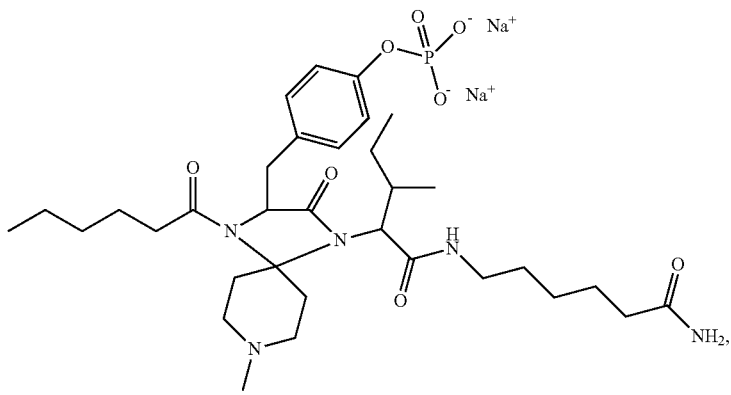

2

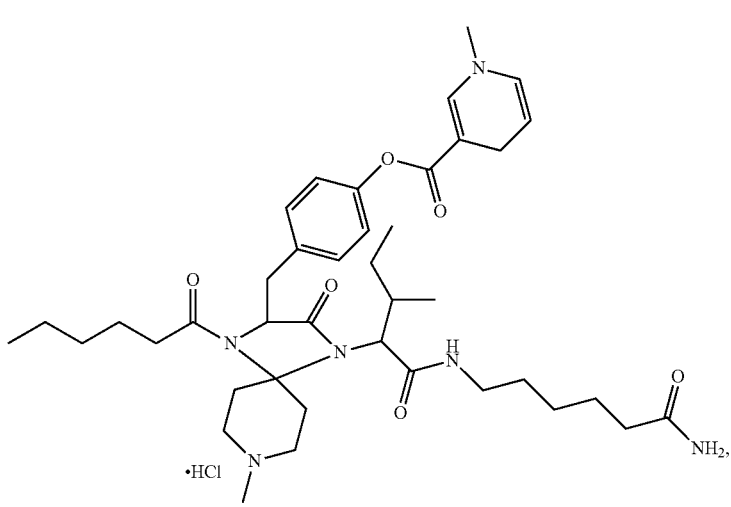

3

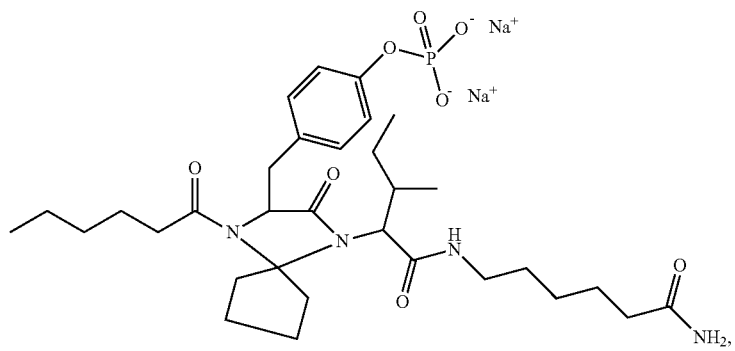
4
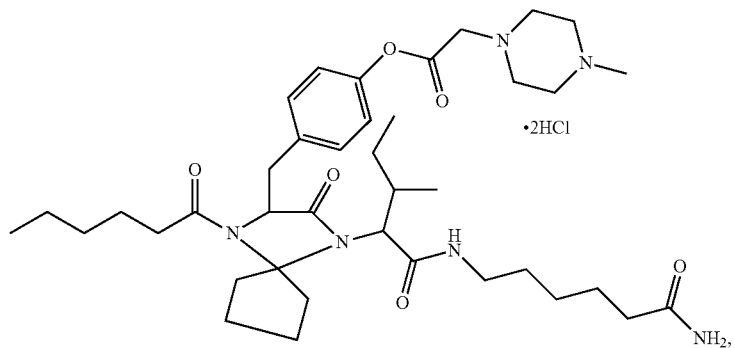
5
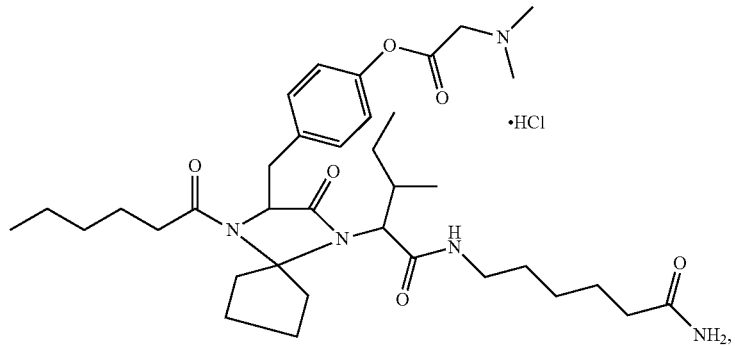
6
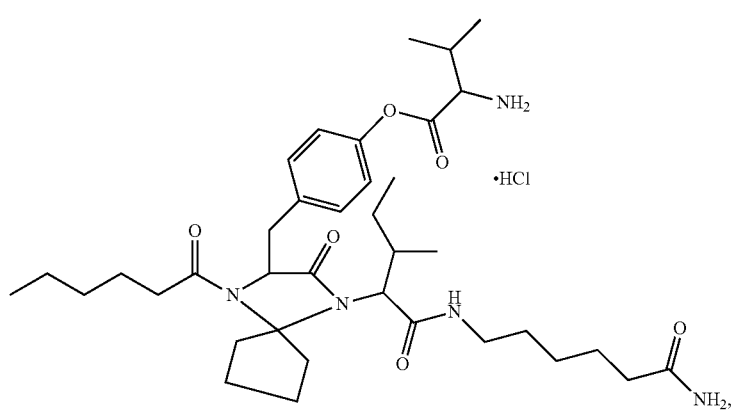
7

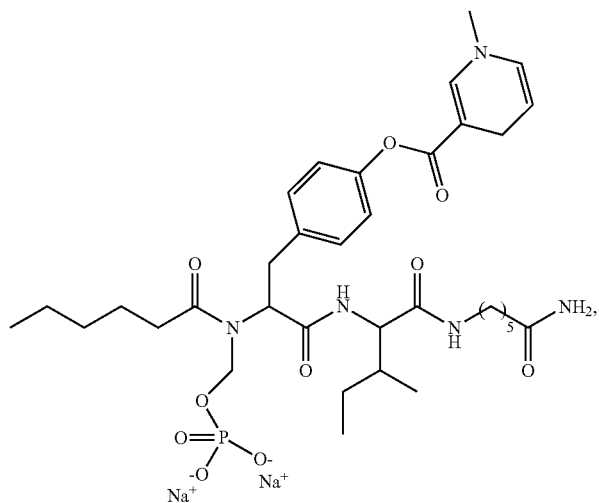
9
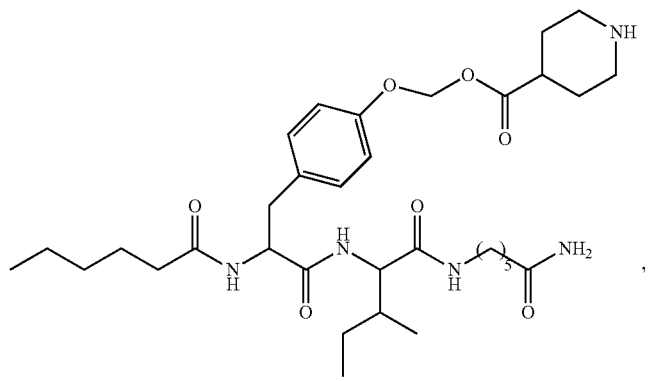
A17a
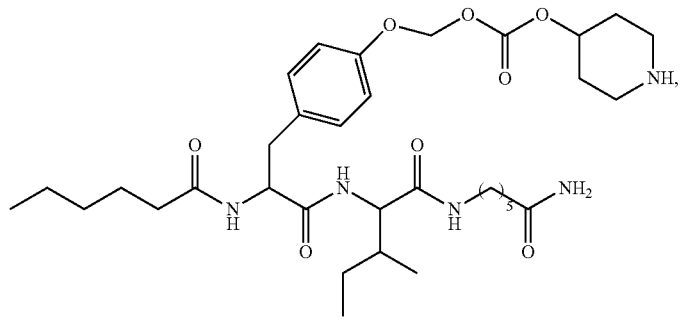
A17b
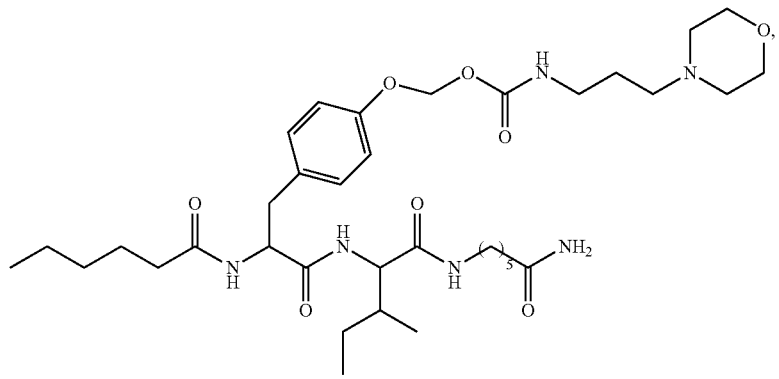
A17c

-continued
A17e
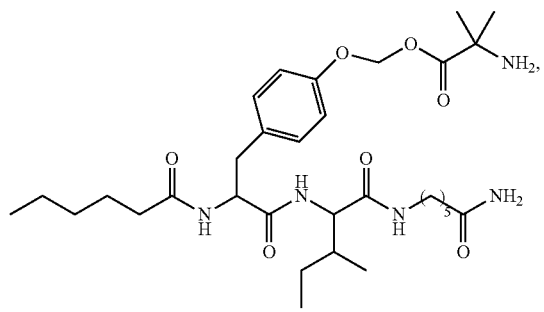
A17f
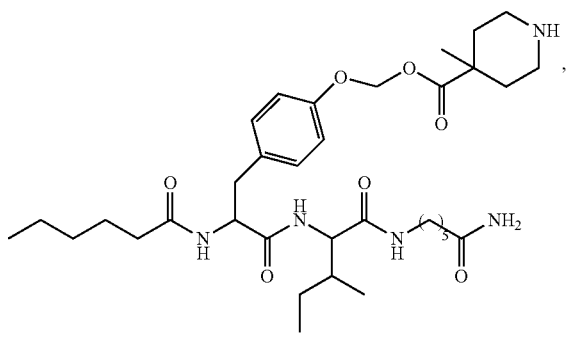
A17g
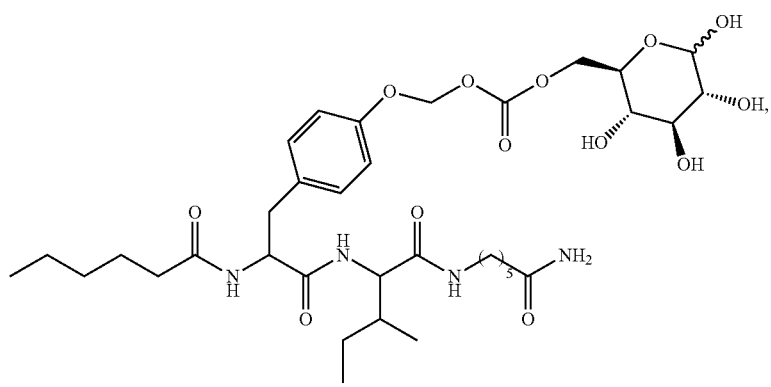
A17h
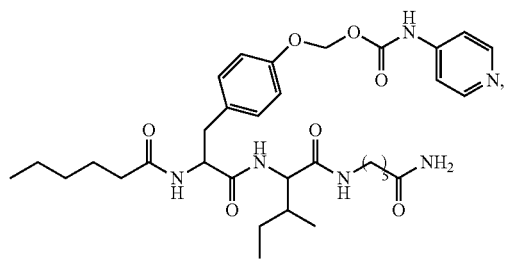
A17i
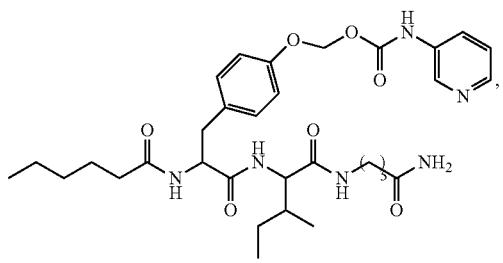
A17j
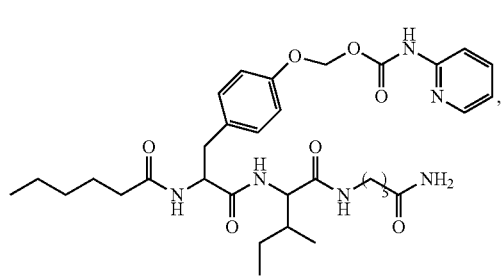
A17k
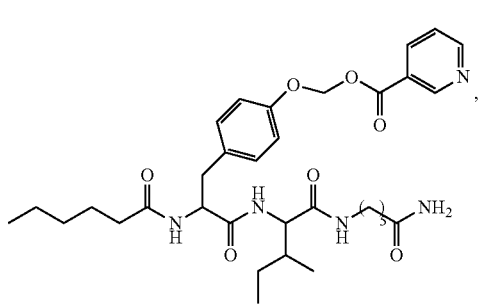
A17l
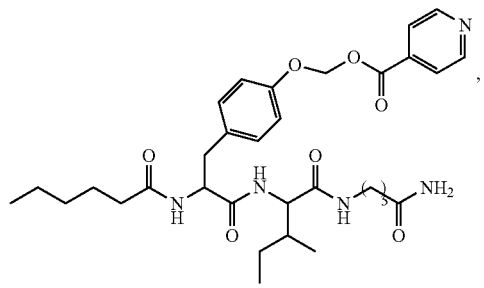
A17m
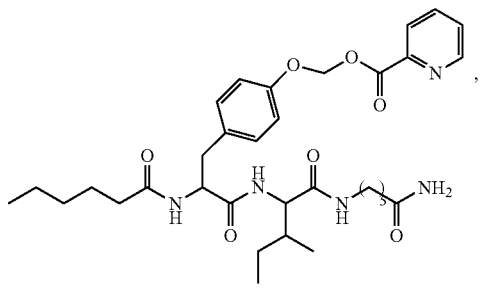

-continued
A18
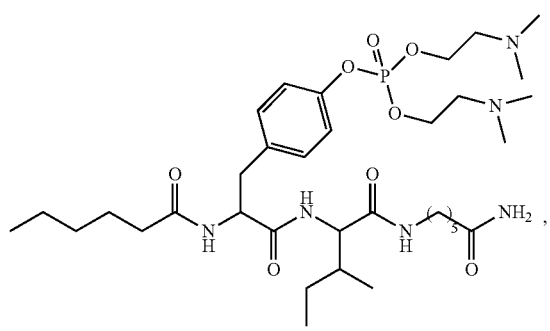
A19
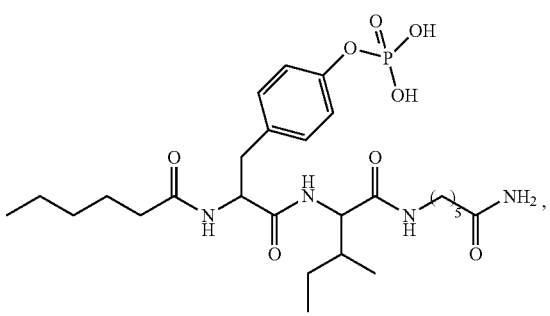
A20
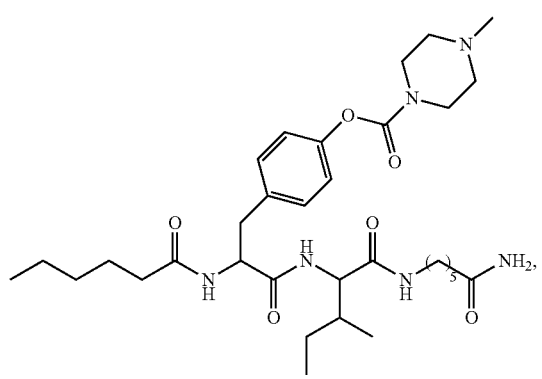
A21
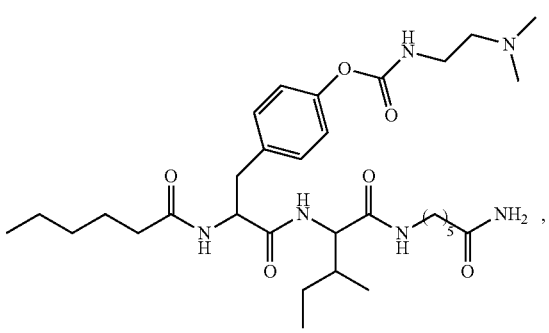
A22
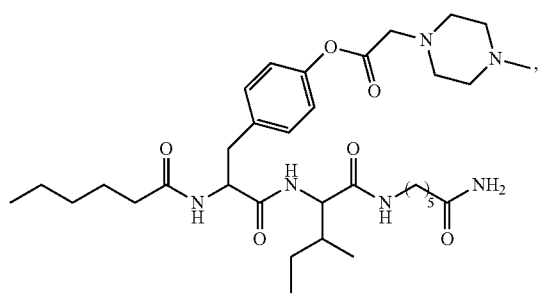
A23
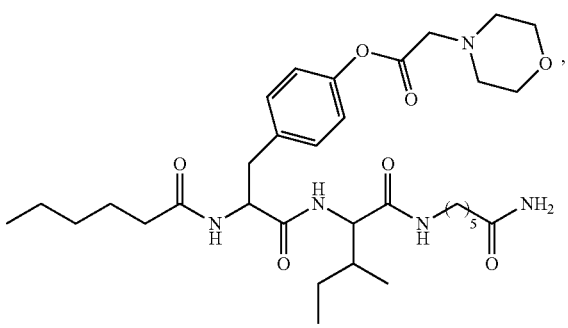
A24
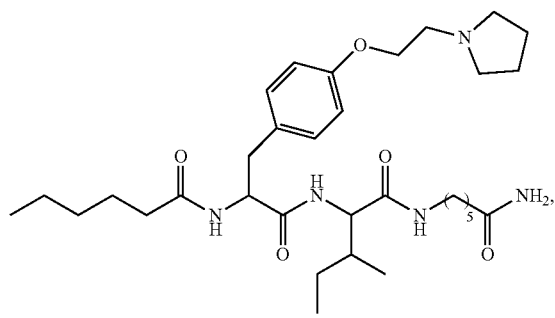
A25
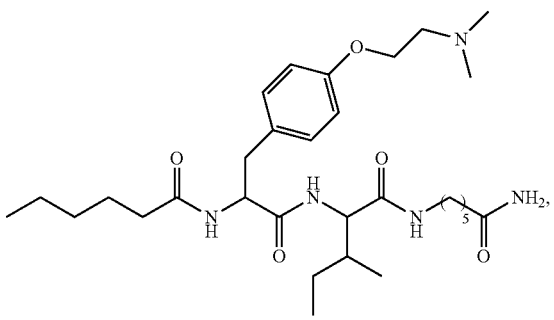

A26

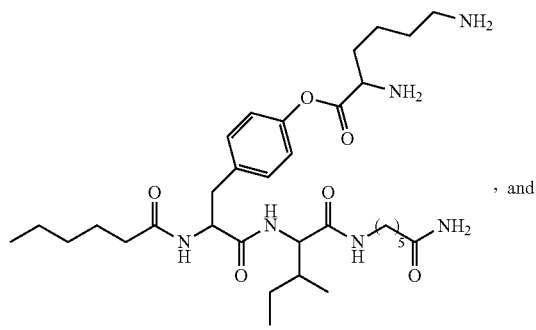

, and or a tautomer or a pharmaceutically acceptable salt thereof, or a pharmaceutically acceptable salt of the tautomer.

12. The compound of claim 11, which is:

A21

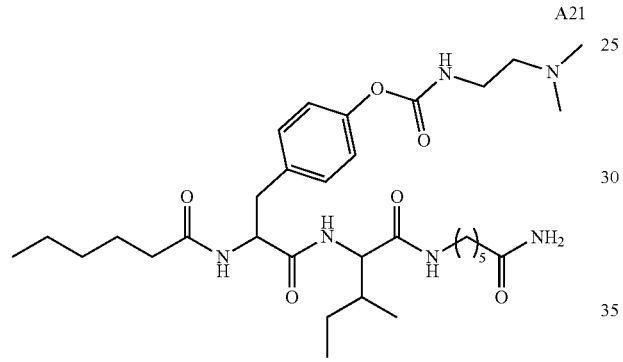

or a pharmaceutically acceptable salt thereof.

13. A pharmaceutical composition comprising the compound of claim 12, or a tautomer or a pharmaceutically acceptable salt thereof, or a pharmaceutically acceptable salt of the tautomer, and a pharmaceutically acceptable carrier or excipient.

14. The compound of claim 11, which is:

A22

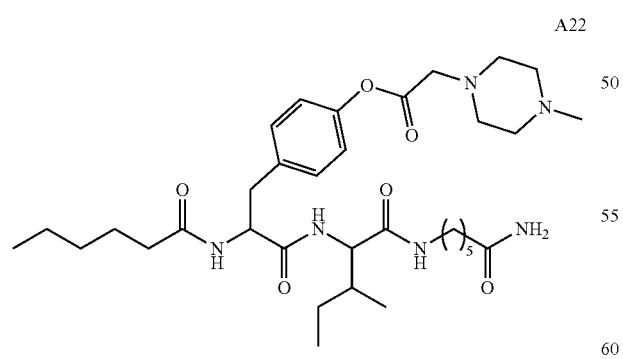

or a pharmaceutically acceptable salt thereof.

15. A pharmaceutical composition comprising the compound of claim 14, or a tautomer or a pharmaceutically acceptable salt thereof, or a pharmaceutically acceptable salt of the tautomer, and a pharmaceutically acceptable carrier or excipient.

16. The compound of claim 11, which is:

A27

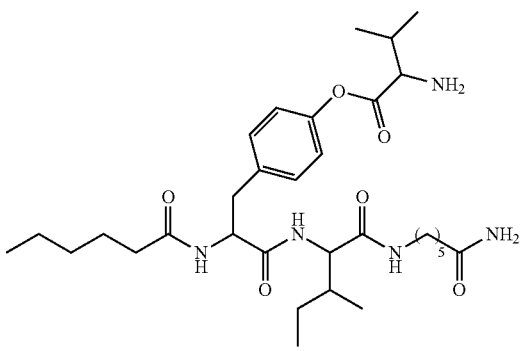

,

A26

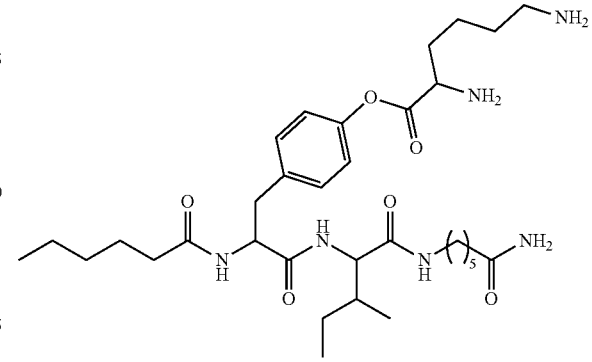

or a pharmaceutically acceptable salt thereof.

17. A pharmaceutical composition comprising the compound of claim 16, or a tautomer or a pharmaceutically acceptable salt thereof, or a pharmaceutically acceptable salt of the tautomer, and a pharmaceutically acceptable carrier or excipient.

18. The compound of claim 11, which is:

A19

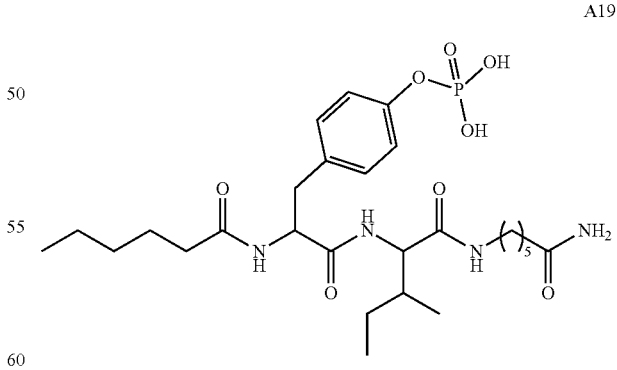

or a pharmaceutically acceptable salt thereof.

19. A pharmaceutical composition comprising the compound of claim 18, or a tautomer or a pharmaceutically acceptable salt thereof, or a pharmaceutically acceptable salt of the tautomer, and a pharmaceutically acceptable carrier or excipient.

20. The compound of claim 18, which is:

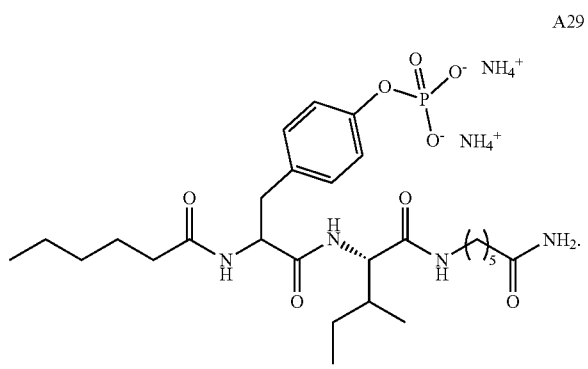

A29

21. A pharmaceutical composition comprising the compound of claim 20, or a tautomer or a pharmaceutically acceptable salt thereof, or a pharmaceutically acceptable salt of the tautomer, and a pharmaceutically acceptable carrier or excipient.

22. The compound of claim 18, which is:

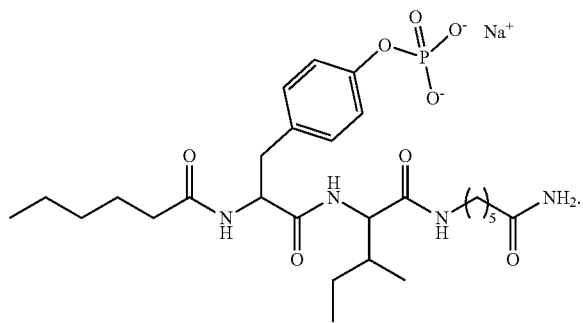

23. A pharmaceutical composition comprising the compound of claim 22, or a tautomer or a pharmaceutically acceptable salt thereof, or a pharmaceutically acceptable salt of the tautomer, and a pharmaceutically acceptable carrier or excipient.

24. A compound of formula (I):

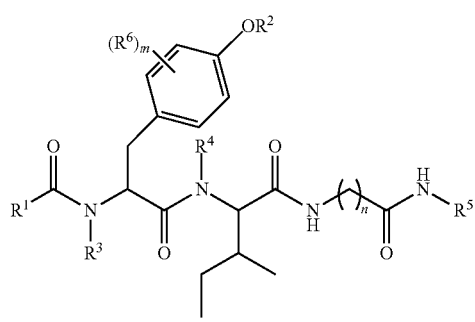

(I)

wherein:
n is 1, 2, 3, 4, 5, 6, 7, 8, or 9;
m is 0, 1, 2, 3, or 4;
$R^1$ is selected from $C_1$-$C_{12}$ alkyl, $C_1$-$C_{12}$ substituted alkyl;
$R^2$ is selected from hydrogen, -$PO(OY)_2$, -$PO(OH)_2$, —C(=O)—Y and —CO—U;

each Y is independently —Z—$(CH_2)_q$—W—$R^b$;
q is 0-4;
each Z and W is independently selected from $CH_2$, $NR^c$ and $R^b$,
or Z and W are taken together to form a $C_3$-$C_8$ heterocycloalkyl;
each $R^c$ is independently hydrogen or $C_1$-$C_4$ alkyl;
each $R^b$ is independently selected from hydrogen, $C_1$-$C_{12}$ alkyl, $C_1$-$C_{12}$ substituted alkyl, $C_3$-$C_8$ heterocycloalkyl, and $C_3$-$C_8$ substituted heterocycloalkyl;
r is 0-5;
U is heterocycloalkyl;
$R^3$ and $R^4$ are independently hydrogen or $C_1$-$C_{12}$ alkyl,
or $R^3$ and $R^4$ are taken together to form a spirocyclic ring system;
$R^5$ is hydrogen; and
each $R^6$ is independently selected from hydrogen, deuterium, $CH_3$, F, $^{19}F$, and $^{18}F$;
wherein each heterocyclic ring contains up to four heteroatoms selected from O, N, and S;
with the proviso that when both Z and W are heteroatoms, the value of q cannot be 1;
or a tautomer or a pharmaceutically acceptable salt thereof, or a pharmaceutically acceptable salt of the tautomer.

25. A pharmaceutical composition comprising the compound of claim 24, or a tautomer or a pharmaceutically acceptable salt thereof, or a pharmaceutically acceptable salt of the tautomer, and a pharmaceutically acceptable carrier or excipient.

26. The compound of claim 24, wherein:
$R^1$ is $C_1$-$C_{12}$ alkyl;
or a tautomer or a pharmaceutically acceptable salt thereof, or a pharmaceutically acceptable salt of the tautomer.

27. The compound of claim 24, wherein:
$R^1$ is $C_1$-$C_{12}$ alkyl optionally substituted with 1-5 substituents independently selected from alkoxy, cyano, halo, and hydroxy;
or a tautomer or a pharmaceutically acceptable salt thereof, or a pharmaceutically acceptable salt of the tautomer.

28. The compound of claim 24, wherein:
$R^1$ is $C_1$-$C_{12}$ alkyl optionally substituted with 1-5 substituents independently selected from alkoxy, cyano, halo, and hydroxy;
each $R^b$ is independently selected from hydrogen; $C_1$-$C_{12}$ alkyl optionally substituted with 1-5 substituents independently selected from alkoxy, cyano, halo, and hydroxy; and $C_3$-$C_8$ heterocycloalkyl optionally substituted with 1-5 substituents selected from $C_1$-$C_6$ alkyl, alkoxy, cyano, halo, hydroxy, and oxo;
or a tautomer or a pharmaceutically acceptable salt thereof, or a pharmaceutically acceptable salt of the tautomer.

29. The compound of claim 24, wherein:
n is 5;
m is 0;
$R^1$ is $C_1$-$C_{12}$ alkyl;
$R^2$ is selected from

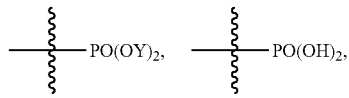

—C(=O)—Y, and —C(=O)—(CH$_2$)$_r$U;
each Y is independently —Z—(CH$_2$)$_q$—W—R$^b$;
q is 0, 1, or 2;
Z and W are independently selected from CH$_2$, NR$^c$ and R$^b$,
or Z and W are taken together to form a C$_3$-C$_8$ heterocycloalkyl;
each R$^c$ is independently hydrogen or C$_1$-C$_4$ alkyl;
each R$^b$ is independently selected from hydrogen, C$_1$-C$_{12}$ alkyl, C$_1$-C$_{12}$ substituted alkyl, C$_3$-C$_8$ heterocycloalkyl, and C$_3$-C$_8$ substituted heterocycloalkyl;
r is 1;
U is heterocycloalkyl;
R$^3$ and R$^4$ are each hydrogen, or R$^3$ and R$^4$ are taken together to form a spirocyclic ring system; and
R$^5$ is hydrogen;
wherein each heterocyclic ring contains up to four heteroatoms selected from O and N;
with the proviso that when both Z and W are heteroatoms, the value of q cannot be 1;
or a tautomer or a pharmaceutically acceptable salt thereof, or a pharmaceutically acceptable salt of the tautomer.

30. The compound of claim 29, wherein:
R$^1$ is C$_5$ alkyl,
or a tautomer or a pharmaceutically acceptable salt thereof, or a pharmaceutically acceptable salt of the tautomer.

31. The compound of claim 29, wherein:
R$^2$ is

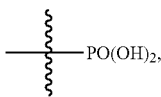

—PO(OH)$_2$, or a tautomer or a pharmaceutically acceptable salt thereof, or a pharmaceutically acceptable salt of the tautomer.

32. The compound of claim 31, which is a pharmaceutically acceptable salt.

33. The compound of claim 29, wherein:
R$^2$ is

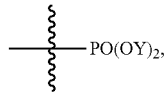

—PO(OY)$_2$, or a tautomer or a pharmaceutically acceptable salt thereof, or a pharmaceutically acceptable salt of the tautomer.

34. The compound of claim 29, wherein:
R$^2$ is —C(=O)—Y,
or a tautomer or a pharmaceutically acceptable salt thereof, or a pharmaceutically acceptable salt of the tautomer.

35. The compound of claim 29, wherein:
R$^2$ is —C(=O)—(CH$_2$)$_r$U,
or a tautomer or a pharmaceutically acceptable salt thereof, or a pharmaceutically acceptable salt of the tautomer.

36. The compound of claim 29, wherein:
R$^3$ and R$^4$ are each hydrogen,
or a tautomer or a pharmaceutically acceptable salt thereof, or a pharmaceutically acceptable salt of the tautomer.

37. The compound of claim 29, wherein:
R$^3$ and R$^4$ are taken together to form a spirocyclic ring system,
or a tautomer or a pharmaceutically acceptable salt thereof, or a pharmaceutically acceptable salt of the tautomer.

38. The compound of claim 29, which is a pharmaceutically acceptable salt.

* * * * *